(12) United States Patent
Kuebler et al.

(10) Patent No.: US 6,519,032 B1
(45) Date of Patent: *Feb. 11, 2003

(54) FIBER OPTIC APPARATUS AND USE THEREOF IN COMBINATORIAL MATERIAL SCIENCE

(75) Inventors: Sigrid C. Kuebler, Sunnyvale, CA (US); James Bennett, Santa Clara, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 149 days.

(21) Appl. No.: 09/689,553

(22) Filed: Oct. 11, 2000

Related U.S. Application Data

(63) Continuation-in-part of application No. 09/285,335, filed on Apr. 2, 1999, now Pat. No. 6,175,409.
(60) Provisional application No. 60/080,652, filed on Apr. 3, 1998.

(51) Int. Cl.[7] .............................. G01N 21/00; G01N 1/10
(52) U.S. Cl. ........................................ 356/337; 356/246
(58) Field of Search ................................ 356/337–343, 356/246; 422/101, 102, 99

(56) References Cited

U.S. PATENT DOCUMENTS

| | | | |
|---|---|---|---|
| 3,617,222 A | * 11/1971 | Matte | 23/230 |
| 4,101,383 A | * 7/1978 | Wyatt et al. | 195/103.5 |
| 4,231,661 A | * 11/1980 | Walsh et al. | 356/340 |
| 4,234,538 A | * 11/1980 | Ginsberg et al. | 422/64 |
| 4,240,751 A | * 12/1980 | Linnecke et al. | 356/409 |
| 4,267,509 A | * 5/1981 | Graham | 324/244 |
| 4,283,143 A | * 8/1981 | Patterson | 356/336 |
| 4,569,228 A | * 2/1986 | Bellgardt et al. | 73/432 |
| 4,626,684 A | * 12/1986 | Landa | 250/328 |
| 4,707,134 A | * 11/1987 | McLachlan et al. | 356/342 |
| 4,969,741 A | * 11/1990 | Kennedy et al. | 356/338 |
| 4,975,237 A | 12/1990 | Brown | |
| 4,983,040 A | 1/1991 | Chu et al. | |

(List continued on next page.)

FOREIGN PATENT DOCUMENTS

| | | |
|---|---|---|
| DE | 197 25 211 C1 | 6/1998 |
| EP | 697 590 A1 | 8/1995 |
| EP | 762 114 A2 | 9/1996 |
| EP | 822 395 A2 | 7/1997 |

OTHER PUBLICATIONS

Ansari et al., Applied Optics (1993) 32 (21) 3822–3827 "Microemulsion characterization by the use of a noninvasive backscatter fiber optic probe".

Ansari et al., Coherence Domain Optical Methods in Bio-medical Science and Clinical Applications II, SPIE, vol. 3251 "Dynamic light scattering particle size measurements in turbid media".

Ansari et al., J. Crystal Growth (1996) 168:216–226 A fiber optic probe for monitoring protein aggregation, nucleation and crystallization.

(List continued on next page.)

*Primary Examiner*—Michael P. Stafira

(57) ABSTRACT

Methods, systems and devices are described for rapid characterization and screening of liquid samples to determine properties (e.g., particle size, particle size distribution, molar mass and/or molar mass distribution) thereof with static light scattering and/or dynamic light scattering. The liquid samples can be solutions, emulsions, suspensions or dispersions. One method, includes providing a vessel containing a liquid sample having an exposed surface that defines a gas-liquid sample interface, and analyzing the sample by light scattering methods that include transmitting light through the gas-liquid sample interface into the sample, and detecting light scattered from the sample or from a component thereof. Additional methods are directed to characterizing a plurality of liquid samples or components thereof. The methods, systems, and devices have applications in high-throughput screening, and particularly, in combinatorial materials research and in industrial process control.

62 Claims, 13 Drawing Sheets

U.S. PATENT DOCUMENTS

| | | | |
|---|---|---|---|
| 5,011,279 A | | 4/1991 | Auweter et al. |
| 5,056,918 A | * | 10/1991 | Bott et al. .................. 356/336 |
| 5,155,549 A | * | 10/1992 | Dhadwal .................... 356/336 |
| 5,284,149 A | | 2/1994 | Dhadwal et al. |
| 5,434,667 A | | 7/1995 | Hutchins et al. |
| 5,502,561 A | | 3/1996 | Hutchins et al. |
| 5,540,891 A | | 7/1996 | Portmann et al. ........... 422/102 |
| 5,627,642 A | | 5/1997 | Dhadwal et al. |
| 5,751,424 A | * | 5/1998 | Bostater, Jr. ................ 356/342 |
| 5,815,611 A | | 9/1998 | Dhadwal et al. |
| 5,969,814 A | * | 10/1999 | Barber et al. ............... 356/339 |
| 5,973,779 A | | 10/1999 | Ansari et al. ............... 356/301 |
| 6,034,775 A | | 3/2000 | McFarland et al. |

OTHER PUBLICATIONS

Ansari et al., Medical Applications of Lasers in Dermatology, Ophthalmology, Denistry and Endoscopy, SPIE 3192 (1997) "In vivo "cataractograms" using a compact backscatter dynamic light scattering (DLS) probe".

Ansari et al., Ophthalmic Technologies VIII, SPIE vol. 3246, (1998) "Measuring Lens opacity: combining quasi–elastic light scattering with Scheimpflug imaging system".

Ansari et al., Proc. Biomedical Optoelectronics in Clinical Chemistry and Biotechnology, SPIE, (1995) 2629 (23) "Sizing of collodial particles and protein molecules in a hanging fluid drop".

Bremer et al., Langmuir (1993) 9:2008–2014 "Fiber optic dynamic light scattering, neither Homodyne nor Heterodyne".

Brookhaven FOQELS Particle Analysis in Concentrated Suspensions, 2 pages.

Brown et al., Applied Optics (1990) 29 (28): 4159–4169.

Carr et al., Anal. Biochem. (1998) 175: 492–499 Determination of protein size in chromatography column eluants by on–line photon correlation spectroscopy.

Claes et al., Analytics Chimica Acta. (1991) 249: 227–230 "Instrumentation for molecular size detection for analytical biotechnology".

Combustion & Fluids CF–060–2, NASA, Technology Opportunity "Noncontact Fiber–Optic Particle–Sizing Probe".

Dhadwal et al., Applied Optics (1993) 32 (21): 3901–3904 "Integrated fiber optics probe for dynamic light scattering".

Dhadwal et al., Particulate Science and Technology (1994) 12: 139–148 Compact Backscatter Fiber Optics Systems for Submicroscopic Particle Sizing.

Http://www.fluor.unibe.ch/group/SanRemo/proceeding-.html "Micro–volume Dynamic Light Scattering and simultaneous Video Microscopic Observation for Screening of Protein Crystal Growth".

Http://www.protein–solutions.com/dpopts.html "Protein solutions' FOR–APD Detector".

Kourti et al., pp: 160–163 "On–line particle size determination in a latex reactor using dynamic light scattering".

Lilge et al., Colloind Polym Sci (1991) 269: 704–412 "Diffusion in concentrated dispersions: a study with fiber–optic quasi–elastic light scattering (FOQELS)".

Microgravity News Fall 1996, htpp://mgnwww.larc.nasa.gov/fall96/fall96lead.html "Building bridges for the benefit of all: The Dynamic Light–Scattering Probe".

Microgravity News Fall 1996, htpp://mgnwww.larc.nasa.gov/fall96tech.html "Fiber Optic Probe for Early Diagnosis of Eye Diseases".

Mignani et al., Diffractive Optics and Optical Microsystems, Plenum Press, New York, 1997 pp: 311–325 "Radially Gradient Index Lenses: Applications To Fiber Optic Sensors".

Sadasivan et al., J. colloid and interface science (1997) 193:145–151 Compact Fiber Optic Dynamic Light Scattering System.

Schrof et al., Physical Review (1998) 57 (3): R2523–2526 "Raman correlation spectroscopy: A method for studing chemical composition and dynamics of disperse systems".

Spinelli et al., Rev. Sci. Instrum., (1996) 67 (1): 55–61 "Activity quenched single–photon avalanche diode for high repetition rate time–gated photon counting".

Van Keuren et al., Langmuir (1993) 9: 2883–2887 "Fiber–optic quasielastic light scattering in concentrated latex dispersions: Angualr dependent measurements of singly scattered light".

Van Kueren et al., Colloids and Surfaces A: Physicochemical and Engineering Aspects (1993) 77: 29–37 "Diffusing-–wave spectroscopy in concentrated latex dispersions: an investigation using single–mode fibers".

Wiese et al., Pys. Chem. 96 (12): 1818–1828 (1992) "Fiber–Optic Quasielastic Light Scattering in Concentrated Latex Dispersions: The Performance of Single–Mode vs. Monomode Fibers".

Wiese et al., J. Chem. Phys. (1991) 84 (10): 6429–6443 "Single–mode fibes in fiber–optic quasielastic light scattering: A study of the dynamics of concentrated latex dispersions".

Wiese et al., Pys. Chem. (1993), 97(12): 1589–1597 Fiber–Optic Quasielastic Light Scattering in Concentrated Latex Dispersions: The on–line process control of carotenoid micronization.

Will et al., Rev. Sci. Instrum. (1996), 67 (9): 3164–3169 "Dynamic light scattering system with a novel scattering cell for the measurement of particle diffusion coefficients".

\* cited by examiner

FIBER OPTIC APPARATUS AND USE THEREOF IN COMBINATORIAL MATERIAL SCIENCE

CROSS REFERENCE TO RELATED APPLICATIONS

This application is a continuation-in-part under 35 U.S.C. § 120 of copending U.S. Ser. No. 09/285,335 entitled "Flow Injection Analysis and Variable-Flow Light Scattering Apparatus and Methods for Characterizing Polymers", filed Apr. 2, 1999 by Nielsen et al., now issued as U.S. Pat. No. 6,175,409 which is hereby incorporated by reference for all purposes, and which itself claims priority under 35 U.S.C. Sec. 119(e) to U.S. Provisional Application Ser. No. 60/080,652, filed Apr. 3, 1998 by Safir et al., which is also hereby incorporated by reference for all purposes.

This application is related to PCT/US99/07304 filed on Apr. 2, 1999 which is hereby incorporated by reference for all purposes. This application is related to the following U.S. patent applications, each of which is hereby incorporated by reference for all purposes: Ser. No. 09/285,363, filed Apr. 2, 1999 by Safir et al., entitled "Rapid Characterization of Polymers", now abandoned in favor of Ser. No. 09/710,801, filed Nov. 8, 2000 by Safir et al., entitled "Rapid Characterization of Polymers", now issued as U.S. Pat. No. 6,406,632; Ser. No. 09/285,393 entitled "Automated Sampling Methods for Rapid Characterization of Polymers", filed Apr. 2, 1999 by Petro et al. now issued as U.S. Pat. No. 6,265,226; Ser. No. 09/285,333 entitled "High-Temperature Characterization of Polymers", filed Apr. 2, 1999 by Petro et al., now U.S. Pat. No. 6,260,407; Ser. No. 09/285,392, entitled "Indirect Calibration of Polymer Characterization Systems", filed Apr. 2, 1999 by Petro et al., now issued as U.S. Pat. No. 6,294,388; and Ser. No. 09/640,094, entitled "Procedure and Device to Deyelop Nanodispersity", filed Aug. 17, 2000 by Carlson et al. under Attorney Docket No. NAE 1157/99.

BACKGROUND OF INVENTION

The present invention generally relates to the characterization of liquid samples by optical techniques, and in preferred embodiments, characterization of polymer samples and non-polymer samples by light-scattering techniques. In particular, the invention relates to methods and apparatus for characterizing liquid samples (e.g. solutions, emulsions, suspensions and/or dispersions) by serial or parallel analysis to determine commercially important properties of the samples or components thereof, such as particle size or particle size distribution. In preferred embodiments, the characterization of the liquid samples or of components thereof is effected in parallel with a probe head comprising an array fiber optic probes suitable for static light scattering and/or dynamic light scattering. The methods and devices disclosed herein are applicable, inter alia, to high-throughput characterization of liquid samples, and especially samples prepared by combinatorial materials science techniques.

Currently, there is substantial research activity directed toward the discovery and optimization of polymeric materials and other materials for a wide range of applications. Although the chemistry of many materials (e.g. polymers) and synthesis reactions (e.g. polymerization) has been extensively studied, it is, nonetheless, rarely possible to predict a priori the physical or chemical properties a particular material will possess or the precise composition and architecture that will result from any particular synthesis scheme. Thus, characterization techniques to determine such properties are an essential part of the discovery process.

Combinatorial chemistry, also referred to as combinatorial materials science and/or high-throughput experimentation, refers generally to methods for synthesizing a collection of chemically diverse materials and to methods for rapidly testing or screening this collection of materials for desirable performance characteristics and properties. Combinatorial chemistry approaches have greatly improved the efficiency of discovery of useful materials. For example, material scientists have developed and applied combinatorial chemistry approaches to discover a variety of novel materials, including, for example, high temperature superconductors, magnetoresistors, phosphors and catalysts. See, for example, U.S. Pat. No. 5,776,359 to Schultz et al., U.S. Pat. No. 5,985,356 to Schultz et al., U.S. Pat. No. 6,004,617 to Schultz et al., and U.S. Pat. No. 6,030,917 to Weinberg et al. In comparison to traditional materials science research, combinatorial materials research can effectively evaluate much larger numbers of diverse compounds in a much shorter period of time. Although such high-throughput synthesis and screening methodologies are conceptually promising, substantial technical challenges exist for application thereof to specific research and commercial goals.

Methods have been developed for the combinatorial (e.g., rapid-serial or parallel) synthesis and screening of libraries of small molecules of pharmaceutical interest, and of biological polymers such as polypeptides, proteins, oligonucleotides and deoxyribonucleic acid (DNA) polymers. However, there have been few reports of the application of combinatorial techniques to the field of polymer science for the discovery of new polymeric materials or polymerization catalysts or new synthesis or processing conditions. Brocchini et al. describe the preparation of a polymer library for selecting biomedical implant materials. See S. Brocchini et al., *A Combinatorial Approach for Polymer Design*, J. Am. Chem. Soc. 119, 4553–4554 (1997). However, Brocchini et al. reported that each synthesized candidate material was individually precipitated, purified, and then characterized according to "routine analysis" that included gel permeation chromatography to measure molecular weight and polydispersities. As such, Brocchini et al. did not address the need for efficient and rapid characterization of polymers.

High-throughput screening approaches have also been developed for a number of combinatorial material science applications, including applications directed toward polymer characterization and toward the identification of useful catalysts. Exemplary approaches are disclosed, for example, in the aforementioned related patent applications, as well as in the following published applications and/or patents: PCT application WO 97/32208 of Willson; U.S. Pat. No. 5,959,297 to Weinberg et al.; PCT application WO 99/64160 of Guan et al.; PCT application WO 00/09255 of Turner et al.; and PCT application WO 00/51720 of Bergh et al.

Light scattering techniques, both static and dynamic, are known in the art for characterizing particle size and shape, and particle size distribution of micron and submicron size materials, among them colloidal dispersions, emulsions, suspensions and/or solutions of inorganic molecules, biological macromolecules or polymers, and/or non-biological polymers.

Dynamic light scattering (DLS) or quasielastic light scattering (QELS) measures the fluctuation of scattered light intensity of suspended fluids or particles exhibiting Brownian motion. For example, and without being bound by theory not specifically recited in the claims, measurement of such intensity fluctuations and autocorrelation techniques can yield the normalized intensity-intensity autocorrelation function $g_2(t)$ that allows measurement of the particle diffusion coefficient D:

$$g_2(t)=\beta\exp(-2_q^2 Dt) \quad (1),$$

where $\beta$ is an instrument parameter ($0<\beta<1$), and the scattering vector q is related to the scattering angle $\theta$, the incident laser wavelength $\lambda$, and the refractive index n of the fluid medium by $$q = \frac{4\pi n}{\lambda}\sin\left(\frac{\theta}{2}\right). \quad (2)$$

The diffusion coefficient D is related to the hydrodynamic radius $R_h$ of the particle as:

$$D = \frac{kT}{6\pi\eta R_h} \quad (3)$$

where T is the temperature in Kelvin, k is the Boltzman constant, $\eta$ is the viscosity of the fluid medium. Although often the primary quantity of interest is the particle size, other quantities of interest like diffusion coefficient may be probed with tracer particles of a defined hydrodynamic radius. Further details of the technique of dynamic light scattering and autocorrelation is described for example in various patents such as U.S. Pat. No. 4,975,237 to Brown, U.S. Pat. No. 4,983,040 to Chu et al., and U.S. Pat. No. 5,011,279 to Autweter et al., and in monographs such as Chu, "*Laser light scattering: basic principles and practice*", Academic Press 1991; Berne, "*Dynamic light scattering: with applications to chemistry, biology, and physics*", Wiley 1976. Dynamic light scattering methods may also be used to determine the average molar mass and molar mass distribution of a polymer. See, for example, Burchard, "*Light Scattering Principles and Development*", Ed. by W. Brown, Clarendon Press 1996.

Static light scattering (SLS) techniques are also well known, and can be used for example, to measure $M_w$ and the radii of gyration ($R_g$) of a polymer in a dilute solution of known concentration. Apparatus and methods suitable for static light scattering are described in the references mentioned in the immediately preceding paragraph.

With the development of combinatorial techniques that allow for the parallel synthesis of arrays comprising a vast number of diverse industrially relevant polymeric and non-polymeric materials, there is a need for methods, devices and systems to rapidly characterize the properties of the synthesized polymer and non-polymer samples.

SUMMARY OF INVENTION

It is therefore an object of the present invention to provide systems and protocols for characterizing combinatorial libraries of polymer samples and non-polymer samples, and particularly, libraries of or derived from synthesis reactions such as polymerization product mixtures, or libraries of or derived from formulations (e.g., of nanodispersion formulations). Such characterization can facilitate the discovery of commercially important polymeric and non-polymeric materials, formulations, catalysts, synthesis (e.g. polymerization) conditions and/or post-synthesis processing conditions. It is also an object of the invention to provide characterization systems and protocols that can be employed in near-real-time industrial process control.

Briefly, therefore, this invention provides a number of approaches for rapid characterization or screening of liquid samples comprising polymers and non-polymer components. The various embodiments disclosed and claimed herein can be employed individually or combined together, and can be combined with other approaches such as those disclosed in the aforementioned related applications. More specifically, characterization approaches and devices are presented involving non-flow characterization with rapid-serial, parallel, serial-parallel and hybrid parallel-serial approaches. Some preferred approaches and embodiments are directed to parallel non-flow characterization of liquid samples.

The invention is directed, in one embodiment, to a method for characterizing a liquid sample or a component thereof. According to the method, a liquid sample having an exposed surface that defines a gas-liquid sample interface is provided. The sample is analyzed by light-scattering methods that include transmitting light into the sample and detecting light scattered from the sample or a component thereof. The light is transmitted or detected through the gas-liquid sample interface. In preferred embodiments, the light is transmitted into the sample through the gas-liquid sample interface, with the scattered light being detected through the same gas-liquid sample interface, or alternatively, through a bottom or side of a sample-holding container. In particularly preferred embodiments, the light is both transmitted and detected through the gas-liquid sample interface. As such, illumination and detection are preferably effected without immersion of a detection probe into the sample. A property of interest can be determined from the detected light (e.g. from the amount or intensity of the detected light or from the intensity fluctuations associated with the detected light).

The invention is also directed to methods for characterizing a plurality of liquid samples or components thereof in rapid-serial, serial-parallel or parallel operational modes.

According to one embodiment, a plurality of liquid samples are provided, where each of the plurality of samples has an exposed surface that defines a gas-liquid sample interface. The plurality of samples are analyzed in parallel by light scattering methods that include simultaneously transmitting light into each of the plurality of samples, and detecting, preferably simultaneously detecting, light scattered from each of the plurality of samples or a component thereof. The light is transmitted or detected through the gas-sample interface of each of the plurality of samples. In preferred embodiments, the light is transmitted through the gas-liquid sample interface, with the scattered light from each of the samples being detected through the gas-liquid sample interface, or alternatively, through a bottom or side of a container holding each of the samples. In a particularly preferred embodiment, the light is both transmitted and detected through the gas-liquid sample interface. A property of interest can be determined from the detected light.

In each of the aforedescribed embodiments, the gas-liquid interface is preferably substantially planar in the region through which the incident light is transmitted, and if applicable, through which the scattered light is detected. In some embodiments, the shape of the gas-liquid interface is controlled such that a difference in scattering angle of not more than about 10° results relative to the scattering angle from a perfectly planar gas-liquid interface.

According to another embodiment for characterizing a plurality of liquid samples or components thereof, a plurality of liquid samples, preferably four or more liquid samples, are provided—on a common sample holder or on two or more sample holders. A light scattering probe or an array comprising two or more light scattering probes (e.g., arranged in a probe head) are provided, and the system is adapted for relative translation of the sample holder(s) and/or probe(s)—such that the sample holder(s), the probe (s) or both can be moved relative to each other to effect a rapid-serial, serial-parallel or parallel operational mode.

More specifically, in a rapid-serial variation of such embodiment, a first sample of a plurality of liquid samples is analyzed by light scattering methods that include transmitting light from a probe into the first sample, and detecting light scattered from the first sample or a component thereof. The one or more sample holder and/or the probe are then translated relative to each other—e.g., with the sample holder(s) moving relative to the probe, with the probe moving relative to the sample holder, or with both the sample holder(s) and the probe moving relative to each other. A second sample of the plurality of liquid samples is then analyzed by light scattering methods that include transmitting light from the probe into the second sample, and detecting light scattered from the second sample or a component thereof.

In a serial-parallel variation of such embodiment, four or more samples are characterized as follows. A first plurality of the four or more samples is analyzed in parallel by light scattering methods (e.g., by simultaneously transmitting light from each of the two or more probes into the first plurality of samples, respectively, and detecting, preferably simultaneously detecting, light scattered from each of the first plurality of samples or a component thereof). The first plurality of samples may be provided on a common (e.g., first) sample holder, or may be provided on separate sample holders. The sample holder(s) and/or the array of two or more probes are then translated relative to each other—e.g., with the sample holder(s) moving relative to a stationary array of probes, with the array of probes moving relative to stationary sample holder(s), or with both the sample holder (s) and the array of probes moving relative to each other. A second plurality of the four or more samples is then analyzed in parallel (e.g. by light scattering methods that include simultaneously transmitting light from each of the two or more probes into the second plurality of samples, respectively, and detecting, preferably simultaneously detecting, light scattered from each of the second plurality of samples or a component thereof). The second plurality of samples may likewise be provided on a common (e.g. second) sample holder, or may be provided on separate sample holders.

In a parallel variation of such embodiment, a first plurality of liquid samples, and preferably a first set of four or more liquid samples are provided on a first common sample holder, and a second plurality of liquid samples, preferably a second set of four or more liquid samples are provided on a second common sample holder. The first and second sample holders can, optionally, be mounted, situated or positioned on a sample holder support. An array comprising two or more light scattering probes (e.g., arranged in a probe head) are provided, and the system is adapted for relative translation of the sample holders and/or probes. Preferably, the number of probes and the spatial arrangement of probes included within the array of probes corresponds, respectively, to the number of samples and the spatial arrangement of samples on each of the first and second sample sample holder. As such, relative motion between the sample holders and the array of the probes can effect characterization in a fully parallel operational mode with respect to the samples on each sample holder.

The invention is further directed to a method for identifying useful materials.

In general, such methods can include characterizing a liquid sample, a plurality of samples or four or more samples by any of the aforementioned methods of the invention by analyzing the samples as described, determining a property of the samples from the detected scattered light (if not already required by such methods), and comparing the detected scattered light and/or the determined property.

In a preferred method for identifying useful materials, a library of liquid samples is provided, with the library comprising four or more different liquid samples (e.g. different polymer molecules/components, different inorganic compositions, different formulations, etc.). Such library is preferably a reaction product library such as a polymerization product library, a catalyst-synthesis reaction library, or a formulations product library (e.g., nanodispersion formulations). The four or more samples can be on a common sample holder, or on two or more separate sample holders. The four or more samples are analyzed in parallel by light scattering methods that include simultaneously transmitting light into at least four of the four or more samples, and detecting, preferably simultaneously detecting, light scattered therefrom or from a component thereof. A property of the at least four samples or of a component thereof can be determined, preferably simultaneously. The determined property of the at least four samples can be compared, with such comparison providing a basis (e.g., metric) for identifying a useful material.

In a particularly preferred variation of such embodiment, two or more sample holders (e.g., microtiter plates), each comprising a plurality (e.g., four or more) of different samples, can be arranged on a sample holder support—for example, on a carousel surface—adapted such that the array of probes can be used to analyze a plurality of samples in serial-parallel or parallel manner on a first sample holder, then subsequently, to analyze a pluarlity of samples in serial parallel or parallel on a second sample holder. Automated handling of sample holders—such as six microtiter plates mounted on a sample holder support (mount) in a 2×3 matrix—can facilitate very high throughput characterization.

The following more particular aspects of the invention are contemplated in connection with each of the aforedescribed embodiments. The sample is preferably a solution, emulsion, dispersion or suspension of polymers or non-polymers (e.g. inorganic elements or compounds), or a combination thereof (e.g., a sample comprising solvated components as well as dispersed components). The sample holder can be a common substrate comprising a number of vessels and/or wells integrally formed in the substrate and/or situated in the substrate. A microtiter plate is an exemplary sample holder. The light-scattering techniques are preferably static light scattering techniques and/or dynamic light scattering techniques. Other light-scattering techniques, such as fluorescence light scattering techniques can be used in connection with each of the embodiments of the invention. Additionally, other optical techniques, including optical spectroscopy techniques, such as infrared (IR) spectroscopy, ultraviolet (UV) spectroscopy, Raman spectroscopy and fluorescence spectroscopy are contemplated for use in connection with each of the embodiments of the invention, in addition to or alternatively to the light-scattering techniques disclosed herein. Hence, although the invention is described primarily with regard to such light-scattering techniques, the scope of the invention should not be unnecessarily limited by such exemplary description. The determined property is preferably particle size, particle size distribution, molar mass and molar mass distribution, but other properties of interest can also be determined (e.g., viscosity, or other properties related to or derivable from the diffusion coefficient, as for example, in the aforementioned equation (1) and equation (3)).

The invention is directed still further to an apparatus for characterizing a plurality of liquid samples. The apparatus comprises a sample holder suitably configured (i.e. adapted) to hold or contain an array of four or more liquid samples in combination with a probe head comprising an array of two or more fiber optic probes. The fiber optic probes are arranged to correspond to the array of samples or to a subset thereof. Each of the two or more fiber optic probes are adapted as well to simultaneously illuminate the liquid samples for analysis by light scattering, and in preferred embodiments, to simultaneously detect light scattered by the samples or components thereof. The apparatus can further comprise a translation station (e.g. such as an x-y-z robotic transfer device) for translating the sample holder and/or the probe head relative to each other. In a particularly preferred embodiment, the sample holder is adapted to present the four or more samples in a substantially coplanar relationship to each other, and the probe head comprises the two or more fiber optic probes in a substantially coplanar relationship to each other. In another particularly preferred embodiment, the apparatus can comprise the probe head in combination with two or more sample holders, preferably supported by a common sample-holder support.

The invention is also directed to analyzing various regions of a single sample in parallel. According to this approach, an array of fiber optic probes (e.g., light-scattering probes) are used to simulataneously illuminate two or more distinct regions—scattering volumes—of a single samples, and the light scattered from each of the two or more regions is detected.

Hence the methods, systems and devices of the present invention are particularly suited for screening of arrays of reaction product mixtures, such as polymerization product mixtures or formulation product mixtures, prepared in the course of combinatorial materials discovery—thereby providing a means for effectively and efficiently characterizing large numbers of different materials. While such methods, systems and devices have commercial application in combinatorial materials science research programs, they can likewise be applied in industrial process applications for near-real-time process monitoring or process control.

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

Figure 1A:
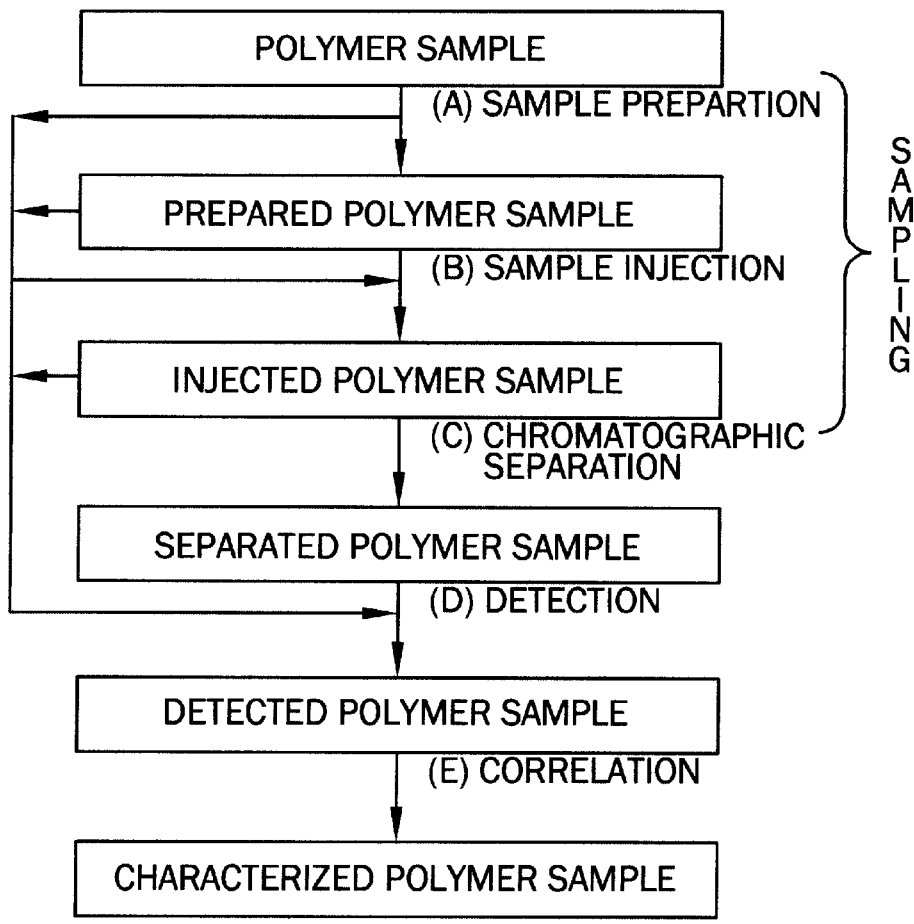
FIG. 1A through FIG. 1F are schematic diagrams showing an overview of polymer characterization process steps (FIG. 1A), a rapid-serial protocol for effecting such steps (FIG. 1B) for a plurality of samples ($s_1, s_2, s_3 \ldots s_n$) to obtain corresponding characterizing property information ($p_1, p_2, p_3 \ldots p_n$), a parallel protocol for effecting such steps (FIG. 1C) and several parallel-serial hybrid protocols for effecting such steps (FIG. 1D, FIG. 1E, FIG. 1F).

The invention is described in further detail below with reference to the figures, in which like items are numbered the same in the several figures.

DETAILED DESCRIPTION OF THE INVENTION

In the present invention, methods and apparatus having features that enable an effective combinatorial materials (e.g. polymer) research program are provided. Such a research program may be directed, for example, to identifying or optimizing commercially valuable polymers, catalysts, inorganic compounds, biological compounds, colloidal systems, formulations, nanodispersants, or other materials, or to other research goals, such as process characterization and optimization. Other applications, including industrial process monitoring or control are also enabled by the present invention.

More specifically, sample (e.g., polymer) characterization approaches and devices are presented involving non-flow characterization, and particularly, involving rapid-serial, parallel, serial-parallel and hybrid parallel-serial approaches. Some preferred approaches and embodiments are directed to parallel and serial-parallel approaches for characterizing liquid samples comprising polymers such as non-biological polymers, and/or inorganic compounds by light scattering techniques. In a preferred embodiment, for example, a non-flow, parallel or serial-parallel dynamic light-scattering system and protocols can be used for sample characterization with very high sample throughput.

As described herein, light scattering techniques, preferably effected with fiber-optic light scattering probes, are used to characterize polymer and non-polymer samples in non-flow characterization systems. The light scattering systems are preferably based on dynamic light scattering methods, systems and devices, but can also be based on static light scattering methods, systems and devices—and in either case, can include non-immersion (i.e., non-contact) and/or immersion (i.e., contact) probes. In a preferred embodiment, scanning fiber optics dynamic light scattering (FODLS), or fiber optic quasi-elastic light scattering methods (FOQELS), systems and devices are employed. The invention can include measuring variable and/or multiple scattering angles. As such, the skilled artisan will appreciate that the invention includes more than one approach to the determination of physical properties of particles executing Brownian motion. In addition to the light scattering, however, embodiments of the invention can also be directed to and effectively employed in connection with optical spectroscopic techniques, including for example infra-red (IR), ultraviolet (UV), fluorescence and/or Raman spectroscopy methods, systems and devices.

These and other aspects of the invention are to be considered exemplary and non-limiting, and are discussed in greater detail below.

The several aspects of the characterization methods and systems disclosed and claimed herein can be advantageously employed separately, or in combination to efficiently characterize materials. In preferred embodiments, these features are employed in combination to form a characterization system that can operate as a high-throughput screen in a materials science research program directed to identifying and optimizing new polymers, new nanodispersants, new catalysts, new formulations, new synthesis reaction (e.g. polymerization) conditions and/or new post-synthesis processing conditions. Certain characterizing information—particularly particle size, and particle size distribution—are broadly useful for characterizing liquid samples.

In embodiments including an array of two or more fiber optics probes, the invention provides the significant advantage of simultaneous measurement and analysis of a corresponding plurality of samples, thereby reducing the average throughput time per sample. In this way, a number of samples a can be screened directly in a high spatial density array with relatively small sample volumes (e.g., a microtiter plate of 96 samples with 9 mm spacing and approximately 400 ul per sample). The automated setup enables a high throughput of samples. For instance, a library comprising 96 samples are regularly and repeatably analyzed in 8 minutes (i.e., an average sample throughput of less than 5 seconds per sample) with the same accuracy and precision of conventional light scattering spectrometers. By adhering to a predefined, spatially determinative format (e.g., a microtiter plate format), a large number of samples may be handled as part of a comprehensive workflow in an automated or semi-automated fashion—from synthesis through screening, thus reducing the overall time for the discovery of new materials.

The particular samples and/or mechanisms disclosed herein should be considered exemplary of the invention and non-limiting as to the scope of the invention. Moreover, although the invention is described and exemplified particularly in connection with polymer samples, such description is intended to be non-limiting with respect to the type of samples or components thereof being characterized.

Combinatorial Approaches for Materials (e.g., Polymer) Science Research

In a combinatorial approach for identifying or optimizing materials such as polymeric materials or reaction conditions such as polymerization reaction conditions, a large compositional space (e.g., of monomers, comonomers, catalysts, catalyst precursors, solvents, initiators, additives, or of relative ratios of two or more of the aforementioned) and/or a large reaction condition space (e.g., of temperature, pressure and reaction time) may be rapidly explored by preparing sample libraries (e.g. polymer libraries) and then rapidly screening such libraries. The sample libraries (e.g. polymer libraries) can comprise, for example, reaction product mixtures (e.g., polymerization product mixtures) resulting from synthesis (e.g. polymerization) reactions that are varied with respect to such factors.

Combinatorial approaches for screening a sample library (e.g. polymer library) can include an initial, primary screening, in which reaction (e.g., polymerization) product mixtures are rapidly evaluated to provide valuable preliminary data and, optimally, to identify several "hits"—particular candidate materials having characteristics that meet or exceed certain predetermined metrics (e.g., performance characteristics, desirable properties, unexpected and/or unusual properties, etc.). Such metrics may be defined, for example, by the characteristics of a known or standard material or sample (e.g. polymer) or known or standard reaction (e.g. polymerization) scheme. Because local performance maxima may exist in compositional spaces between those evaluated in the primary screening of the first libraries or alternatively, in process-condition spaces different from those considered in the first screening, it may be advantageous to screen more focused sample (e.g., polymer) libraries (e.g., libraries focused on a smaller range of compositional gradients, or libraries comprising compounds having incrementally smaller structural variations relative to those of the identified hits) and additionally or alternatively, subject the initial hits to variations in process conditions. Hence, a primary screen can be used reiteratively to explore localized and/or optimized compositional space in greater detail. The preparation and evaluation of more focused sample (e.g. polymer) libraries can continue as long as the high-throughput primary screen can meaningfully distinguish between neighboring library compositions or compounds.

Once one or more hits have been satisfactorily identified based on the primary screening, sample libraries and reaction product libraries (e.g., polymer and polymerization product libraries) focused around the primary-screen hits can be evaluated with a secondary screen—a screen designed to provide (and typically verified, based on known materials, to provide) chemical process conditions that relate with a greater degree of confidence to commercially-important processes and conditions than those applied in the primary screen. In many situations, such improved "real-world-modeling" considerations are incorporated into the secondary screen at the expense of methodology speed (e.g., as measured by sample throughput) compared to a corresponding primary screen. Particular samples (e.g. polymer materials), catalysts, reactants, reaction conditions (e.g. polymerization conditions) or post-synthesis processing conditions having characteristics that surpass the predetermined metrics for the secondary screen may then be considered to be "leads." If desired, additional libraries focused about such lead materials can be screened with additional secondary screens or with tertiary screens. Identified lead material samples (e.g. polymers), monomers, catalysts, catalyst precursors, initiators, additives or reaction conditions may be subsequently developed for commercial applications through traditional bench-scale and/or pilot scale experiments.

While the concept of primary screens and secondary screens as outlined above provides a valuable combinatorial research model for investigating materials and reactions (e.g. polymers and polymerization reactions), a secondary screen may not be necessary for certain chemical processes where primary screens provide an adequate level of confidence as to scalability and/or where market conditions warrant a direct development approach. Similarly, where optimization of materials having known properties of interest is desired, it may be appropriate to start with a secondary screen. In general, the systems, devices and methods of the present invention may be applied as either a primary or a secondary screen, depending on the specific research program and goals thereof. See, with respect to polymers for example, U.S. patent application Ser. No. 09/227,558 entitled "Apparatus and Method of Research for Creating and Testing Novel Catalysts, Reactions and Polymers", filed Jan. 8, 1999 by Turner et al., for further discussion of a combinatorial approach to polymer science research.

Sample Characterization—General Approaches

According to the present invention, methods, systems and devices are disclosed that improve the efficiency and/or effectiveness of the steps necessary to characterize a polymer samples, a non-polymer sample, a plurality of polymer samples (e.g., libraries of polymerization product mixtures) or a plurality of non-polymer samples (e.g., libraries of non-polymeric formulations). In preferred embodiments, a property of a plurality of polymer samples or non-polymer samples or of components thereof can be detected in a characterization system with an average sample-throughput sufficient for an effective combinatorial materials (e.g., polymer) science research program. Although the general approaches are described herein in connection with polymer samples, such approaches are equally relevant with respect to non-polymer samples.

With reference to FIG. 1A, characterizing a polymer sample can include (A) preparing the sample (e.g., dilution). For flow systems, characterizing the sample can further include (B) injecting the sample into a mobile phase of a flow characterization system (e.g., liquid chromatography system, flow-injection analysis system), and/or (C) separating the sample chromatographically. For non-flow systems, the prepared sample may optionally be loaded into an analysis container (or array of containers). Alternatively, the sample may be prepared in situ—in the same container in which the sample will be analyzed. In both flow and non-flow systems, characterizing the sample can further comprise (D) detecting a property of the polymer sample or of a component thereof, and/or (E) correlating the detected property to a characterizing property of interest. As depicted in FIG. 1A, various characterization protocols may be employed involving some or all of the aforementioned steps. For example, a property of a polymer sample may be detected in a non-flow, static system either with preparation (steps A and D) or without preparation (step D). While the physically-detected property (e.g, refracted light, absorbed light, scattered light) from two samples being screened could be compared directly, in most cases the detected property is preferably correlated to a characterizing property of interest (e.g., molecular weight) (step E).

A plurality of polymer samples may be characterized as described above in connection with FIG. 1A. As a general approach for improving the sample throughput for a plurality of polymers, each of the steps, (A) through (E) of FIG. 1A applicable to a given characterization protocol can be optimized with respect to time and quality of information, both individually and in combination with each other. Additionally or alternatively, each or some of such steps can be effected in a rapid-serial, parallel, serial-parallel or hybrid parallel-serial manner.

The throughput of a plurality of samples through a single step in a characterization process is improved by optimizing the speed of that step, while maintaining—to the extent necessary—the information-quality aspects of that step. In many cases, such as with chromatographic separation, speed can be gained at the expense of resolution of the separated components. Although conventional research norms, developed in the context in which research was rate-limited primarily by the synthesis of polymer samples, may find such an approach less than wholly satisfactory, the degree of rigor can be entirely satisfactory for a primary or a secondary screen of a combinatorial library of polymer samples. For combinatorial polymer research (and as well, for many on-line process control systems), the quality of information should be sufficiently rigorous to provide for scientifically acceptable distinctions between the compounds or process conditions being investigated, and for a secondary screen, to provide for scientifically acceptable correlation (e.g., values or, for some cases, trends) with more rigorous, albeit more laborious and time-consuming traditional characterization approaches.

The throughput of a plurality of samples through a series of steps, where such steps are repeated for the plurality of samples, can also be optimized. In one approach, one or more steps of the cycle can be compressed relative to traditional approaches or can have leading or lagging aspects truncated to allow other steps of the same cycle to occur sooner compared to the cycle with traditional approaches. In another approach, the earlier steps of a second cycle can be performed concurrently with the later steps of a first cycle. For example, with reference to FIG. 1A in a rapid-serial approach for characterizing a sample, sample preparation for a second sample in a series can be effected while the first sample in the series is being separated and/or detected. As another example, a second sample in a series can be injected while the first sample in the series is being separated and/or detected. These approaches, as well as others, are discussed in greater detail below.

A characterization protocol for a plurality of samples can involve a single-step process (e.g., direct, non-flow detection of a property of a polymer sample or of a component thereof, depicted as step D of FIG. 1A). In a rapid-serial detection approach for a single-step process, the plurality of polymer samples and a single detector are serially positioned in relation to each other for serial detection of the samples. In a parallel detection approach, two or more detectors are employed to detect a property of two or more samples simultaneously. In a direct, non-flow detection protocol, for example, two or more samples and two or more detectors can be positioned in relation to each other to detect a property of the two or more polymer samples simultaneously. In a serial-parallel detection approach, a property of a larger number of polymer samples (e.g., four or more) is detected as follows. First, a property of a subset of the four or more polymer samples (e.g., 2 samples) is detected in parallel for the subset of samples, and then serially thereafter, a property of another subset of four or more samples is detected in parallel.

Figure 1B:
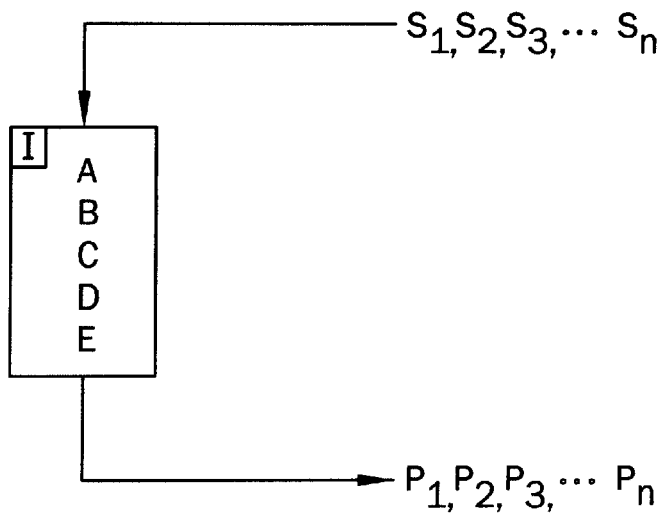
Figure 1C:
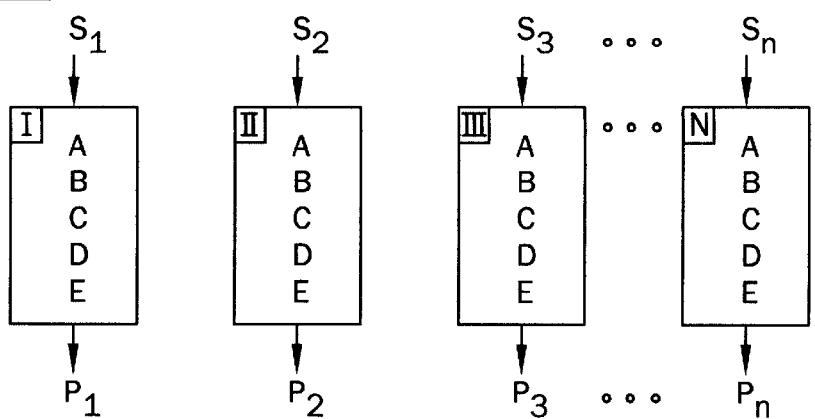

For characterization protocols involving more than one step (e.g., steps A, D and E; steps B, D and E; steps A, B, D and E; steps B, C, D and E; or steps A, B, C, D and E of FIG. 1A), optimization approaches to effect high-throughput polymer characterization can vary. As one example, represented schematically in FIG. 1B, a plurality of polymer samples can be characterized with a single polymer characterization system (I) in a rapid-serial approach in which each of the plurality of polymer samples ($s_1, s_2, s_3 \ldots s_n$) are processed serially through the characterization system (I) with each of the steps (A, B, C, D, E) effected in series on each of the of samples to produce a serial stream of corresponding characterizing property information ($p_1, p_2, p_3 \ldots p_n$). This approach benefits from minimal capital investment, and may provide sufficient throughput—particularly when the steps (A) through (E) have been optimized with respect to speed and quality of information. As another example, represented schematically in FIG. 1C, a plurality of polymer samples can be characterized with two or more polymer characterization systems (I, II, III . . . N) in a pure parallel (or for larger libraries, serial-parallel) approach in which the plurality of polymer samples ($s_1, s_2, s_3 \ldots s_n$) or a subset thereof are processed through the two or more polymer characterization systems (I, II, III . . . N) in parallel, with each individual system effecting each step on one of the samples to produce the characterizing property information ($p_1, p_2, p_3 \ldots p_n$) in parallel. This approach is advantageous with respect to overall throughput, but may be constrained by the required capital investment.

Figure 1D:
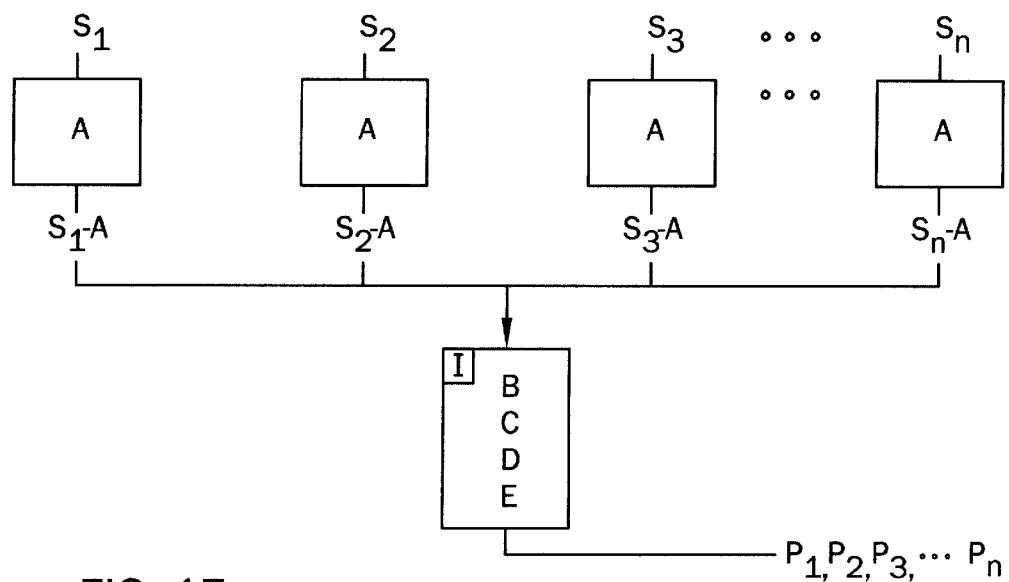
Figure 1E:
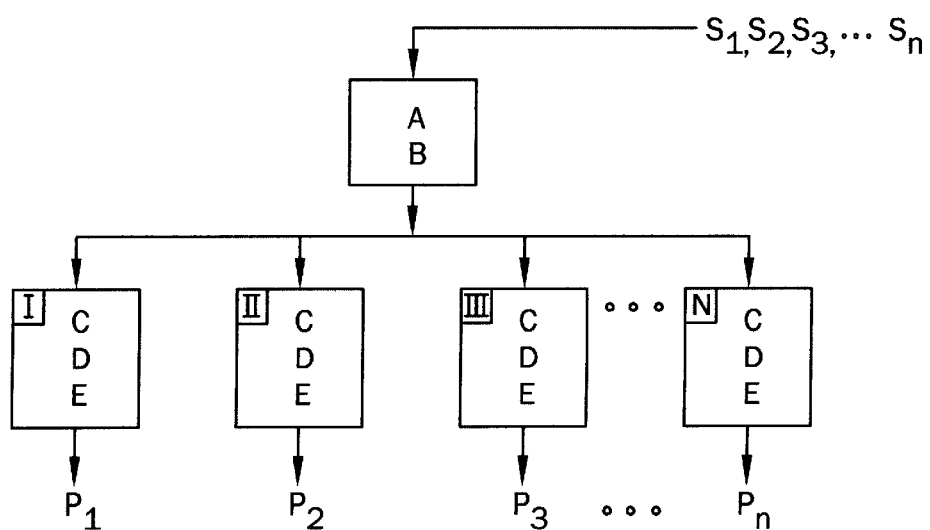
Figure 1F:
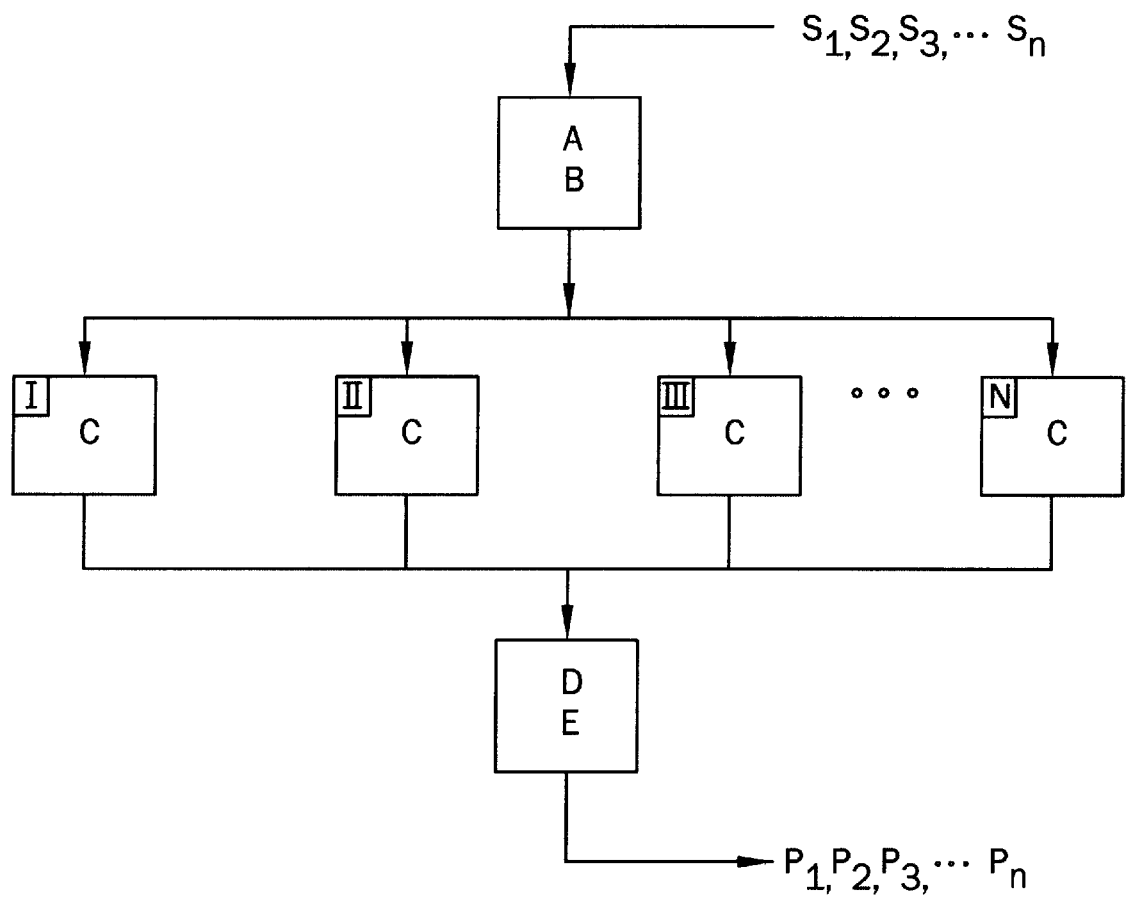

In a hybrid approach, certain of the steps of the characterization process can be effected in parallel, while certain other steps can be effected in series. Preferably, for example, it may be desirable to effect the longer, throughput-limiting steps in parallel for the plurality of samples, while effecting the faster, less limiting steps in series. Such a parallel-series hybrid approach can be exemplified, with reference to Figure 1D, by parallel sample preparation (step A) of a plurality of polymer samples ($s_1, s_2, s_3 \ldots s_n$), followed by serial injection, chromatographic separation, detection and correlation (steps B, C, D and E) with a single characterization system (I) to produce a serial stream of corresponding characterizing property information ($p_1, p_2, p_3 \ldots p_n$). In another exemplary parallel-series hybrid approach, represented schematically in FIG. 1E, a plurality of polymer samples ($s_1, s_2, s_3 \ldots s_n$) are prepared and injected in series into the mobile phase of four or more liquid chromatography characterizing systems (I, II, III . . . N), and then separated, detected and correlated in a slightly offset (staggered) parallel manner to produce the characterizing property information ($p_1, p_2, p_3 \ldots p_n$) in the same staggered-parallel manner. If each of the separation and detection systems has the same processing rates, then the extent of the parallel offset (or staggering) will be primarily determined by the speed of the serial preparation and injection. In a variation of the preceding example, with reference to FIG. 1F, where the detection and correlation steps are sufficient fast, a plurality of polymer samples ($s_1, s_2, s_3 \ldots s_n$) could be characterized by serial sample preparation and injection, staggered-parallel chromatographic separation, and then serial detection and correlation, to produce the characterizing property information ($p_1, p_2, p_3 \ldots p_n$) in series. In this case, the rate of injection into the various separation columns is preferably synchronized with the rate of detection.

Optimization of individual characterization steps (e.g., steps (A) through (E) of FIG. 1A) with respect to speed and quality of information can improve sample throughput regardless of whether the overall characterization scheme involves a rapid-serial or parallel aspect (i.e., true parallel, serial-parallel or hybrid parallel-series approaches). As such, the optimization techniques disclosed hereinafter, while discussed primarily in the context of a rapid-serial approach, are not limited to such an approach, and will have application to schemes involving parallel characterization protocols.

As noted, although the aforementioned general approaches are described particularly in connection with polymer samples, the type of sample is not critical to the invention, and is to be considered exemplary. A skilled artisan can appreciate that the same general approaches can apply to non-polymer samples.

Non-Flow Characterization Systems

In non-flow sample (e.g., polymer) characterization systems, the sample (e.g. polymer sample) is detected statically—in a substantially quiescent state—without flow of the sample. With reference to FIG. 1A, non-flow characterization processes may be effected with a sample preparation (steps A, D and E) or without a sample preparation (steps D and E).

For rapid screening of combinatorial libraries of samples (e.g., polymer samples), is it often not necessary to know the size distribution of samples (e.g., polydispersity index (PDI)). In such cases, parallel light scattering systems may be advantageously employed. Preferably, the polymer samples are diluted in preparation for light-scattering detection. The preparation step can be effected in a rapid-serial, a parallel or a serial-parallel manner.

In a rapid-serial embodiment, a light-scattering detector, such as a dynamic light-scattering (DLS) detector, can be mounted on a platform (e.g. probe head) for staging over an array of polymer samples. The DLS detector can then serially detect the light scattered from each of the samples in sequence. Automated relative motion can be provided between the DLS-platform and the array of polymer samples by robotically controlling the DLS-platform and/or the array of sample containers.

In one parallel embodiment, an entire library of liquid samples (e.g., polymers) can be illuminated and scattered light can be detected from every sample at the same time. A property (e.g., concentration) of the sample (e.g., polymer) in each well may be derived in parallel by using parallel absorbency or refractive index measurements. In this embodiment, the detector can be a static light-scattering (SLS) detector or a dynamic light-scattering (DLS) detector.

In another parallel embodiment, a property of two or more samples (e.g, polymer samples) is detected simultaneously (i.e., in parallel) with two or more light-scattering detectors positioned in appropriate relation to the samples. In a preferred system, the light-scattering detectors are dynamic light-scattering (DLS) detectors, and preferably, fiber-optic DLS detectors. Such a system can also be employed in a pure-parallel, a serial-parallel or hybrid serial-parallel detection approach for screening four or more polymer samples, such as a combinatorial library of reaction product mixtures (e.g., polymerization product mixtures) arranged in an array of sample containers. Here, two or more DLS detectors (e.g., probes) can be mounted on a common platform, also referred to herein as a probe head, for staging over (or equivalently in some embodiments, under) the array of samples (e.g., polymer samples, colloid samples, formulations samples). The two or more DLS detectors can detect the light scattered from two or more of the samples in parallel, and then the DLS-platform (or the array) can be moved such that the two or more DLS detectors can be serially advanced to the next subset of polymer samples. Automated relative motion can be provided between the DLS-platform and the array of (e.g., polymer) samples by robotically controlling the DLS-platform and/or the array of sample containers, typically provided at on or in a sample holder. The number of DLS probes employed in the system can range from 2 to the number of samples (e.g. polymer samples) included within a plurality of (e.g., polymer) samples (as generally discussed above). As discussed below, if separate arrays of DLS probes are used for both illumination (e.g., from above the sample) and detection (e.g., from below the sample), then the number of DLS probes can range from 4 to about two times the number of samples.

A preferred configuration thereof can be a non-flow, immersion or non-immersion parallel DLS configuration. Briefly, with reference to FIG. 2, a parallel DLS system can comprise an array 410 of two or more DLS probes 420, 420', 420" configured in a spatial relationship with respect to each other. Each probe 420, 420', 420" can include a transmitting optical fiber 425, 425', 425" and a receiving optical fiber 430, 430', 430". Although shown in FIG. 2 as being immersed, the probes 420, 420', 420" can also be positioned over the samples of interest in a non-immersed configuration. The samples 20 can be provided in a sample holder 202. Each probe 420, 420', 420" further comprises a single-mode fiber coupler, also referred to as an optic (not shown), suitable for transmitting incident light to a sample and/or collecting scattered light from a sample. These couplers can preferably consist, for example, of a gradient refractive index (GRIN) lens aligned to a single-mode optical fiber—and be mounted at an angle of 45 degrees with respect to each other to provide for a measurement angle of 135 degrees. Other couplers and/or configurations known in the art can also be effectively employed. A laser light can be provided from laser 435 and coupled into the transmitting optical fibers 425, 425', 425" by means of the fiber-optics array 440. The coupled laser light can be delivered into the sample 20 and scattered by one or more particles of the polymer sample. The scattered light can be collected via one or more optics, as described above, and coupled into the receiving optical fiber 430, 430', 430". The receiving optical fiber 430, 430', 430" can be in optical communication with a detector array 450 (e.g., an array of avalanche photodiodes (APD)). Measurements and photon autocorrelation can be taken in a serial or parallel manner using commercially-available autocorrelator boards, such as the ALV 5000/E (ALV GmbH, Langen, Germany). The hydrodynamic radius, $R_h$, and the particle size distribution (e.g., PDI) can be determined from the detected scattered light with commercially-available software. Other suitable configurations can also be arranged by a person of skill in the art.

In each of the aforementioned embodiments, the light-scattering detector can, depending on its design characteristics, be immersed in the polymer sample during detection or, alternatively, be positioned near the surface of the polymer sample for detection without immersion therein. In an immersion embodiment, with further reference to FIG. 2, the array 410 of fiber optic probes 420, 420', 420" can comprise immersion probes adapted for immersion into the liquid samples, and having a transmitting immersion tip 421 and a receiving immersion tip 431, or alternatively, having a common, single tip used for both illumination and detection (not shown in FIG. 2). In a non-immersion embodiment (not shown in FIG. 2; see, for example, FIG. 3A and FIG. 3B), the array 410 of fiber optic probes 420, 420', 420" can comprise one or more non-immersion probes adapted to be positioned above the liquid samples, and having a transmitting non-immersion tip 421 and a receiving non-immersion tip 431.

Additional detailed aspects of the invention are discussed as follows.

Fiber-Optic Probe(s)/Arrays of Fiber Optic Probes

The particular nature of the fiber optic probe or probes employed in the present invention is not generally limiting.

In general, for example, the one or more fiber optic probes employed in connection with the present invention can be a light-scattering probe effective for dynamic and/or static light-scattering analysis, or alternatively, can be a spectroscopy probe effective for optical spectroscopy analysis, such as infrared (IR) spectroscopy, Raman spectroscopy, and ultraviolet (UV) spectroscopy. Miniaturization of fiber optic probes—particularly amenable to analyze samples in a combinatorial format—can be attained by the use of compact cylindrical back scatter fiber optics probes that contain at least one optical fiber connected to the laser source and a second optical fiber connected to a photodetector. Gradient Index (GRIN) micro lenses may adjoin the optical fibers to provide a collimated laser beam into the scattering medium and/or to receive the scattered light and meet spatial coherence requirements on the optical detection system. The axis of the two optical fibers may be collinear or arranged to form an angle with each other. Such micro probes of various designs are described in detail in U.S. Pat. Nos. 4,983,040, 5,155,549, 5,284,149 and 5,815,611, all of which are hereby incorporated by reference herein for all purposes. Probes of these types have been used for particle size measurements of colloidal particles, protein molecules and eye cataracts. The diameter of these fiber optics probes is typically about 5 mm but may be less than 0.5 mm depending on their design. These and similar probes are therefore suited for measuring an array of samples (microtiter plate) in parallel.

Figure 5:
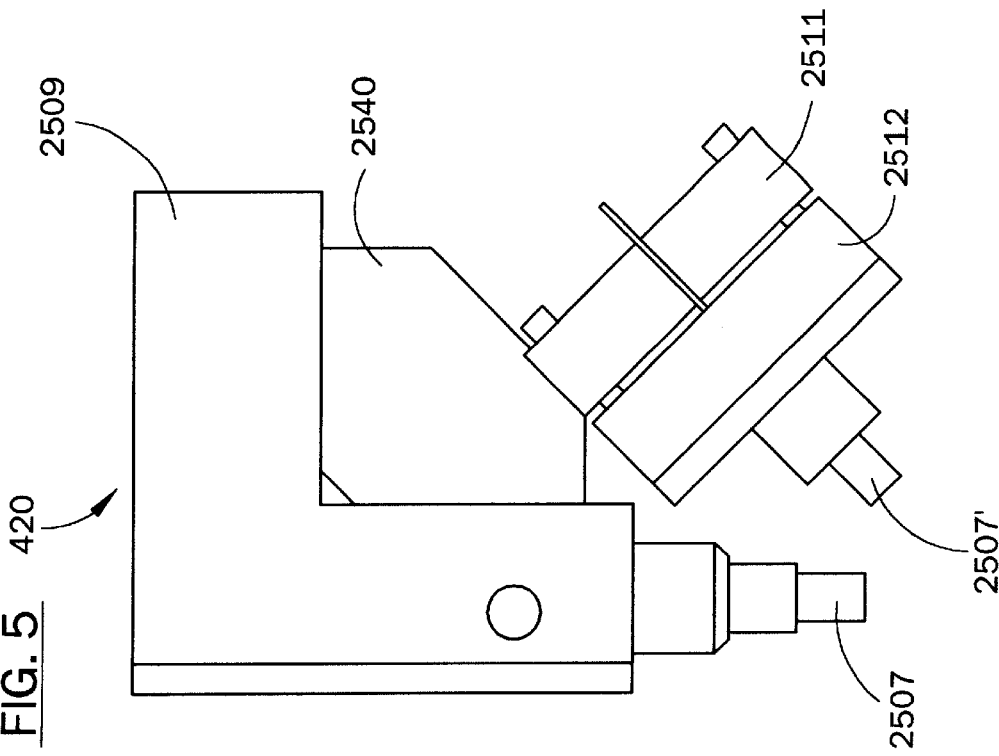
FIG. 5 is a schematic orthographic diagram illustrating one of the light scattering fiber optic probes shown in FIGS. 3A and 3B.

In a preferred embodiment, the fiber optic probe employed in connection with the various embodiments of the invention—either alone, or in an array comprising two or more fiber optic probes (e.g., arranged in, on or by means of a probe head), can comprise an illumination fiber and a detection fiber. Preferably, the detection fiber defines a detection angle with respect to the illumination fiber, and the fiber optic probe is adapted such that the detection angle is adjustable. More specifically, with reference to FIGS. 2 and FIGS. 3A and 3B, the transmitting fiber optic probe (425, 425', 425", FIG. 2) and the receiving fiber optics (430, 430', 430", FIG. 2) can be included within the same probe, such that each of the fiber optic probes (420, 420', 420", 420''' in FIG. 2, FIG. 3A, FIG. 3B) in the array of probes comprises a transmitting optical fiber (425, FIG. 2), as well as a receiving optical fiber (430, FIG. 2). As such, a plurality of such probes can be adapted to simultaneously illuminate a corresponding plurality of samples, and can be further adapted to simultaneously detect light scattered by the liquid samples or a component thereof for analysis by light-scattering. Preferably, both the transmitting fiber optic and receiving fiber optic can be monomode fibers that are terminated with a focusing microlens (GRIN lens) 2507, 2507' with a focal length of, for example, approximate 10 mm. The fibers can be mounted in a holder forming a scattering angle of approximately 135 degrees, i.e. back-scattering geometry (when uncorrected for the different index of refraction for the solvent). The fiber transmitting and/or the fiber receiving the scattered light can be mounted into a kinematic stage to allow fine adjustment of the fibers. Additionally, both probes may be translated along the long axis of the GRIN lens. With reference to FIGS. 3A and 5, for example, each of the fiber optic probes 420, 420' can comprise both a transmitting fiber optic and a receiving fiber optic, each of which is coupled through a GRIN lens 2507, 2507'. The transmitting fiber optic and receiving fiber optic are configured to have a predetermined angular relationship with each other (e.g., approximately a 45 degree angle). Adjustment of the relative positions of the GRIN lenses can be effected in any suitable manner. In one approach, a lens holder body 2509 can be adjustably fastened to an angle mount pad 2540. A pair of tilt mounts 2511 can be situated between a flanged sleeve 2512 and the angle mount pad 2540. Although described herein in the context of light-scattering, the adjustable probe can be modified to be effective for performing IR, UV, fluorescence, and/or Raman spectroscopy and/or to operate with immersion probe(s).

In another embodiment, not shown in the figures, the fiber optic probe of the invention can comprise an illumination fiber (alone, without a detection fiber in that probe), or a detection fiber (alone, without an illumination fiber in that probe). Hence, a receiving fiber optic probe, or an array of receiving fiber optics (430, 430', 430", FIG. 2) can be included in separate probe(s) from an illuminating fiber optic probe or an array of illuminating transmitting fiber optics (425, 425', 425", FIG. 2). In such an embodiment, for example, a first transmitting probe can be adapted to simultaneously illuminate a sample with incident light for analysis by light-scattering. The first probe is positionable over (or alternatively, under) a sample for illumination from above the plane comprising the sample. A second light-scattering probe can comprise a receiving detecting fiber optic and can be adapted to detect light scattered by the scattering volume of the samples or a component thereof for analysis by light-scattering. The second light-scattering probe can be positionable under (or alternatively, over) the sample. A similar configuration can be effected for first and second arrays of probes. Specifically, in such an embodiment, a first probe head comprises a first array of two or more fiber optic probes, with each of the probes being adapted to simultaneously illuminate a sample with incident light for analysis by light-scattering. The first probe head is positionable over (or alternatively, under) the sample holder for such simultaneous illumination from above the plane comprising the samples. A second probe head can comprise a second array of two or more fiber optic probes arranged to correspond to the array of samples or a subset thereof, with each of the probes being adapted to simultaneously detect light scattered by the liquid samples or a component thereof for analysis by light-scattering. The second probe head can be positionable under (or alternatively, over) the sample holder such that the second array of two or more fiber optic probes can simultaneously detect light scattered from the plurality of liquid samples or a component thereof after passing through the sample volume.

Figure 3A:
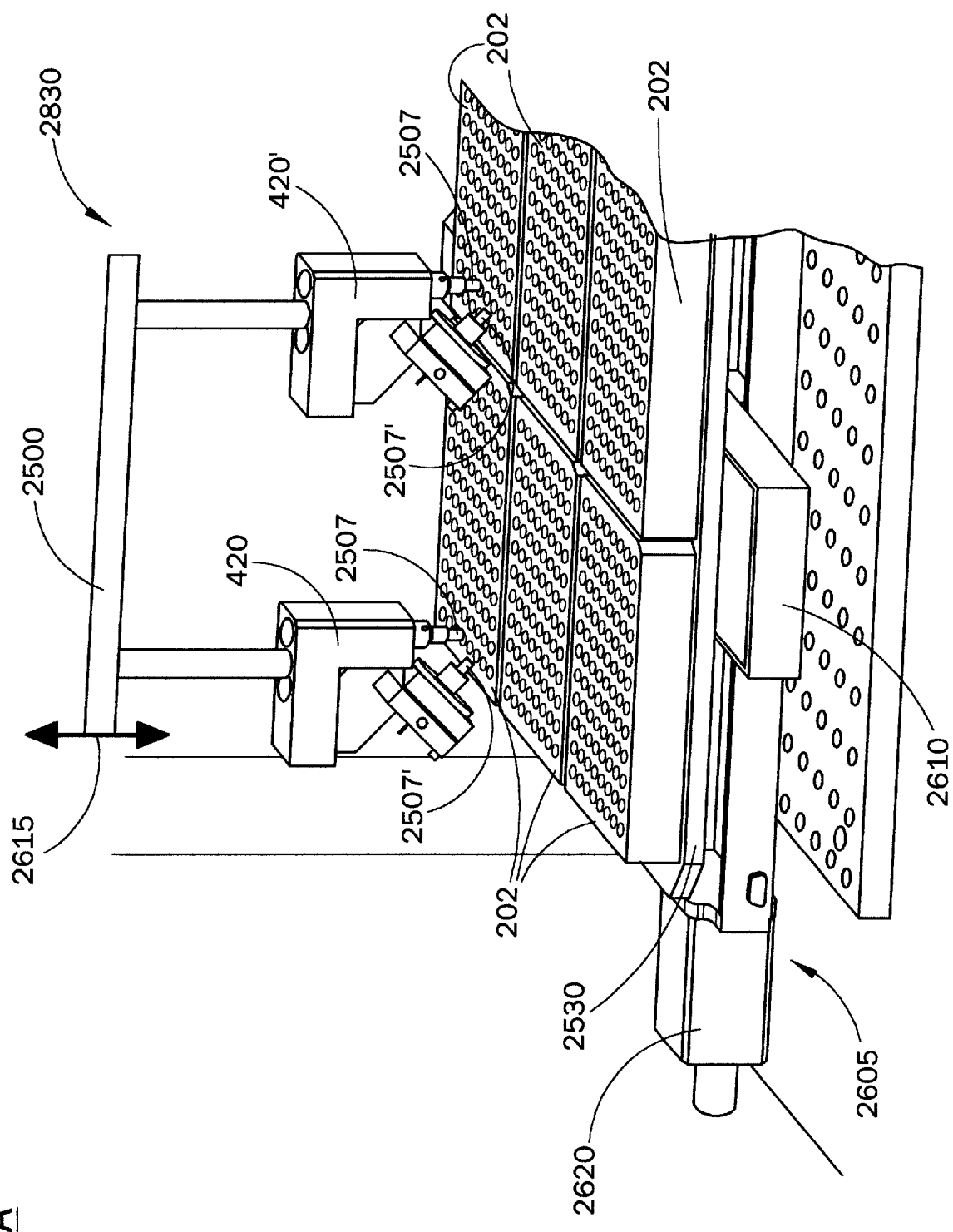
FIGS. 3A and 3B are schematic perspective diagrams illustrating an embodiment of a dynamic light scattering apparatus comprising a probe head that includes an array of two light scattering probes (FIG. 3A) or four light-scattering probes (FIG. 3B), a plurality of sample holders, and a translation station for providing relative motion between the probe head and the sample holders.
Figure 3B:
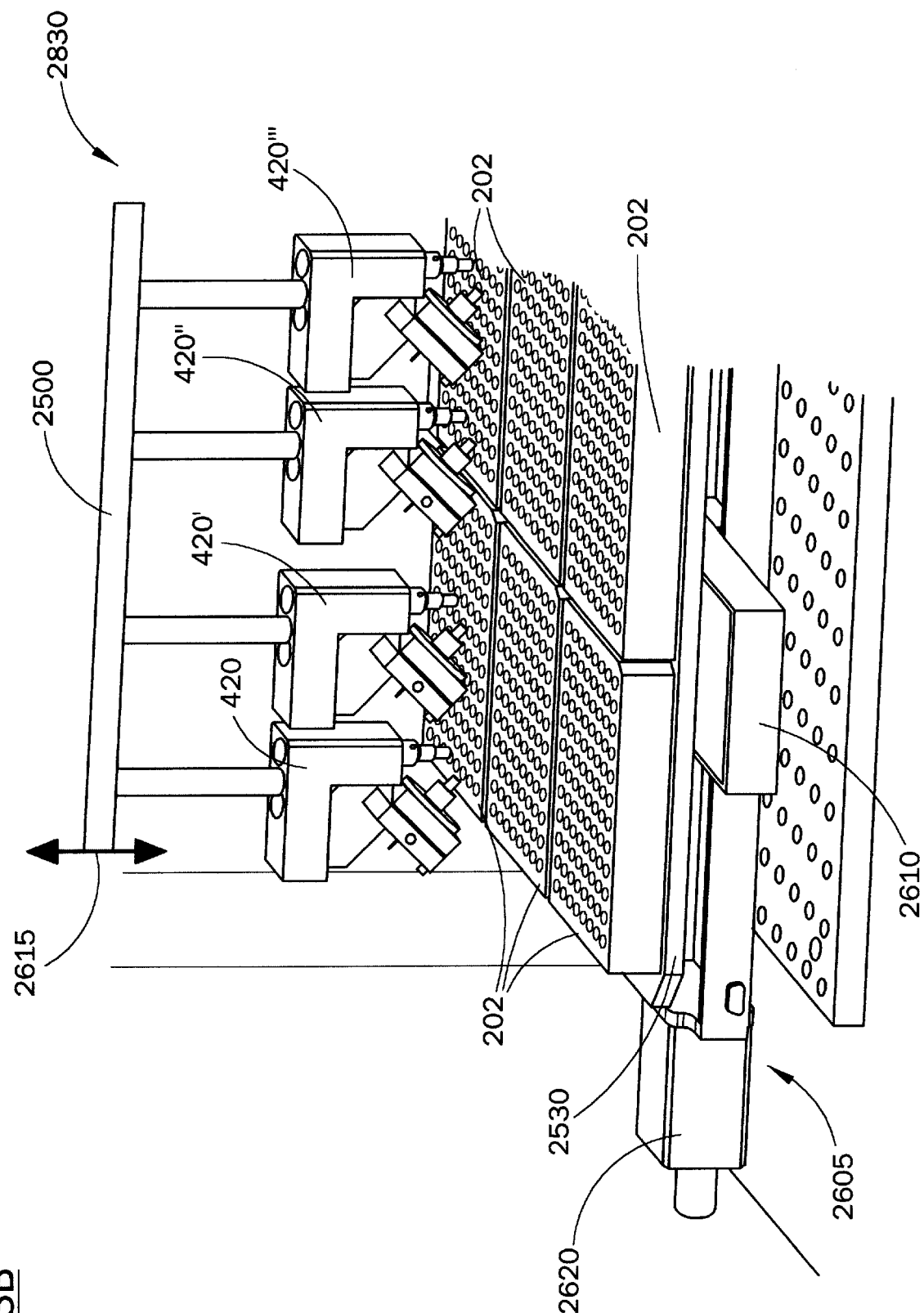

Without regard to the particular design associated with the fiber optic probes, and with further reference to FIGS. 3A and 3B, the fiber optic probes 420, 420' can be configured into an array of fiber optic light-scattering probes.

Hence, a probe head 2500 can consist of one or more fiber optic probes 420, and preferably comprises an array of two or more fiber optic probes 420, 420'. The fiber optic probes 420, 420' can be spatially arranged in the probe head 2500 to correspond to the spatial arrangement of the array of samples or to the spatial arrangement of a subset thereof— for example, with regard to relative horizontal spacing and/or relative vertical position. More specifically, because a plurality of samples being characterized can be presented on one sample holder, or on two or more separate sample holders (discussed below), the spatial arrangement of the light-scattering probes can correspond to the arrangement of samples (or a subset thereof) within a single sample holder, or to the arrangement of samples (or a subset thereof) among two or more sample holders. The number of fiber optic probes in the probe head can generally correspond to the number of samples to be simultaneously characterized. In preferred embodiments, for example, the number of light-scattering probes can correspond to the number of samples in a sample holder, or to a subset thereof. Hence, a probe head—particularly suitable for characterizing samples in an 8×12 array (e.g., microtiter plate)—can comprise an array of two (e.g., 1×2), four (e.g., 1×4, 2×2), eight (e.g., 1×8, 2×4), sixteen (e.g., 2×8, 4×4), forty-eight (e.g., 6×8, 4×12) or 96 (e.g., 8×12) fiber optic probes. In any case, the probe head can include one or more tuning members, such as an x-direction tuning member, a y-direction tuning member, a z-direction tuning member, and/or an angular tuning members, or other suitable tuning structure to facilitate coarse or fine adjustments of the position of the fiber optic (OF) probes relative to each other. The adjustment of the relative probe locations for a probe head can be effected manually or in automated fashion. In an automated embodiment, the probe head can further comprise a motive force source (e.g., stepper motors) for providing controlled, relative motion between probes, such that automated reconfiguration of the array of probes (e.g., with respect to spatial density) can occur (e.g., to accommodate sample holders having different spatial densities). Additionally, the probe head can include tuning members for adjustment of the relative positions (angles, vertical alignment, etc.) of the transmitting optical fibers/optical fiber tip (425/421, FIG. 2) versus the receiving optical fibers/optical fiber tip (430/431, FIG. 2), particularly where the transmitting fiber and detection fibers are on separate probes. As noted above, however, the probes themselves preferably include their own, integral structure for fine adjusting the relative location of the fiber optic tip(s). Preferably, the probe head comprises two or more fiber optic probes in a susbstantially coplanar relationship to each other, to facilitate illumination (and optionally detection) from above (and/or below) one or more sample holders presenting substantially coplanar-oriented samples. In preferred embodiments, the spatial density of fiber optic probes included within the array of fiber optic probes of the probe head can correspond to the spatial density of the samples in the sample holder, or to some subset thereof. In general, in preferred embodiments, the probe head comprises two or more, preferably four or more, more preferably eight or more, even more preferably sixteen or more light-scattering probes. The probe head can comprise higher numbers of light-scattering probes, such as forty-eight or more, or ninety-six or more, or 96*N, where N is an integer that ranges from 1 to about 20, and preferably from 1 to about 5. The spatial density of such arrays of fiber optic light-scattering probes can be not less than about 1 probe per 10 $in^2$, preferably not less than about 1 probe per 1 $in^2$, more preferably not less than about 1 probe per 1 $cm^2$, and still more preferably not less than about 1 probe per 1 $mm^2$. A spatial density of about 9 mm center to center— corresponding to the spatial density of samples in a microtiter plate—is particularly preferred.

The array of probes can be used to characterize a single sample or a plurality of samples. For example, according to one approach, an array of fiber optic probes (e.g., light-scattering probes) can simulataneously illuminate two or more distinct regions—scattering volumes—of a single sample, and the light scattered from each of the two or more regions can be detected. In other embodiments, described below, one or more probes can be used to characterize a plurality of samples.

Rapid-Serial, and Serial-Parallel Embodiments

In a preferred, rapid serial, embodiment for characterizing a plurality of liquid samples, a first sample of a plurality of liquid samples is analyzed by light scattering methods that include transmitting light from a light-scattering probe into the first sample, and detecting light scattered from the first sample or a component thereof. The plurality of samples being characterized are preferably presented on a common sample holder, but can also be presented on two or more sample holders. The sample holder(s) and/or the light-scattering probe are then translated relative to each other—e.g., with the sample holder(s) moving relative to the probe, with the probes moving relative to the sample holder(s), or with both the sample holder(s) and the probe moving relative to each other. A second sample of the plurality of liquid samples is then analyzed by light scattering methods that include transmitting light from the light-scattering probe into the second sample, and detecting light scattered from the second sample or a component thereof. The average sample throughput for characterizing the plurality of samples—and preferably for charactering 10 or more samples (or higher numbers as described below)—can be not more than about 10 minutes per sample, more preferably not more than about 1 minute per sample, and most preferably not more than about 10 seconds per sample. Other preferred sample-throughput/sample analysis rates are described elsewhere herein.

In a preferred, serial-parallel, embodiment for characterizing a plurality of liquid samples or components thereof, four or more liquid samples are provided on one or more sample holders. A probe head comprising an array of two or more light scattering light-scattering probes is also provided. Preferably, the number and arrangement of light-scattering probes corresponds to a subset of the samples presented on the one or more sample holders. Regardless of the particular configuration and/or arrangement, a first plurality of the four or more samples is analyzed in parallel by light scattering methods. The first plurality of samples can be provided on a common sample holder, or alternatively, on separate sample holders (e.g., with a first sample of a first sample holder, and a first sample of a second sample holder). The sample holder(s) and/or the array of two or more probes are then translated relative to each other—e.g., with the sample holder(s) moving relative to a stationary array of probes, with the array of probes moving relative to a stationary sample holder(s), or with both the sample holder(s) and the array of probes moving relative to each other. A second plurality of the four or more samples is then analyzed in parallel. The second plurality of samples can be provided on a common sample holder, or alternatively, on separate sample holders (e.g. with a second sample of a first sample holder, and a second sample of a second sample holder).

With reference to FIG. 3A and FIG. 3B, for example, one or more sample holders 202 can provide a plurality of samples to be characterized. The sample holder(s) 202 can be staged on a sample holder support 2530 (also referred to herein as a sample mount 2530). The particular nature of the sample holder is not critical. In general, the sample holder is adapted to contain, directly or indirectly, a plurality of samples for presentation for characterization. As such, the sample holder can be a common substrate for a spatially determinative library of samples. The sample holder can comprise a plurality of sample containers—integral with a common substrate (e.g., wells in a microtiter plate), or as separate therefrom (e.g. vials placed into vial-receiving wells, or otherwise staged on a common substrate in a spatially-determinative arrangement). Further details regarding the nature of such a substrate and such sample containers are described below in connection with details regarding libraries of samples. In preferred embodiments, the sample holder 202 can present the plurality of samples in a substantially coplanar relationship to each other. In additionally preferred embodiments, the sample holder 202 can present the plurality of liquid samples with an exposed gas-liquid interface, as described in greater detail below. An exemplary, preferred substrate for a library of samples, that is likewise a preferred sample holder, is a microtiter plate. In some embodiments, the microtiter plate can have a bottom (and/or sides) adapted to transmit illuminating and/or scattered light. In embodiments in which incident light is transmitted through or scattered light is detected through the bottom, for example, the bottom of the container or vessel in which the sample(s) reside can be optically transparent at the wavelength of light employed. The sample holder is preferably made of a material, or coated with a material that minimizes backscatter. The sample holder is preferably inert to the samples or the liquid media (e.g., solvent) associated with the sample. The sample holders can be indexed and/or contain orientation features (e.g., notches, alignment apertures, etc.) (not shown in FIGS. 3A and 3B).

Light can be transmitted from a fiber optic probe intlo a sample (rapid-serial embodiment) or simultaneously transmitted from each of two or more fiber optic probes 420, 420' (FIG. 2, FIG. 3A, FIG. 3B) into a first plurality of samples (serial-parallel embodiment), and allowed to interact with the sample(s) in a sample volume. As such, each of the fiber optic probes 420, 420' in the illuminating array comprises a transmitting optical fiber (425, FIG. 2), and is adapted to simultaneously illuminate the liquid samples for analysis by light-scattering. The particular wavelength of the incident illuminating light is not narrowly critical, and can include, generally, light having a wavelength ranging from about 200 nm (ultraviolet) to about 2000 nm (infrared). For preferred light-scattering applications, the light can be visible light (e.g., having a wavelength ranging from about 400 nm to about 700 nm, and preferably from about 450 nm to about 650 nm). In other applications, the illuminating light can be ultraviolet light have a wavelength ranging from about 200 nm to about 400 nm, or alternatively, infrared light having a wavelength ranging from about 700 nm to about 2000 nm. Visible laser light can be generated, for example, by a Helium-Neon laser or Ar-Ion laser whereby the output laser beam may be polarized by itself or be passed through a polarizer. The laser light is coupled into an array of polarization maintaining optical fibers, to simultaneously illuminate a plurality of scattering volumes. Coupling may be achieved by splitting the laser beam (e.g. via a beam-splitter cube or using fiber optic splitters), and using collimation optics to direct the light into the free ends of the optical fibers. Although less preferred, a plurality of laser sources could also be employed. In any case, the intensity of the incident laser beam may be attenuated to accomplish the desired output power (e.g. count rate) of the scattered light on the photodetector. To construct a compact instrument with easy adjustment of the optical components, the laser and the optical components to couple the light into the fibers can be mounted on top of the probe head (2500, FIG. 3A, FIG. 3B) and/or on top of the instrument.

Light scattered by the sample or component thereof in the sample can be detected (serial embodiment) or in the plurality of sample volumes can then be simultaneously detected (serial-parallel embodiment). In a preferred embodiment, shown in FIGS. 3A and 3B, the one or more, or each of the two or more fiber optic probes comprises an illumination fiber and a detection fiber, as described above. In another embodiment, not shown in the figures, a first probe or each of two or more fiber optic probes in a first array of probes can comprise an illumination fiber, while a second probe or each of two or more fiber optic probes of a second array of probes can comprise a receiving detection fiber.

Regardless of the particular configuration for the array of receiving (detection) fiber optics, in each channel, the scattered light can be coherently detected by the receiving optical fiber (430, FIG. 2) and directed to a detector capable of single photon resolution that converts the optical signal to an electrical signal. Single photon detection can be effected, for example, with detectors typically consisting of a photomultiplier tube (PMT) or an avalanche photodiode (APD). The electrical signal is subsequently fed to a data acquisition device (e.g., board, software) that accumulates these signals. For dynamic light scattering, autoorrelation of the data may be achieved by an autocorrelator board or in software, and the obtained autocorrelation function is analyzed to yield particle size, particle size distribution and/or other physical quantities of interest (e.g., viscosity). For example, the average count rate of the scattered light may be analyzed to determine polymer molecular mass (see for example PD2000/QELS manual, by Precision Detectors). Scattered light may be observed at multiple angles by using more than one fiber optics cable placed at different angles in the fiber optics probe. Alternative methods for submicroscopic particle sizing may also be employed, e.g., by measuring the Idegree of coherence of the scattered field (see U.S. Pat. Nos. 5,627,642 and 5,815,611, both of which are hereby incorporated by reference herein for all purposes), which circumvents the need for digital autocorrelation. In embodiments where a plurality (e.g., four or more) samples are being analyzed in parallel, the light scattered from the simultaneously illuminated samples can be detected serially (i.e., sequentially) or in parallel (i.e., simultaneously). The scattered light is preferably detected simultaneously, using a dedicated detection fiber for each illuminating fiber. In a serial (i.e., sequential) detection embodiment, however, a plurality of samples can be simultaneously illuminated over a period of time, and then within that period of time, light scattered from each of the plurality of samples can be detected with one or more detection fibers/detection probes (e.g., by translating a single detection probe, or by multiplexing the signal from a plurality of detection probes). In any case, the processing of the detected signal can also be effected serially (i.e., sequentially) or in parallel (i.e., simultaneously). For example, a multiple of data acquisition boards and/or correlators may be used to process the incoming electrical signals simultaneously (i.e., in parallel). Suitable detectors and detection techniques are described in greater detail below.

Figure 4C:
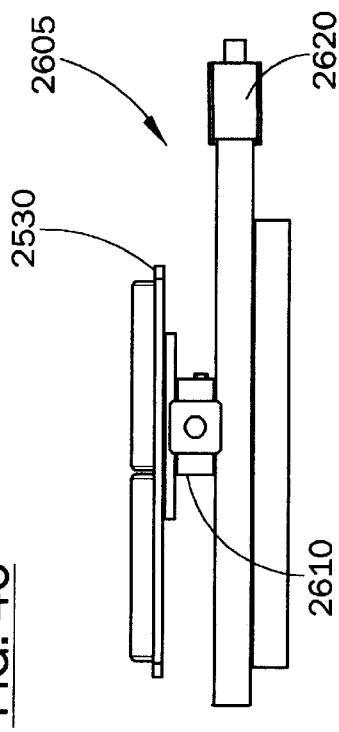
FIGS. 4A through 4C are schematic orthographic diagrams illustrating the sample holders, sample support surface (sample mount), and translation station shown in FIGS. 3A and 3B.
Figure 4A:
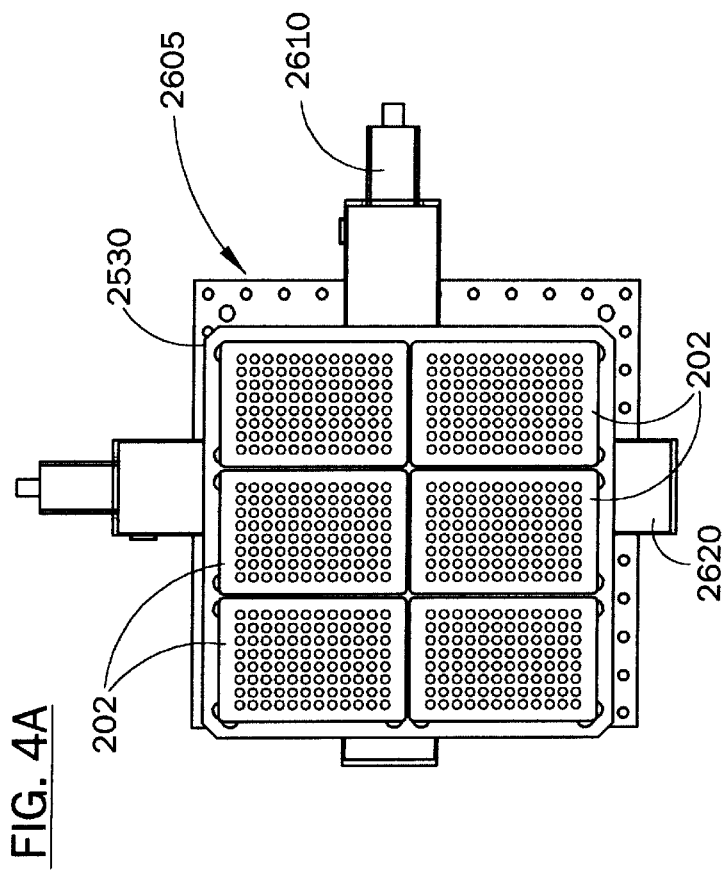
Figure 4B:
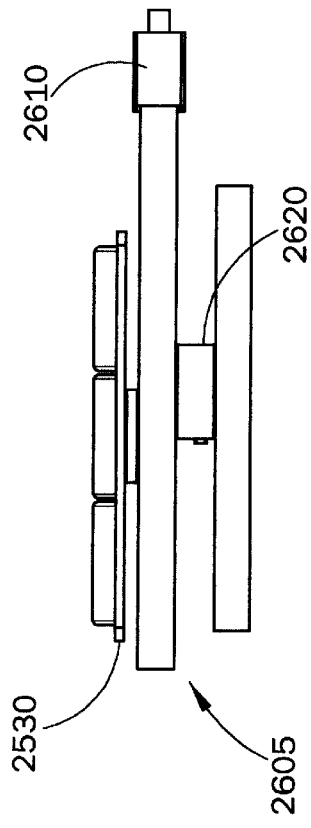

With reference to FIGS. 3A and 3B, and to FIGS. 4A through 4C, the sample holder(s) 202 and/or the probe head 2500 comprising the array of two or more fiber optic probes 420, 420' are adapted for relative translation with respect to each other. Such translation can be effected, for example, after analyzing the first plurality of the four or more samples. Hence, the apparatus of the invention can comprise a structure for a relative motion of the fiber optics probe(s) and one or more sample volumes, such structure being referred to herein as a translation station. In the figures, translation station 2605 can adapted for translating the sample holder(s) 202 or the probe head 2500 relative to each other, either directly or indirectly (e.g., via sample holder support mount 2530). In preferred embodiments, the translation station 2605 is adapted to translate the sample holder 202 in a plane that is substantially parallel to a plane defined by the array of fiber optic probes 420, 420'. Additionally or alternatively, the translation station 2605 can be adapted to translate the probe head 2500 in a plane that is substantially parallel to a plane definedd by the samples (20, FIG. 2). Hence, the translation station 2605 can comprise one or more translation stages 2610, 2620. Moreover, the translation station can be further adapted to translate the sample holder(s) 202 or the probe head in a plane that is substantially normal a plane substantially defined by the samples. In some embodiments (e.g., where the two or more probes corresponds to the number of samples in one directional orientation—such as a 1×8 array of probes for characterizing an 8×12 array of samples), relative motion may only be required in one direction (e.g., x-direction only) or in two directions (e.g., x-direction and z-direction). In any case, relative motion can be achieved preferably by a motorized precision translation stage or a combination of several translation stages. More specifically, the head and/or samples or sample holders can be mounted on computer driven stepping motor XYZ translation stages to achieve measurement (and data processing) of the entire array of samples in a fully automated fashion. The XY translation station can allow for translation of the individual wells of the microtiter plate. This motion may also extend over several microtiter plates. With reference again to FIGS. 3A and 3B, and FIGS. 4A through 4C, the sample mount 2530 can be mechanically fastened or be integral with an X-direction translation stage 2610 as well as a Y-direction translation stage 2620. The Z translation stage 2615 can accommodate different types of microtiter plates and probing scattering volumes at different heights in the samples. Vertical translation may be particularly useful if the fiber optics probes are immersed into the sample vials. By translating the scattering volume along different heights, inhomogeneities in the sample may be characterized (e.g. to observe sedimentation). Translating the sample holder(s) as opposed to the fiber optics probe(s) can be advantageous, in some embodiments, with respect to preventing possible strain and damage of the optical fibers and contamination by particulates from the translation stages.

Hence, a light-scattering sub-system can be defined, including one or more sample holders, one or more fiber optic light-scattering probes (preferably an array of light-scattering probes arranged on a probe head), and translation station, together with optional liquid samples, additional sample holders and common sample support (mount). The light scattering sub-system, or components thereof, may be enclosed to provide temperature control and/or other environmental control during characterization.

Following translation of the single probe (serial embodiment) or the array of probes (serial-parallel embodiment) and/or the sample holder(s), a second plurality of the four or more samples is then analyzed (in parallel for the serial-parallel embodiment). The second plurality of samples can be analyzed substantially as described above in connection with analysis of the first plurality of samples—by light scattering methods that include transmitting light from a fiber optic probe into a second sample (rapid-serial embodiment) or simultaneously transmitting from each of two or more fiber optic probes 420, 420' (FIG. 2, FIG. 3A, FIG. 3B) into a second plurality of samples (serial-parallel embodiment), and in either case, allowed to interact with the sample(s) in a sample volume, and by subsequently detecting the scattered light from the sample volume (serial embodiment) or from the plurality of sample volumes (serial-parallel embodiment)—sequentially or simultaneously.

One or more properties of the sample(s) being characterized or of components thereof can be determined from the detected scattered light according to methods known in the art. In the serial embodiment, the at least one property of each sample is preferably determined serially, in the order illuminated. In a serial-parallel embodiment (or a true parallel embodiment), the at least one property of each of the plurality of samples (or, in some embodiments the four or more samples) can be determined in series (i.e., as part of a hybrid serial-parallel approach) and/or can be determined in parallel. For example, commercially available autocorrelation instruments/software is available with up to eight channels in parallel. (e.g., ALV, Id.) The determined properties of interest can vary depending on the particular research goals. In preferred applications, the determined properties can include particle size, colloidal size, particle size distribution, concentration, molecular weight, molecular weight distribution, diffusion coefficient, viscosity, sample stability (e.g., over time, versus temperature, etc.), colloidal growth, crystal growth, changes in colloidal state versus experimental conditions (e.g., temperature, cosolvents, etc.).

In some applications, such as applications directed to combinatorial (i.e., high-throughput) materials research, the determined properties of the plurality of samples (or of four or more samples) can be compared to each other for relative evaluation of the samples. Significantly, such comparison can be effected using software and/or graphical interfaces to provide a consistent, throughput-integrated workflow. Software for effecting such comparison of such data can be purchased, for example, from Symyx Technologies, Inc. (Santa Clara, Calif.).

Parallel Embodiment

In a preferred parallel embodiment for characterizing a plurality of samples, each of a predefined set of samples (e.g., each of the two or more samples included within a single sample holder) are simultaneously characterized. In general, a plurality of samples, and preferably four or more samples can be provided. The samples are preferably a combinatorial library of liquid samples that comprises four or more different liquid samples (e.g., differing with respect to molecular weight, hydrodynamic radius, radius of gyration, or other property that can be determined using the techniques described herein). At least a plurality of samples, and preferably at least four of four or more samples are analyzed in parallel by light scattering methods that include simultaneously transmitting light into the at least four samples of the library, and simultaneously detecting light scattered from the at least four samples of the library or components thereof. Preferably, one or more properties of the plurality or of the at least four samples (e.g., of the library) or of components thereof is determined, serially or simultaneously. The determined property of each of the plurality or the at least four samples can then be compared, as described.

In a preferred embodiment for parallel characterization of four or more liquid samples, the four or more samples are provided in a sample holder and analyzed using an array of four or more fiber optic probes. The array of fiber optic probes is preferably arranged in a probe head to correspond to the arrangement of samples in the sample holder. The number of probes and the spatial arrangement of probes included in the array of light-scattering probes can correspond to the number and spatial arrangement of samples included in a sample holder. Hence, in such embodiment, all of the samples included within the predefined set of samples can be characterized using light-scattering in parallel. If multiple sample holders are staged on a common mount, then a translation station can be used to effect relative motion between the mount and the array of fiber optic probes, such that a first set of samples (in a first sample holder) can be characterized in parallel using the array of light-scattering probes, the mount and/or the array of probes can then be translated relative to each other, and thereafter, a second set of samples (in a second sample holder) can be characterized in parallel using the array of light-scattering probes. If the probes are immersion probes, then the probes can be washed or otherwise freed from impurities between analysis runs. Further details regarding immersion probes are discussed below.

Relative Orientation of Sample Holders versus Array of Fiber Optic Probes

In particularly preferred embodiments, the light scattering subsystem apparatus comprises a sample holder adapted to present the plurality of liquid samples (preferably an array of four or more liquid samples) and preferably in a substantially coplanar relationship to each other. The plurality of samples are preferably presented with each sample comprising an exposed gas-liquid interface (described in greater detail below). The subsystem apparatus further comprises an array of two or more fiber optic probes, preferably four or more fiber optic probes, arranged (e.g. with a probe head) to spatially correspond to the array of samples or to a subset thereof (the subset including samples on the same sample holder, or on different sample holders). The two or more fiber optic probes are adapted to simultaneously illuminate a liquid sample for analysis by light scattering. The two or more fiber optic probes can be further adapted to simultaneously detect light scattered from the plurality of liquid samples or a component thereof. The subsystem apparatus can further comprise a translation station for translating the sample holder or the probe head relative to each other.

In a preferred embodiment, the sample holder is adapted to present the four or more samples in a substantially coplanar relationship to each other, and the probe head comprises the two or more fiber optic probes in a substantially coplanar relationship to each other. The translation station is adapted to translate the sample holder or the probe head in a plane that is substantially parallel to the plane defined by the array of fiber optic probes or the samples, respectively. The translation station can be alternatively, and/or further adapted to translate the sample holder or the probe head in a direction that is substantially normal to the plane defined by the samples.

In another preferred embodiment, the probe head is positionable over the sample holder such that the array of fiber optic probes can simultaneously illuminate two or more of the liquid samples from above the plane comprising the samples. Preferably, in this embodiment, each of the two or more fiber optic probes are further adapted to simultaneously detect light scattered from the plurality of liquid samples or a component thereof. An advantage of having the detecting fiber likewise mounted above the samples is that possible precipitates at the bottom of the well would not substantially interfere with the pathway of the scattered light.

In a variation of the immediatly-preceding embodiment, the subsystem apparatus can further comprise a second probe head that comprises a second array of two or more fiber optic probes, preferably four or more fiber optic probes, arranged to correspond to the array of samples or a subset thereof. The second probe head can be positionable under the sample holder such that the second array of two or more fiber optic probes can simultaneously detect light scattered from the plurality of liquid samples or a component thereof.

Alternatively, the incident light can be transmitted into the scattering volume of the sample from the array of fiber optic probes positioned underneath the sample holder and/or the scattered light can be detected by the array of fiber optic probes positioned above (over) the sample holder.

The aforementioned preferred embodiments can be effective with non-immersion probes and/or with immersion probes (discussed below). If an immersion probe is effected, the subsystem can also include a washing station for simultaneously washing each of the two or more fiber optic probes to reduce contamination from samples into which the probes were immersed.

Illumination and/or Detection through Gas-Liquid Interface (Non-Immersion Probes)

In a preferred, non-immersion embodiment for characterizing one or more liquid samples or a components thereof, a liquid sample having an exposed surface that defines a gas-liquid sample interface is provided. The sample is analyzed by light-scattering methods that include transmitting light through the gas-liquid sample interface into the sample, and detecting light scattered from the sample or a component thereof. The sample can be alternatively analyzed by light-scattering methods that include transmitting light into the sample, and detecting light scattered from the sample or a component thereof through the gas-liquid sample interface. In a firther approach, both the illumination and the detection can be effected through the gas-liquid sample interface. Regardless of the particular approach, this embodiment—with illumination and/or detection being effected through the gas-liquid interface—can be effected in any suitable configuration, including for example, in configurations established for serial, serial-parallel and parallel modes of operation, discussed in detail above.

The exposed surface of the liquid sample defines a gas-liquid sample interface. The exposed surface can be within a fully enclosed container, or can be within an open-top container. Open-top containers present particular advantages with respect to optics. The exact shape of the gas-liquid interface is generally not narrowly critical. In preferred embodiments, however, the gas-liquid interface is preferably non-spherical, and more preferably non-curved—at least in the region(s) through which light is transmitted and/or detected. In a particularly preferred embodiment, the shape of the gas-liquid sample interface is substantially planar in the region through which the incident light is transmitted and/or through which the scattered light is detected. The gas-liquid interface can also be substantially planar across substantially the entire surface of the gas-liquid interface. For some embodiments, the gas-liquid interface can be characterized with respect to relative scattering angles. That is, the shape of the gas-liquid interface can be controlled such that a difference in scattering angle of not more than about 10°, and preferably not more than about 5°, results relative to the scattering angle from a perfectly planar gas-liquid interface. In other embodiments, the gas-liquid interface can be characterized with respect to relative values of determined properties. In general, the shape of the gas-liquid interface can be controlled such that the difference in the value of the determined property (e.g., hydrodynamic radius) is not more than about 30%, preferably not more than about 15%, more preferably not more than about 10% and most preferably not more than about 5% relative to the value of a determined property using a perfectly planar gas-liquid interface.

A preferred gas-liquid interface—e.g., having a non-curved, non-spherical and preferably substantially parallel shape—can be achieved by any suitable manner.

Figure 9A:
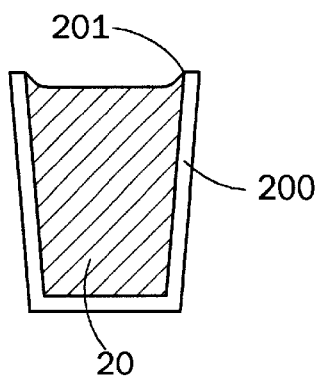
FIGS. 9A through 9D are schematic diagrams illustrating various embodiments of a sample container (e.g. vessel) comprising a liquid sample.
Figure 9B:
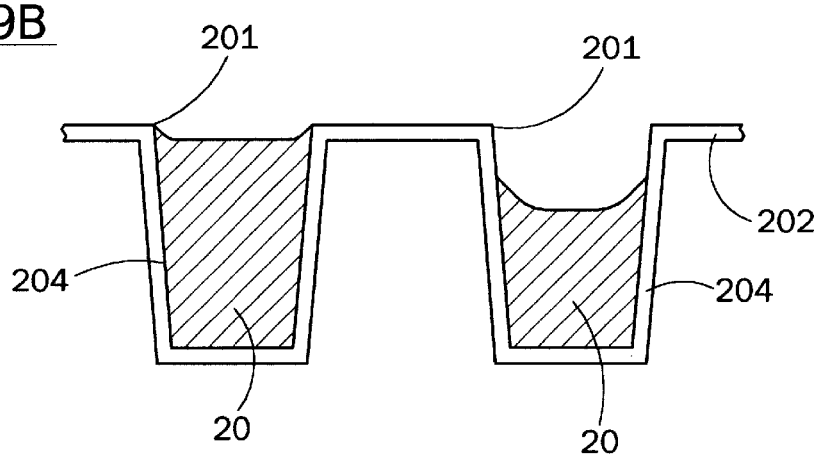

According to one approach, with reference to FIG. 9A, a sample 20 can be contained in an open top vessel 200. In general, the open top vessel 200 defines a cavity having an upper edge 201. With reference to FIG. 9B, a plurality of samples can be contained in a plurality of open-top vessels, such as wells 204 of a sample holder 202 (e.g., a microtiter plate). Regardless of the particular configuration that defines the open-top vessel 200, the vessel 200 can be filled with the liquid sample 20 substantially to the upper edge 201 of the cavity. Without being bound by theory, as shown in FIGS. 9A and 9B, filling the vessel 200 to the upper edge 201 of the cavity will change the effect of surface tension of the liquid sample 20 with respect to the vessel 200, and can cause the gas-liquid interface to become non-spherical, non-curved and/or substantially planar. In general, the shape of the meniscus approaches planarity as the level of liquid sample in the vessel nears the opentop. Overfilling the vials can give rise to a convex shaped gas-liquid (e.g., air-liquid) interface. For optical reasons, it is preferable that the meniscus be as close to planar as practical. Therefore, it is preferable to fill the vials such that the liquid level is flush with the rim of the individual vials, although slight deviations towards a positive or negative meniscus are tolerated. Open-top vessels are particularly effective for use in connection with liquid samples comprising non-volatile or only slightly volatile liquids (e.g., solvents or other liquid-phase). Such non-evaporating or slowly-evaporating liquids (e.g. water) allow for measurement of sample properties directly though the liquid/air (more generically liquid/gas) meniscus of the sample containers without transmitting the incident light and/or detecting the scattered light through a cover. With such samples, it is also not generally necessary to seal the container, and as such, it is not generally necessary to use an optical contact probe designed to analyze the samples through the side wall(s) of a cuvette (curved vessel). In addition to not having to cover the vessel(s), index-matching fluids are likewise not required to prevent excessive reflection at interfaces.

Figure 9C:
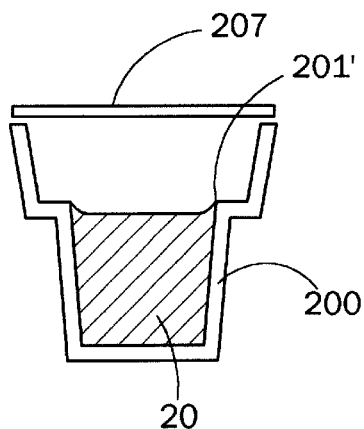
Figure 9D:
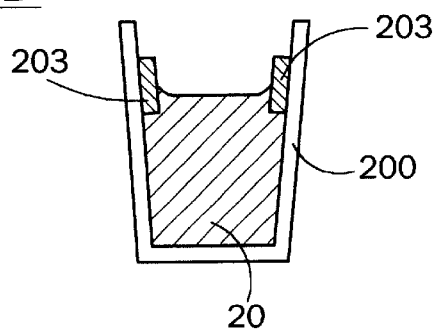

Other approaches also exist, however, for achieving the preferred shape of the gas-liquid surface interface. With reference to FIG. 9C, for example, a non-spherical, non-curved and/or substantially planar shape can be achieved using other approaches for controlling the surface tension and/or contact angle of the liquid sample 20 with respect to the vessel 200—such as having an intermediate ledge 201' and filling the vessel 200 with liquid sample 20 substantially to the intermediate ledge 201'. Notably, the vessel 200 of FIG. 9C could be a closed-top vessel having a cover 207 transparent to the illuminating and/or scattered light transmitted and/or detected through the gas-liquid sample interface, respectively. Such covered vessels—wholly covered (e.g. closed-top vessels 207) or partially covered (not shown) may be particularly advantageous with respect to preventing evaporation of more volatile liquid samples (e.g., solvents or other liquid phase). As another exemplary approach for achieving a non-spherical, a non-curved and/or substantially planar gas-liquid sample interface, with reference to FIG. 9D, a coating 203 can be formed on an interior surface of the vessel 200, with the vessel 200 filled with liquid sample 20 substantially to contact the coating 203 along the periphery of the vessel. The coating 203 can modify the surface properties along the wetted perimeter of the vessel 200 such that the meniscus is substantially planar in the region through which light is transmitted or detected.

In the embodiment in which the sample is analyzed by transmitting the incident light through the gas-liquid sample interface into the sample, the scattered light can be detected through the gas-liquid sample interface, or alternatively through the side or bottom of the container. In the latter case, the side or bottom of the container is preferably sufficiently transparent to the scattered light to allow for detection.

In a rapid-serial approach for characterizing a plurality of samples, first and second liquid samples, each having an exposed surface that defines a gas-liquid interface, can be sequentially analyzed by such light scattering methods. Specifically, light can be transmitted through the gas-liquid sample interface of the first sample into the first sample. The incident light can be scattered by the first sample or a component thereof in a first scattering volume within the sample, and the light scattered from the second sample can then be detected, preferably through the gas-liquid interface, but alternatively through a side or bottom of a container or vessel. The second liquid sample can then be analyzed by transmitting light through the gas-liquid sample interface of the second sample into the second sample, allowing the incident light to be scattered by the second sample or a component thereof in a second scattering volume within the sample, and detecting the light scattered from the second sample, preferably through the gas-liquid interface, but alternatively through a side or bottom of a container or vessel.

In a parallel approach for characterizing a plurality of samples—each having an exposed surface that defines a gas liquid interface—the plurality of liquid samples are analyzed in parallel by light scattering methods that include simultaneously transmitting incident light through the gas-liquid sample interface into the plurality of samples, allowing the incident light to be scattered by the samples or by components thereof, and detecting scattered light—preferably through the gas-sample interface of each of the plurality of samples, or alternatively through the sides and or bottom of containers or vessels comprising the plurality of liquid samples.

Serial-parallel approaches can likewise be effected using such light-scattering approaches, substantially as described above.

The non-immersion embodiment for characterizing a plurality of samples—through a gas-liquid sample interface—can be implemented, for example, using one or more of the aforedescribed light-scattering subsystem embodiments. Specifically, these methods can be effected with light-scattering sub-systems comprising sample holders and an array of two or more fiber optic probes, preferably mounted on a probe head. The sub-system can also include translation stations or other components, as described.

Immersion Probes

In a further embodiment of the invention, the light-scattering probe(s) can be immersion probes, each of the immersion probes comprising one or more immersion tip (e.g., a transmitting immersion tip and/or a receiving immersion tip). The immersion probe can be effectively employed alone and/or in combination with the one or more of the aforedescribed light-scattering subsystem embodiments (e.g., comprising sample holders and an array of two or more fiber optic probes, preferably mounted on a probe head, optionally together with translation stations or other components, as described).

More specifically, the invention can include an immersion tip fiber optics probe for dynamic light scattering measurements and/or static light scattering measurements. The immersion tip fiber optic probe can include protective structure (e.g, optically acceptable films, coatings, covers, etc.) to physically shield the immersion tip. For example, if solvents or other liquid media affect the surface of the fiber optic probe, it may be advantageous to surround the immersion tip of the fiber optics probe with a protective glass housing, possibly with index matching fluid. Alternatively, the array of sample volumes may be probed from below, for example by using a sample holder with an optically transparent bottom.

Figure 7A:
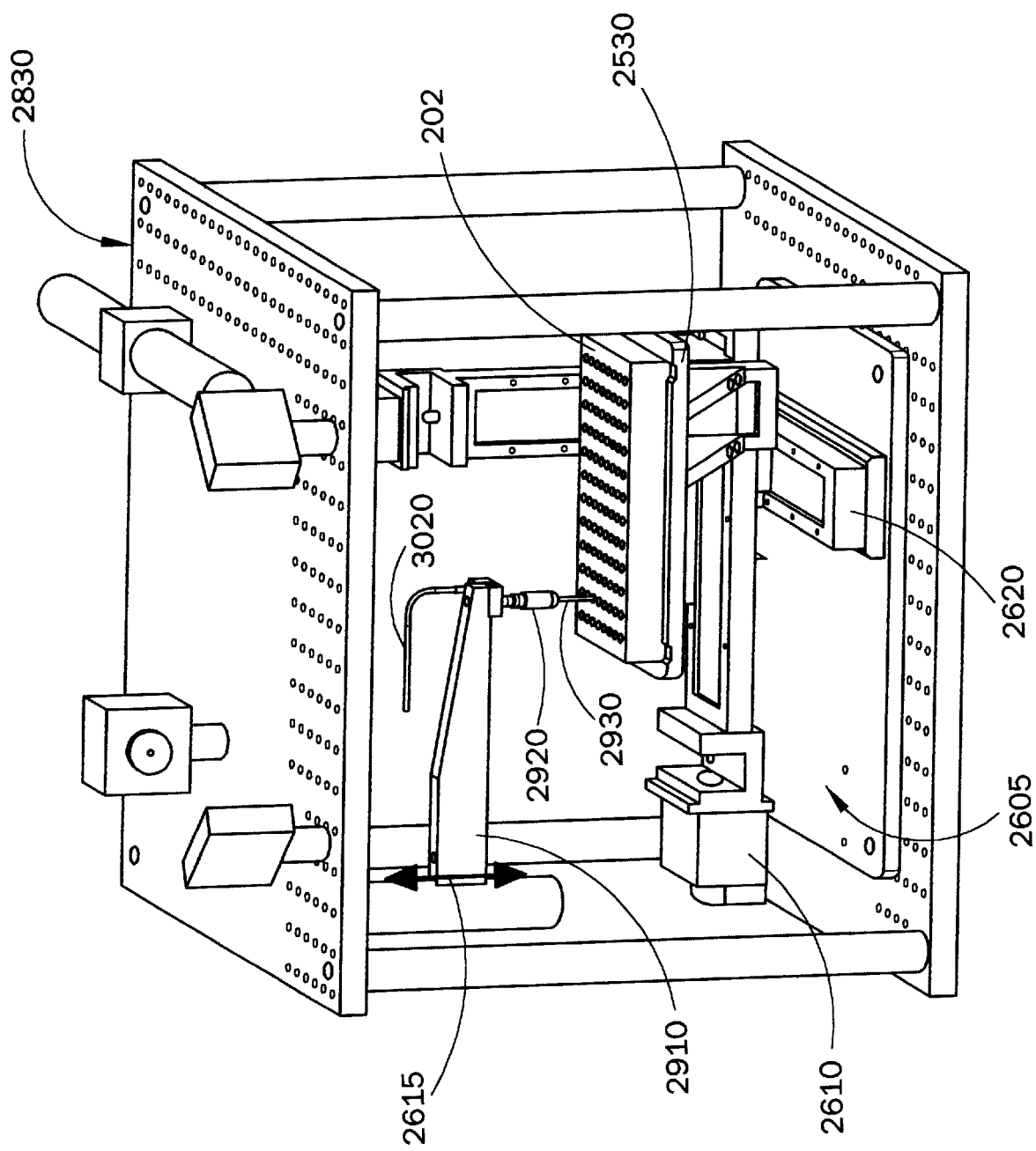
FIG. 7A is a schematic perspective diagram illustrating an embodiment of a dynamic light scattering apparatus comprising a probe head that includes an immersion probe, a sample holders, and a translation station for providing relative motion between the immersion probe and the sample holders.
Figure 8A:
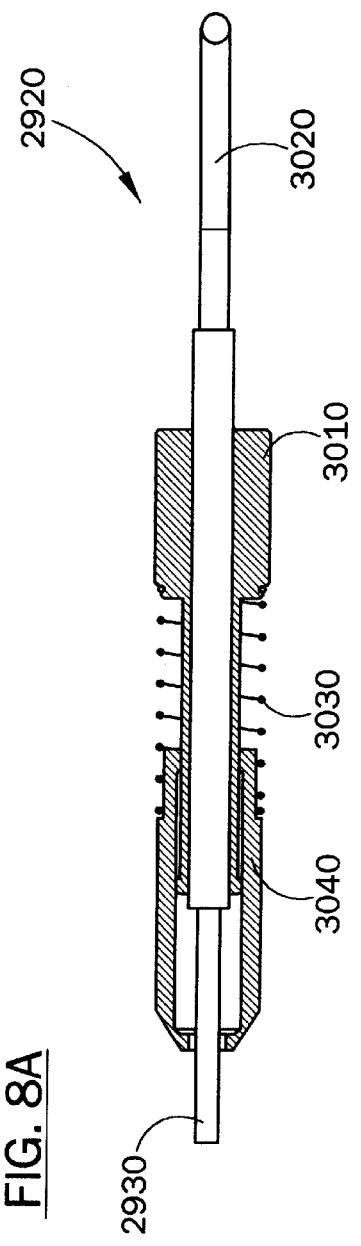
FIGS. 8A through 8C are schematic orthographic diagrams illustrating an immersion probe and immersion probe holder.
Figure 8B:
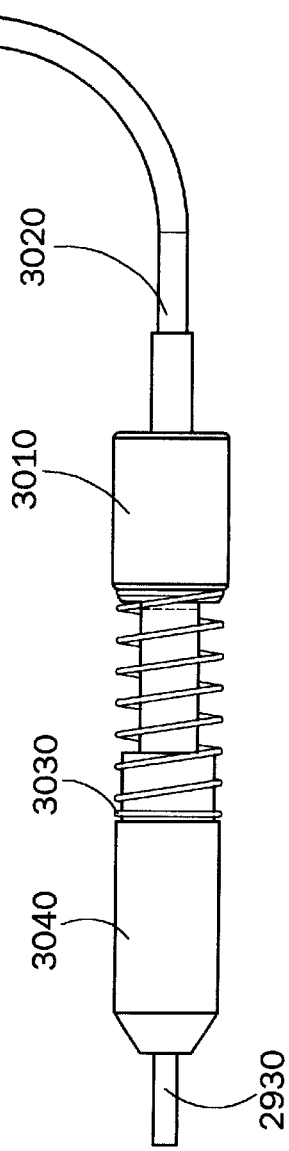
Figure 8C:
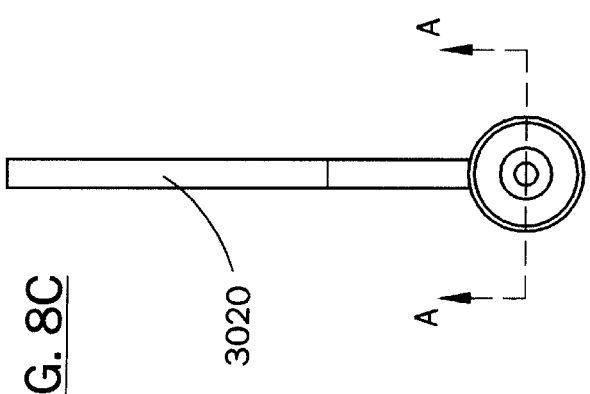

With reference to FIG. 7A, a light scattering probe head 2910 can include a fiber optic immersion probe holder 2920 and a fiber optic immersion probe 2930. A sample holder 202 (e.g., microtiter plate) can be positioned on a sample mount 2530. As described above in connection with the general description of the light-scattering subsystem of the invention, the sample holder 202 and/or probe head 2910 (comprising one or more immersion-probes) can be adapted for relative translation between each other. In particular, relative translation/motion can be provided as described, for example using one or more translation stages 2610, 2620. Vertical translation can also be provided (e.g., using vertical translation stage 2615). With reference as well to FIGS. 8A through 8C, the fiber optic immersion probe holder 2920 can include a fiber optic cable 3020 that passes through a DLS-010 optic guide RO 3010, a spring 3030 and a DLS-014 tip guard RO 3040. This sub-system can be modified to perform IR, UV, fluorescence, and/or Raman spectroscopy and/or to operate with non-immersion probe(s). Further details are known in the art. The immersion probe for light-scattering analysis can be, for example, an immersion probe such as disclosed in U.S. Pat. No. 5,011,279 to Auweter et al., which is hereby incorporated for reference for all purposes. See also Weise et al., *Fiber-Optic Quasielastic Light Scattering in Concentrated Latex Dispersions: The Performance of Single-Mode vs. Monomode Fibers*, Ber. Bunsenges. Phys. Chem., 96:12, 1818–1828 (1992). The invention can include other immersion fiber optics sensors such as for IR measurements (see e.g. Remspec Corporation), fluorescence measurements or Raman measurements.

The system can further comprise a wash station to remove possible sample contamination between measurements of different wells. In a preferred approach, each immersion probe included in the array of probes can be exposed to one or more agents for cleaning. Preferably, the cleansing process can include exposing the immersion tip to a first agent that is preferably a wash agent suitable for removing (e.g., dissolving) impurities from the immersion tip. The washing agent can be water, for example, for aqueous sample applications. The washed tip can be subsequently exposed to a second agent, such as a further wash agent or a rinsing agent. The rinsing agent is preferably a volatile solvent (e.g. alcohol). Following cleansing, the immersion tip is preferably dried to remove residual cleansing agent (i.e., wash agent or rinsing agent). Drying can be effected, for example, by evaporation in a flowing, optionally heated, stream of gas, preferably an inert gas.

Figure 7B:
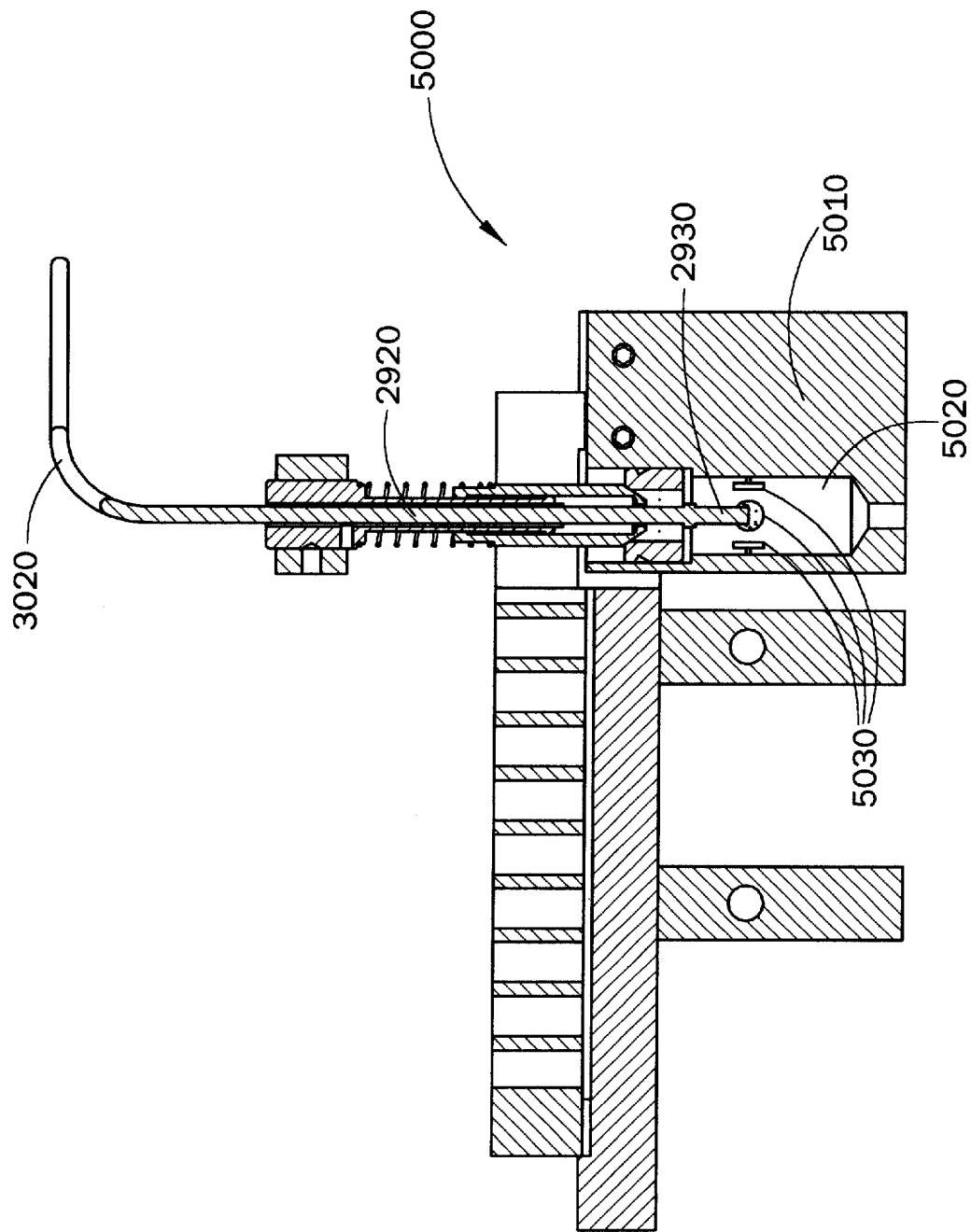
FIG. 7B is a schematic orthographic diagram illustrating a wash station suitable for use in connection with one or more immersion probes.

With reference to FIG. 7B, an immersion probe 2920 (or an array of such probes) can be cleaned between successive sample characterizations in a wash station 5000 comprising a docking station 5010 having a wash cavity 5020 adapted to receive the immersion tip 2930 of the immersion probe 2920. The wash cavity 5020 preferably comprises one or more, preferably two or more, and most preferably four or more nozzles 5030, with each of the one or more nozzles 5030 being in fluid communication with a cleansing agent source (e.g., wash agent, rinsing agent), with appropriate conduits and valving to allow for varying the cleansing agent.

Integrated Fiber-Optic Light-Scattering System

Figure 6:
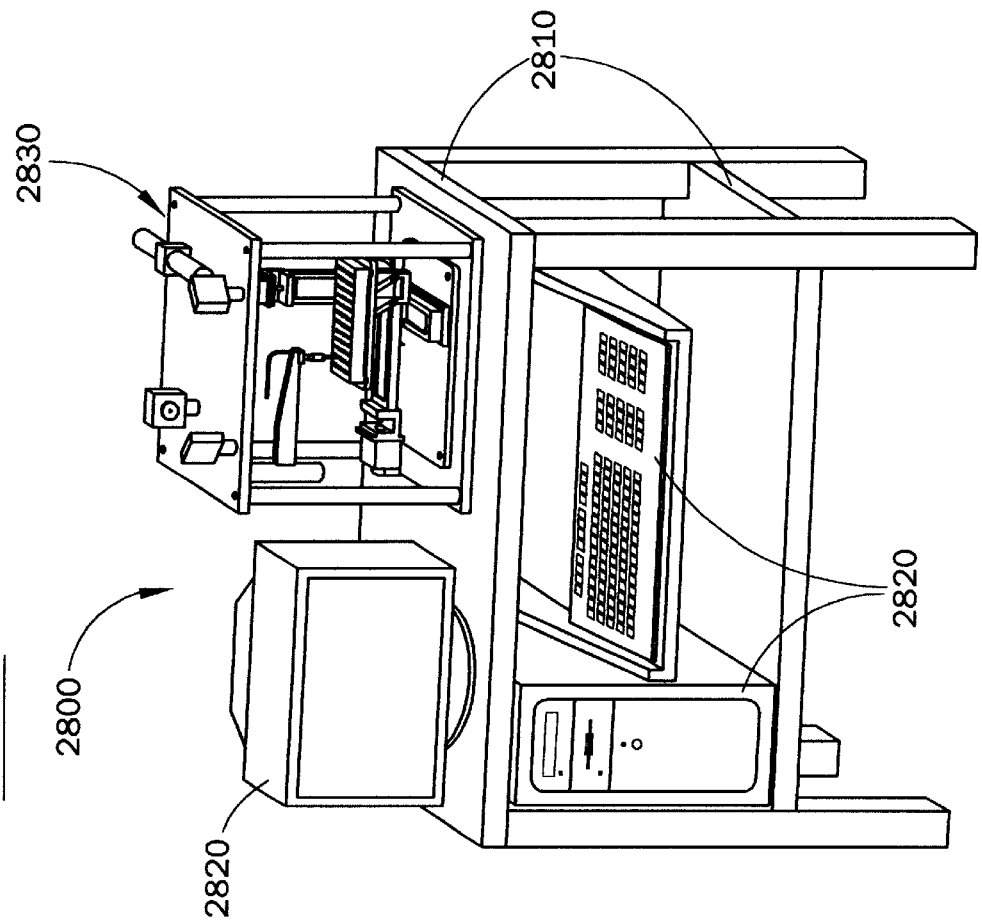
FIG. 6 is a high level schematic perspective diagram illustrating an integrated, turn-key light-scattering analysis system suitable for configuration with non-immersion or immersion light-scattering probes.

Referring to FIG. 6, an immersion and/or non-immersion fiber-optic light-scattering analysis system 2800 can comprise an immersion or non-immersion probe subsystem 2830 positioned on a rack 2810 or other means of support (e.g., table, etc), and a microprocessor 2820 (e.g., including microprocessing unit, graphic display and/or keyboard).

Samples

The liquid samples being characterized by the present invention are not critical. In general, and without limitation, the sample can be a solution, an emulsion, a dispersion and/or a suspension. Collodial dispersions or suspensions are particularly preferred samples in some embodiments. The samples can be polymer samples (including non-biological polymers and biological polymers), or non-polymer samples. The samples can be substantially homogeneous or heterogeneous with respect to phase. The samples can likewise be homogeneous or heterogeneous with respect to molecular structure of components.

Preferably, the sample being characterized can generally include one or more components—typically in a solution, emulsion, dispersion or suspension (e.g. preferably uniform dispersed in a continuous phase)—with component particles ranging in diameter from about 1 nm to about 1000 nm, or from about 2 nm to about 500 nm, more typically from about 20 nm to about 400 nm, and even more typically from about 40 nm to about 200 nm.

The sample size (i.e., volume) is not critical, and can generally vary, depending on the particular characterization protocols and systems used to characterize the sample or components thereof. Typical sample sizes can range from about 0.1 $\mu$l to about 2 ml, or from about 0.1 $\mu$l to about 1 ml, more typically from about 1 $\mu$l to about 1000 $\mu$l, even more typically from about 5 $\mu$l to about 1000 $\mu$l, about 50 $\mu$l to about 700 $\mu$l, and still more typically from about 200 $\mu$l to about 400 $\mu$l.

The concentration can range is likewise not critical, and can generally vary from a detectable concentration level (for the particular detector employed) up to about 1 mg/ml, or more in some applications. Typical concentrations can be about $1\times10^{-2}$ wt %, about $1\times10^{-3}$ wt % or about $1\times10^{-4}$ wt %, and can generally range from about $1\times10^{-4}$ wt % to about 30 wt %, from about $1\times10^{-3}$ wt % to about 10 wt %, or from about $1\times10^{-2}$ wt % to about 1 wt %.

Further details regarding various samples, and arrays of samples are discussed as follows.

Colloidal Samples

The samples being characterized according to the present invention can be colloidal systems comprising polymer and/or non-polymer components. Colloidal systems consist of small particles (typical size range of 1–1000 nm) that are uniformly and discontinuously distributed in another continuous phase. Colloidal dispersions are characterized by the solute molecules or particles (disperse phase) being much larger than the solvent or continuous (dispersion) phase. Gels are another type of colloidal systems that represent bicontinuous structures of solid and liquid phases. More complicated systems with more than two phases may also exist that may also include stabilizing agents, e.g. suspensions and emulsions during an emulsion polymerization. In contrast, both the solute molecules and the solvent are of the same dimension in "true" solutions (typically less than a few nanometers).

The particular nature of the colloidal systems is not critical. In one such system, the dimension of the solute molecule is much larger than the size of the solvent molecules. Examples of these types of systems include proteins, polysaccharides, and other polymeric molecules. In another such colloidal system, a large number of small solute molecules aggregate into association colloids. Examples of these types include micelles (detergents) and vesicles. In a further such colloidal system, small particles of insoluble molecule are dispersed in a particular liquid phase, often in conjunction with a stabilizing agent. Examples of this type include clay minerals in water or silver chloride crystals.

In most two-phase colloidal systems the solvent phase is liquid, with the disperse phase being solid (forming a suspension, sol or slurry), liquid (forming an emulsion) or gaseous (forming a foam). Systems in which the solvent phase is liquid are sometimes also called complex fluids. If the dispersion medium is solid, the colloidal system is referred to as a solid dispersion, solid emulsion or solid foam for the disperse phase being solid, liquid or gas, respectively. Solids or liquids dispersed in a gas phase are known as aerosols. Colloidal phases such as suspensions and emulsions are particularly commercially significant.

Nanodispersion Formulations Samples

In additional preferred applications, the polymer sample can be a sample to be used in, or a sample resulting from, a dispersion and/or formulation process. A library comprising diverse formulation samples can be formed, for example, by applying combinatorial experimental approaches to nano-disperion formulation techniques. For example, a nanodispersant formulation sample, or a library of nanodispersant formulation samples can be characterized according to the present invention (e.g., for stability analyses).

Hence, the sample can be a nanodispersion formulation, can consist essentially of a nanodispersant, or can comprise a nanodispersant—including a polymeric nanodispersant and/or a non-polymeric nanodispersant. Such nanodispersants can be typically employed, for example, in nanodispersion systems comprising the nanodispersant, an application media (e.g, liquid phase media, such as water, for the dispersion system), and one or more active ingredients (typically, an ingredient such as a pharmaceutical, crop protection agent, vitamins, dye stuffs, organic pigments, inorganic pigments, catalysts, enzymes, fillers, stabilizers, etc. that is poorly soluble, by itself, in the application media).

Polymeric nanodispersant sample can be selected from the group consisting of oligomers and low and high molecular weight polymers with a polymerization degree of more than 2. The polymeric nanodispersants can, for example, be selected from the group consisting of protective colloids, amphiphilic copolymers, thickeners. Said nanodispersants can be surface-active additives, which can be used to inhibit crystal growth and agglomeration. Specific (co)polymers which can act as nanodispersants include, for example, random copolymers of vinyl monomers, copolymers with controlled architecture/blocks, condensation polymers, etc. Preferably said nanodispersants are prepared by polymerization of at least 2 monomers A and B, selected from the group consisting of hydrophobic, neutral hydrophilic, cationic and anionic monomers. Preferably, one of said monomers is a hydrophilic monomer and a second monomer is a hydrophobic monomer. The polymeric nanodispersant is preferably effective for dispersing the active ingredient in the application media without visually observable macroscopic phase separation. Further details regarding polymer samples are described below.

The non-polymeric nanodispersant can be an element or non-polymeric compound compatible with both the active ingredient and the application media, and effective for dispersing the active ingredient in the application media without visually observable macroscopic phase separation.

Polymer Samples

The polymer sample can be a homogeneous polymer sample or a heterogeneous polymer sample, and in either case, comprises one or more polymer components. As used herein, the term "polymer component" refers to a sample component that includes one or more polymer molecules. The polymer molecules in a particular polymer component have the same repeat unit, and can be structurally identical to each other or structurally different from each other. For example, a polymer component may comprise a number of different molecules, with each molecule having the same repeat unit, but with a number of molecules having different molecular weights from each other (e.g., due to a different degree of polymerization). As another example, a heterogeneous mixture of copolymer molecules may, in some cases, be included within a single polymer component (e.g., a copolymer with a regularly-occurring repeat unit), or may, in other cases, define two or more different polymer components (e.g., a copolymer with irregularly-occurring or randomly-occurring repeat units). Hence, different polymer components include polymer molecules having different repeat units. It is possible that a particular polymer sample (e.g., a member of a library) will not contain a particular polymer molecule or polymer component of interest.

The polymer molecule of the polymer component is preferably a non-biological polymer. A non-biological polymer is, for purposes herein, a polymer other than an amino-acid polymer (e.g., protein) or a nucleic acid polymer (e.g., deoxyribonucleic acid (DNA)). The non-biological polymer molecule of the polymer component is, however, not generally critical; that is, the systems and methods disclosed herein will have broad application with respect to the type (e.g., architecture, composition, synthesis method or mechanism) and/or nature (e.g., physical state, form, attributes) of the non-biological polymer. Hence, the polymer molecule can be, with respect to homopolymer or copolymer architecture, a linear polymer, a branched polymer (e.g., short-chain branched, long-chained branched, hyper-branched), a cross-linked polymer, a cyclic polymer or a dendritic polymer. A copolymer molecule can be a random copolymer molecule, a block copolymer molecule (e.g., di-block, tri-block, multi-block, taper-block), a graft copolymer molecule or a comb copolymer molecule. The particular composition of the non-biological polymer molecule is not critical, and can include repeat units or random occurrences of one or more of the following, without limitation: polyethylene, polypropylene, polystyrene, polyolefin, polyimide, polyisobutylene, polyacrylonitrile, poly(vinyl chloride), poly(methyl methacrylate), poly(vinyl acetate), poly(vinylidene chloride), polytetrafluoroethylene, polyisoprene, polyacrylamide, polyacrylic acid, polyacrylate, poly(ethylene oxide), poly(ethyleneimine), polyamide, polyester, polyurethane, polysiloxane, polyether, polyphosphazine, polymethacrylate, and polyacetals. Polysaccharides are also preferably included within the scope of non-biological polymers. While some polysaccharides are of biological significance, many polysaccharides, and particularly semi-synthetic polysaccharides have substantial industrial utility with little, if any biological significance. Exemplary naturally-occurring polysaccharides include cellulose, dextran, gums (e.g., guar gum, locust bean gum, tamarind xyloglucan, pullulan), and other naturally-occurring biomass. Exemplary semi-synthetic polysaccharides having industrial applications include cellulose diacetate, cellulose triacetate, acylated cellulose, carboxymethyl cellulose and hydroxypropyl cellulose. In any case, such naturally-occurring and semi-synthetic polysaccharides can be modified by reactions such as hydrolysis, esterification, alkylation, or by other reactions.

In typical applications, a polymer sample is a heterogeneous sample comprising one or more polymer components, one or more monomer components and/or a continuous fluid phase. In copolymer applications, the polymer sample can comprise one or more copolymers, a first comonomer, a second comonomer, additional comonomers, and/or a continuous fluid phase. The polymer samples can, in any case, also include other components, such as catalysts, catalyst precursors (e.g., ligands, metal-precursors), solvents, initiators, additives, products of undesired side-reactions (e.g., polymer gel, or undesired homopolymer or copolymers) and/or impurities. Typical additives include, for example, surfactants, control agents, plasticizers, cosolvents and/or accelerators, among others. The various components of the heterogeneous polymer sample can be uniformly or non-uniformly dispersed in the continuous fluid phase.

The polymer sample is preferably a liquid polymer sample, such as a polymer solution, a polymer emulsion, a polymer dispersion, a polymer suspension (including, for example, colloidal solutions, dispersions or suspensions) or a polymer that is liquid in the pure state (i.e., a neat polymer). A polymer solution comprises one or more polymer components dissolved in a solvent. The polymer solution can be of a form that includes well-dissolved chains and/or dissolved aggregated micelles. The solvent can vary, depending on the application, for example with respect to polarity, volatility, stability, and/or inertness or reactivity. Typical solvents include, for example, tetrahydrofuran (THF), toluene, hexane, ethers, trichlorobenzene, dichlorobenzene, dimethylformamide, water, aqueous buffers, alcohols, etc. According to traditional chemistry conventions, a polymer emulsion can be considered to comprise one or more liquid-phase polymer components emulsified (uniformly or non-uniformly) in a liquid continuous phase, and a polymer dispersion can be considered to comprise solid particles of one or more polymer components dispersed (uniformly or non-uniformly) in a liquid continuous phase. The polymer emulsion and the polymer dispersion can also be considered, however, to have the more typically employed meanings specific to the art of polymer science—of being a emulsion-polymerization product and dispersion-polymerization product, respectively. In such cases, for example, the emulsion polymer sample can more generally include one or more polymer components that are insoluble, but uniformly dispersed, in a continuous phase, with typical emulsions including polymer component particles ranging in diameter from about 2 nm to about 500 nm, more typically from about 20 nm to about 400 nm, and even more typically from about 40 nm to about 200 nm. The dispersion polymer sample can, in such cases, generally include polymer component particles that are dispersed (uniformly or nonuniformly) in a continuous phase, with typical particles having a diameter ranging from about 0.2 nm to about 1000 $\mu$m, more typically from about 0.4 $\mu$m to about 500 $\mu$m, and even more typically from about 0.5 $\mu$m to about 200 $\mu$m. The polymer sample be a polymer suspension comprising uniformly dispersed polymer components. Additionally, the polymer sample can be a colloidal solution, dispersion and/or suspension. Colloidal solutions, dispersions and suspensions of the invention can have components with particle sizes ranging, for example, from about 1 nm to about 1000 nm, from about 1 nm to about 700 nm, from about 1 nm to about 500 nm, from about 1 nm to about 400 nm, from about 1 nm to about 200 nm, and from about 1 nm to about 100 nm. Exemplary polymers that can be in the form of neat polymer samples include dendrimers, and siloxane, among others. The liquid polymer sample can also be employed in the form of a slurry, a latex, a microgel a physical gel, or in any other form sufficiently tractable for analysis as described and claimed herein. Liquid samples are useful in the automated sample-handling tools that prepare and automatically sample each member of a polymer library. Liquid samples also allow the sample to flow in the chromatographic system or characterization system. In some cases, polymer synthesis reactions (i.e., polymerizations) directly produce liquid samples. These may be bulk liquid polymers, polymer solutions, or heterogeneous liquid samples such as polymer emulsions, latices, or dispersions. In other cases, the polymer may be synthesized, stored or otherwise available for characterization in a non-liquid physical state, such as a solid state (e.g., crystalline, semi-crystalline or amorphous), a glassy state or rubbery state. Hence, the polymer sample may need to be dissolved, dispersed or emulsified to form a liquid sample by addition of a continuous liquid-phase such as a solvent. The polymer sample can, regardless of its particular form, have various attributes, including variations with respect to polarity, solubility and/or miscibility.

In preferred applications, the polymer sample is a polymerization product mixture. As used herein, the term "polymerization product mixture" refers to a mixture of sample components obtained as a product from a polymerization reaction. An exemplary polymerization product mixture can be a sample from a combinatorial library prepared by polymerization reactions, or can be a polymer sample drawn off of an industrial process line. In general, the polymer sample may be obtained after the synthesis reaction is stopped or completed or during the course of the polymerization reaction. Alternatively, samples of each polymerization reaction can be taken and placed into an intermediate array of vessels at various times during the course of the synthesis, optionally with addition of more solvent or other reagents to arrest the synthesis reaction or prepare the samples for analysis. These intermediate arrays can then be characterized at any time without interrupting the synthesis reaction. It is also possible to use polymer samples or libraries of polymer samples that were prepared previously and stored. Typically, polymer libraries can be stored with agents to ensure polymer integrity. Such storage agents include, for example, antioxidants or other agents effective for preventing cross-linking of polymer molecules during storage. Depending upon the polymerization reaction, other processing steps may also be desired, all of which are preferably automated. The polymerization scheme and/or mechanism by which the polymer molecules of the polymer component of the sample are prepared is not critical, and can include, for example, reactions considered to be addition polymerization, condensation polymerization, step-growth polymerization, and/or chain-growth polymerization reactions. Viewed from another aspect, the polymerization reaction can be an emulsion polymerization or a dispersion polymerization reaction. Viewed more specifically with respect to the mechanism, the polymerization reaction can be radical polymerization, ionic polymerization (e.g., cationic polymerization, anionic polymerization), and/or ring-opening polymerization reactions, among others. Non-limiting examples of the foregoing include, Ziegler-Natta or Kaminsky-Sinn reactions and various copolymerization reactions. Polymerization product mixtures can also be prepared by modification of a polymeric starting materials, by grafting reactions, chain extension, chain scission, functional group interconversion, or other reactions.

Regardless of the particular nature of the polymer sample, sample size (i.e., volume) is not narrowly critical, and can generally vary, depending on the particular characterization protocols and systems used to characterize the sample or components thereof. Typical sample sizes can range from about 0.1 $\mu$l to about 2 ml, or from about 0.1 $\mu$l to about 1 ml, more typically from about 1 $\mu$l to about 1000 $\mu$l, even more typically from about 5 $\mu$l to about 1000 $\mu$l, about 50 $\mu$l to about 700 $\mu$l, and still more typically from about 200 $\mu$l to about 400 $\mu$l.

The polymer sample, such as a polymerization product mixture, can be a raw, untreated polymer sample or can be pretreated in preparation for characterization. Typical sample preparation steps include preliminary, non-chromatographic separation of one or more components of a polymer sample from other components, dilution, mixing and/or redissolution (e.g., from a solid state), among other operations. Preliminary separation methods can help remove large-scale impurities such as dust, coagulum or other impurities. Such separation methods can include, for example: filtering (e.g., with a microfilter having pore sizes that allow the passage of particles less than about 0.5 $\mu$m or 0.2 $\mu$m); precipitation of polymer components, monomer components and/or other small-molecule components, decanting, washing, scavenging (e.g., with drying agents), membrane separation (e.g., diafiltration, dialysis), evaporation of volatile components and/or ion-exchange. The sample is preferably diluted, if necessary, to a concentration range suitable for detection. Hence, the concentration can range from a detectable concentration level (for the particular detector employed) up to about 1 mg/ml, or more in some applications. Typical concentrations can be about $1\times10^{-2}$ wt %, about $1\times10^{-3}$ wt % or about $1\times10^{-4}$ wt %, and can generally range from about $1\times10^{-4}$ wt % to about 30 wt %, from about $1\times10^{-3}$ wt % to about 10 wt %, or from about $1\times10^{-2}$ wt % to about 1 wt %. Mixing can be required to increase the uniformity of a polymer sample emulsion or dispersion, and/or to integrate one or more additional components into the polymer sample. Preparation steps, and particularly rapid preparation techniques, can be an important aspect for combinatorial polymer investigations - since polymer samples may be synthesized in a form not ideally suited for immediate characterization.

Non-Polymer Samples

Although many applications of the present invention are directed to combinatorial polymer science research and/or quality control for industrial polymer synthesis or processing protocols, some aspects of the invention can have applications involving non-polymer samples. A non-polymer sample can be a material that comprises an organic or an inorganic non-polymer element or compound. Oligomers are considered to be polymers rather than non-polymers. The non-polymer molecule is, in some cases, preferably a non-biological non-polymer element or compound. Such non-biological non-polymer elements or compounds include non-polymer elements or compounds other than those having a well-characterized biological activity and/or a primary commercial application for a biological field (e.g., steroids, hormones, etc.). More particularly, such non-biological, non-polymer elements or compounds can include organic or inorganic pigments, carbon powders (e.g., carbon black), metals, metal oxides, metal salts, metal colloids, metal ligands, etc, without particular limitation. The non-polymer sample can be a solution, emulsion, dispersion or suspension, including colloidal solutions, dispersions or suspsensions. Biological polymers (discussed above), and biological non-polymer samples (e.g., small molecules having biological activity) can, however, also be effective characterized with the present invention in some embodiments.

In some applications, the non-polymer sample can be a synthesis reaction product mixture. As used herein, the term "reaction product mixture" refers to a mixture of sample components obtained as a product from a reaction, and preferably from a synthesis reaction. An exemplary reaction product mixture can be a sample from a combinatorial library prepared by combinatorial synthesis reactions, or can be a sample material drawn off of an industrial process line. In general, the sample may be obtained after the synthesis reaction is stopped or completed or during the course of the reaction. Alternatively, samples of each reaction product mixture can be taken and placed into an intermediate array of vessels at various times during the course of the (synthesis) reaction, optionally with addition of more solvent or other reagents to arrest the synthesis reaction or prepare the samples for analysis. These intermediate arrays can then be characterized at any time without interrupting the synthesis reaction. It is also possible to use samples or libraries of samples that were prepared previously and stored. Typically, non-polymer sample libraries can be stored with agents to ensure sample integrity. Such storage agents include, for example, agents effective for preventing further reaction of excess reactants during storage. Depending upon the reaction, other processing steps may also be desired, all of which are preferably automated. The reaction scheme and/or mechanism by which the components of the sample are prepared is not critical.

Additionally, as noted above, the non-polymer sample can preferably be a sample resulting from a dispersion and/or formulation process of non-polymer components. The particle size for non-polymer samples is not critical, and can be within the specific ranges recited for polymer samples. The sample size for non-polymer samples is likewise not critical, and can generally be within the specific ranges recited for polymer samples. Pluralities of non-polymer samples and libraries of non-polymer samples can likewise be characterized, substantially as described below in connection with pluralities and libraries of polymer samples.

Pluralities of Polymer Samples/Libraries of Polymer Samples

A plurality of polymer samples (or non-polymer samples) comprises 2 or more polymer samples (or non-polymer samples) that are physically or temporally separated from each other—for example, by residing in different sample containers, by having a membrane or other partitioning material positioned between samples, by being partitioned (e.g., in-line) with an intervening fluid, by being temporally separated in a flow process line (e.g., as sampled for process control purposes), or otherwise. The plurality of polymer samples (or non-polymer samples) preferably comprises 4 or more polymer samples and more preferably 8 or more polymer samples. Four polymer samples (or non-polymer samples) can be employed, for example, in connection with experiments having one control sample and three polymer samples varying (e.g., with respect to composition or process conditions as discussed above) to be representative of a high, a medium and a low-value of the varied factor—and thereby, to provide some indication as to trends. Four polymer (or non-polymer samples) samples are also a minimum number of samples to effect a serial-parallel characterization approach, as described above (e.g., with two detectors operating in parallel). Eight polymer samples (or non-polymer samples) can provide for additional variations in the explored factor space. Moreover, eight polymer samples (or non-polymer samples) corresponds to the number of parallel polymerization reactors in the PPR-8™, being selectively offered as one of the Discovery Tools™ of Symyx Technologies, Inc. (Santa Clara, Calif.). Higher numbers of polymer samples (or non-polymer samples) can be investigated, according to the methods of the invention, to provide additional insights into larger compositional and/or process space. In some cases, for example, the plurality of polymer samples (or non-polymer samples) can be 15 or more polymer samples (or non-polymer samples), preferably 20 or more polymer samples (or non-polymer samples), more preferably 40 or more polymer samples (or non-polymer samples) and even more preferably 80 or more polymer samples (or non-polymer samples). Such numbers can be loosely associated with standard configurations of other parallel reactor configurations (e.g., the PPR-48™, Symyx Technologies, Inc.) and/or of standard sample containers (e.g., 96-well microtiter plate-type formats). Moreover, even larger numbers of polymer samples (or non-polymer samples) can be characterized according to the methods of the present invention for larger scale research endeavors. Hence, the number of polymer samples (or non-polymer samples) can be 150 or more, 400 or more, 500 or more, 750 or more, 1,000 or more, 1,500 or more, 2,000 or more, 5,000 or more and 10,000 or more polymer samples (or non-polymer samples). As such, the number of polymer samples (or non-polymer samples) can range from about 2 polymer samples (or non-polymer samples) to about 10,000 polymer samples (or non-polymer samples), and preferably from about 8 polymer samples (or non-polymer samples) to about 10,000 (or non-polymer samples) polymer samples. In many applications, however, the number of polymer samples (or non-polymer samples) can range from about 80 polymer samples (or non-polymer samples) to about 1500 polymer samples (or non-polymer samples). In some cases, in which processing of polymer samples (or non-polymer samples) using typical 96-well microtiter-plate formatting is convenient or otherwise desirable, the number of polymer samples (or non-polymer samples) can be 96*N, where N is an integer ranging from about 1 to about 100. For many applications, N can suitably range from 1 to about 20, and in some cases, from 1 to about 5.

The plurality of polymer samples (or non-polymer samples) can be a library of polymer samples (or non-polymer samples). A library of polymer samples (or non-polymer samples) comprises an array of two or more different polymer samples (or non-polymer samples) spatially separated—preferably on a common substrate, or temporally separated—for example, in a flow system. Candidate polymer samples (or non-polymer samples) (i.e., members) within a library may differ in a definable and typically predefined way, including with regard to chemical structure, processing (e.g., synthesis) history, mixtures of interacting components, purity, etc. The polymer samples (or non-polymer samples) are spatially separated, preferably at an exposed surface of the substrate, such that the array of polymer samples (or non-polymer samples) are separately addressable for characterization thereof. The two or more different polymer samples (or non-polymer samples) can reside in sample containers formed as wells in a surface of the substrate. The number of polymer samples (or non-polymer samples) included within the library can generally be the same as the number of samples included within the plurality of samples, as discussed above. In general, however, not all of the polymer samples (or non-polymer samples) within a library of polymer samples (or non-polymer samples) need to be different polymer samples (or non-polymer samples). When process conditions are to be evaluated, the libraries may contain only one type of polymer sample (or non-polymer samples). Typically, however, for combinatorial polymer science research applications, at least two or more, preferably at least four or more, even more preferably eight or more and, in many cases most, and allowably each of the plurality of polymer samples (or non-polymer samples) in a given library of polymer samples (or non-polymer samples) will be different from each other. Specifically, a different polymer sample (or non-polymer samples) can be included within at least about 50%, preferably at least 75%, preferably at least 80%, even more preferably at least 90%, still more preferably at least 95%, yet more preferably at least 98% and most preferably at least 99% of the polymer samples (or non-polymer samples) included in the sample library. In some cases, all of the polymer samples (or non-polymer samples) in a library of polymer samples (or non-polymer samples) will be different from each other.

The substrate can be a structure having a rigid or semi-rigid surface on which or into which the array of polymer samples (or non-polymer samples) can be formed or deposited. The substrate can be of any suitable material, and preferably consists essentially of materials that are inert with respect to the polymer samples (or non-polymer samples) of interest. Certain materials will, therefore, be less desirably employed as a substrate material for certain polymerization reaction process conditions (e.g., high temperatures—especially temperatures greater than about 100° C.—or high pressures) and/or for certain reaction mechanisms. Stainless steel, silicon, including polycrystalline silicon, single-crystal silicon, sputtered silicon, and silica ($SiO_2$) in any of its forms (quartz, glass, etc.) are preferred substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material in some applications. Organic and inorganic polymers may also be suitably employed in some applications of the invention. Exemplary polymeric materials that can be suitable as a substrate material in particular applications include polyimides such as Kapton™, polypropylene, polytetrafluoroethylene (PTFE) and/or polyether etherketone (PEEK), among others. The substrate material is also preferably selected for suitability in connection with known fabrication techniques. As to form, the sample containers formed in, at or on a substrate can be preferably, but are not necessarily, arranged in a substantially flat, substantially planar surface of the substrate. The sample containers can be formed in a surface of the substrate as dimples, wells, raised regions, trenches, or the like. Non-conventional substate-based sample containers, such as relatively flat surfaces having surface-modified regions (e.g., selectively wettable regions) can also be employed. The overall size and/or shape of the substrate is not limiting to the invention. The size and shape can be chosen, however, to be compatible with commercial availability, existing fabrication techniques, and/or with known or later-developed automation techniques, including automated sampling and automated substrate-handling devices. The substrate is also preferably sized to be portable by humans. The substrate can be thermally insulated, particularly for high-temperature and/or low-temperature applications. In preferred embodiments, the substrate is designed such that the individually addressable regions of the substrate can act as polymerization reaction vessels for preparing a polymerization product mixture (as well as sample containers for the two or more different polymer samples during subsequent characterization thereof. Glass-lined, 96-well, 384-well and 1536-well microtiter-type plates, fabricated from stainless steel and/or aluminum, are preferred substrates for a library of polymer samples. The choice of an appropriate specific substrate material and/or form for certain applications will be apparent to those of skill in the art in view of the guidance provided herein.

The library of polymer materials can be a combinatorial library of polymerization product mixtures. Polymer libraries can comprise, for example, polymerization product mixtures resulting from polymerization reactions that are varied with respect to, for example, reactant materials (e.g., monomers, comonomers), catalysts, catalyst precursors, initiators, additives, the relative amounts of such components, reaction conditions (e.g., temperature, pressure, reaction time) or any other factor affecting polymerization. Design variables for polymerization reactions are well known in the art. See generally, Odian, *Principles of Polymerization*, $3^{rd}$ Ed., John Wiley & Sons, Inc. (1991). A library of polymer samples may be prepared in arrays, in parallel polymerization reactors or in a serial fashion. Exemplary methods and apparatus for preparing polymer libraries—based on combinatorial polymer synthesis approaches—are disclosed in copending U.S. patent application Ser. No. 09/211,982 of Turner et al. filed Dec. 14, 1998, copending U.S. patent application Ser. No. 09/227,558 of Turner et al. filed Jan. 8, 1999, copending U.S. patent application Ser. No. 09/235,368 of Weinberg et al. filed Jan. 21, 1999, and copending U.S. provisional patent application Ser. No. 60/122,704 entitled "Controlled, Stable Free Radical Emulsion and Water-Based Polymerizations", filed Mar. 9, 1999 by Klaerner et al. See also, PCT patent application WO 96/11878.

The libraries can be advantageously characterized directly, without being isolated, from the reaction vessel in which the polymer was synthesized. Thus, reagents, catalysts or initiators and other additives for making polymers may be included with the polymer sample for characterization or screening.

While such methods are preferred for a combinatorial approach to polymer science research, they are to be considered exemplary and non-limiting. As noted above, the particular polymer samples characterized according to the methods and with the apparatus disclosed herein can be from any source, including, but not limited to polymerization product mixtures resulting from combinatorially synthesis approaches.

Detectors/Detected Properties/Determined Properties

A sample (e.g., polymer sample) is characterized by detecting a property of the sample, or by detecting a property of a component (e.g., a polymer component, a monomer component, a non-polymer component) of the sample. In many cases, the property is detected over a period of time, such that a variation in the property can be observed or detected or the rate of change of variation of a property can be observed or detected. In the general case, the detected property can be any property which can provide a scientifically meaningful basis of comparison between two different samples (e.g. polymer samples) or between two different sample components—either directly, or after being correlated to a specific characterizing property of interest. The detected property can be a chemical property or a physical property of the sample or component thereof. In preferred applications, an optical property of the sample (e.g. polymer sample) or a component thereof can be detected. For example, an amount, frequency, intensity or direction of an incident light that is refracted, scattered, and/or absorbed by the polymer sample or a component thereof may be detected. Other properties, such as pressure or other factors affecting a particular characterizing property of interest (e.g., viscosity) can likewise be detected.

The protocols for characterizing one or more samples such as polymer samples preferably further comprise determining a property of interest from the detected property. The physically-detected properties, such as the capability of the sample (e.g., polymer sample) or component thereof to refract, scatter, emit or absorb light can be correlated to properties of interest. Such properties of interest include, without limitation, weight-average molecular weight, number-average molecular weight, viscosity-average molecular weight, peak molecular weight, approximate molecular weight, polydispersity index, molecular-weight-distribution shape, relative or absolute component concentration, chemical composition, conversion, concentration, mass, hydrodynamic radius ($R_h$), radius of gyration ($R_g$), chemical composition, amounts of residual monomer, presence and amounts of other low-molecular weight impurities in polymer samples, particle or molecular size, intrinsic viscosity, molecular shape, molecular conformation, and/or agglomeration or assemblage of molecules. The correlation (i.e., relationship) between a detected property and a determined property of interest can be based on mathematical models and/or empirical calibrations. See, for example, the aforementioned equation (1) and equation (3). Such correlation or relationship methods are generally known in the art, and are typically incorporated into commercially-available chromatographic detectors and/or detector or data-acquisition software.

For combinatorial polymer science research applications, as well as other applications, the characterization protocols can be effected to determine at least particle size and/or particle size distribution characterization properties of primary importance. For combinatorial formulations research applications, the determined property, such as particle size, can be used as a screen (primary or secondary) for important commercial properties such as stability. For example, stability testing of a nanodispersant formulation sample (or of a library of nanodispersant formulation samples) can be effected by determining the particle size of the dispersed phase according to the present invention at a first time (e.g., at or near nanodispersion formation), and then determining the particle size of the dispersed phase at a second time (e.g., 1, 2, 3 or 4 weeks after nanodispersion formation, or following thermal aging tests, etc.). Stability can also be examined under various process conditions (temperature, shaking, etc.).

The aforementioned characterizing properties of interest can, once determined, be mathematically combined in various combinations to provide figures of merit for various properties or attributes of interest. In particular, for example, molecular weight, conversion and polydispersity index can be evaluated versus polymerization process time to provide mechanistic insights as to how polymers are formed. Other combinations of the fundamental characterization properties of interest will be apparent to those of skill in the art.

Specific applications and/or combinations of detectors, as well as correlation protocols, are discussed in greater detail below.

Sample-Throughput

For methods directed to characterizing a plurality of samples, a property of each of the samples or of one or more components thereof is detected—serially or in a parallel, serial-parallel or hybrid parallel-serial manner—at an average sample throughput of not more than about 10 minutes per sample. As used in connection herewith, the term "average sample throughput" refers to the sample-number normalized total (cumulative) period of time required to detect a property of two or more polymer samples with a characterization system. The total, cumulative time period is delineated from the initiation of the characterization process for the first sample, to the detection of a property of the last sample or of a component thereof, and includes any intervening between-sample pauses in the process. The sample throughput is more preferably not more than about 8 minutes per sample, even more preferably not more than about 4 minutes per sample and still more preferably not more than about 2 minutes per sample. Depending on the quality resolution of the characterizing information required, the average sample throughput can be not more than about 1 minute per sample, and if desired, not more than about 30 seconds per sample, not more than about 20 seconds per sample or not more than about 10 seconds per sample, and in some applications not more than about 5 seconds per sample and not more than about 1 second per sample. Sample-throughput values of less than 10 seconds are demonstrated in the examples. The average sample-throughput preferably ranges from about 10 minutes per sample to about 1 second per sample, more preferably from about 8 minutes per sample to about 2 seconds per sample, even more preferably from about 2 minutes per sample to about 3 seconds per sample and, in some applications, most preferably from about 1 minute per sample to about 5 seconds per sample.

A sample-throughput of 10 minutes per sample or less is important for a number of reasons. Non-flow characterization systems that detect a property of a polymer sample or of a component thereof at the aforementioned sample throughput rates can be employed effectively in a combinatorial research program, such as a combinatorial polymer research program, a combinatorial heterogeneous catalyst research program, a combinatorial dispersions (formulations) program, among others. From a completely practical point of view, the characterization rates are roughly commensurate with reasonably-scaled sample (e.g., polymer sample) library synthesis rates. It is generally desirable that combinatorial screening systems, such as the polymer characterization protocols disclosed herein, operate with roughly the same sample throughput as combinatorial synthesis protocols—to prevent a backlog of uncharacterized reaction product (e.g., polymerization product) samples. Hence, because moderate scale synthesis systems, such as the Discovery Tools™ PPR-48™ (Symyx Technologies, Santa Clara Calif.), can readily prepare sample libraries such as polymer libraries with a sample-throughput of about 100 polymer samples per day, a screening throughput of about 10 minutes per sample or faster is desirable. Higher throughput synthesis systems demand higher characterization throughputs. The preferred higher throughput values are also important with respect to process control applications, to provide near-real time control data. It is possible, moreover, that a particular sample being characterized may include component that are themselves different analytes of interest, such that the per-analyte throughput for the characterization system can be significantly higher than the per-sample throughput thereof.

Additionally, as shown in connection with the examples provided herein, the characterization of polymer samples at such throughputs can offer sufficiently rigorous quality of data, especially particle size, particle size distribution, and others (e.g., weight-average molecular weight) to be useful for scientifically meaningful exploration of the polymer compositional and/or polymerization reaction conditions research space.

Specific protocols, systems and devices for achieving the aforementioned average sample throughput values for a plurality of polymer samples are discussed and exemplified in greater detail below.

Sampling/Auto-Sampler

An array of samples can be provided, in one embodiment, by sampling various samples into or onto a sample holder. Sampling of a sample such as a polymer sample refers to a plurality of steps which include withdrawing a sample (e.g., polymer sample) from a sample container and delivering at least a portion of the withdrawn sample to a characterization system. Sampling may also include additional steps, particularly and preferably, sample preparation steps. (See FIG. 1A). In one approach, with respect to polymer samples for example, only one polymer sample is withdrawn into the auto-sampler probe at a time and only one polymer sample resides in the probe at one time. The one polymer sample is expelled therefrom (for sample preparation and/or into the polymer characterization system) before drawing the next polymer sample. In an alternative approach, however, two or more polymer samples can be withdrawn into the auto-sampler probe sequentially, spatially separated by a solvent, such that the two or more polymer samples reside in the probe at the same time. Such a "candystriping" approach can provide for very high auto-sampler throughputs for rapid introduction of the one or more samples into the flow characterization system.

The sample container from which the polymer sample is withdrawn is not critical. The sample container can be, for example a sample-containing well. The sample-containing well can be a sample vial, a plurality of sample vials, or a sample-containing well within an array of sample-containing wells (e.g., constituting a polymer sample library). The sample container can alternatively be a sample port from a sample line in fluid communication with an industrial process line, such as a polymerization process line.

In the general case, sampling can be effected manually, in a semi-automatic manner or in an automatic manner. A polymer sample can be withdrawn from a sample container manually, for example, with a pipette or with a syringe-type manual probe, and then manually delivered to a polymer characterization system. In a semi-automatic protocol, some aspect of the protocol is effected automatically (e.g., delivery), but some other aspect requires manual intervention (e.g., withdrawal of polymer samples from a process control line). Preferably, however, the polymer sample(s) are withdrawn from a sample container and delivered to the characterization system in a fully automated manner—for example, with an auto-sampler.

A plurality of polymer samples, such as those included within a library of polymer samples, is preferably prepared or delivered to a sample holder, with an automatic delivery device, such as an auto-sampler. The sample holder can be adapted for translation, as discussed above. Additionally, the sample holder can be adapted for presenting an array of liquid samples in a non-flow characterization system. As used herein, the term "auto-sampler" refers to an apparatus suitable for automated sampling of polymer samples for characterization, including automated withdrawal of a polymer sample from a sample container, optional automated preparation of the sample, and loading of at least a portion of the withdrawn sample into a sample holder of the non-flow characterization system. Automated sampling equipment is available commercially for introducing multiple samples into liquid flow systems in a serial or parallel manner. Preferably, the sampling system is capable of high-throughput, and is designed for complex sample preparation, including transfer, dilution, purification, precipitation, or other steps needed to prepare elements of a combinatorial array for characterization. The auto-sampling systems disclosed in the above-identified co-pending related application, Ser. No. 09/285,393 entitled "Automated Sampling Methods for Rapid Characterization of Polymers", filed Apr. 2, 1999 by Petro et al., are preferred.

Sample preparation steps can also be included in the preferred protocol for providing a plurality of samples such as polymer samples. The sample preparation steps, examples of which are discussed more specifically below, are preferably automated, and preferably effected with the auto-sampler.

Significantly, sample preparation steps (also referred to herein as pretreatment steps) for a plurality of samples are preferably integrated into a sampling approach such that each of the prepared samples is loaded into the polymer characterization system, and subsequently characterized shortly after the sample-preparation steps are completed. The particular sample-preparation (pretreatment) steps are not critical, and desired pretreatment protocols are well known in the art. As discussed above in connection with the polymer sample, the pretreating step can comprise diluting the sample, separating one or more components of the sample from other components thereof, and/or mixing the sample. These steps can be, and are preferably, effected with an auto-sampler. Variations and other approaches for automated sample preparation will be apparent to a person of skill in the art, and as such, the present invention is not limited by these exemplary protocols. A polymer sample may be diluted with the auto-sampler to a concentration range suitable for detection by combining the expelled sample with a diluting agent (e.g., solvent) in the sample-preparation container. Preliminary, separation of one or more non-polymer components (e.g., impurities) from a polymer sample may also be effected with an auto-sampler. as follows. Moreover, the polymer sample could be filtered as a preparation step, prior to loading of the polymer sample into the flow characterization system.

Microprocessors

One or more microprocessors can, as noted, be employed for controlling every aspect of the flow characterization systems, including relative translation between the sample holder and array of light-scattering probes (e.g., as included in a probe head). Microprocessors can also be employed in connection with sample preparation, sampling, and/or in immersion-probe embodiments, washing of the immersion probe.

Multi-System, Rapid-Serial Polymer Characterization

The high-throughput rapid-serial flow characterization systems can be advantageously applied in combination with other sample (e.g., polymer characterization systems) for effectively and efficiently characterizing a plurality of polymer samples. Specific approaches are generally described, for example, in co-pending application Ser. No. 09/285,963, filed Apr. 2, 1999 by Safir et al., entitled "Rapid Characterization of Polymers" and in PCT application PCT/US99/07304 filed on Apr. 2, 1999.

The following examples illustrate the principles and advantages of the invention.

EXAMPLES

Example 1

Parallel Characterization of Polymers with Dynamic Light Scattering

This example demonstrates the characterization of a 96-member library of emulsion polymers in a parallel manner—using a plurality of dynamic light-scattering (DLS) detector probes. Because the number of DLS probes was less than the total number of samples, the library was evaluated in a serial-parallel (i.e., semi-parallel) manner. The average sample-throughput for characterizing the entire library in this manner was about 5–15 seconds per sample.

An emulsion library prepared by combinatorial synthesis techniques was prepared and diluted prior to characterization with ultrapure water to a concentration of about 0.001 wt % using an auto-sampler. No filtering was performed on the dispersion before the measurements.

Figure 2:
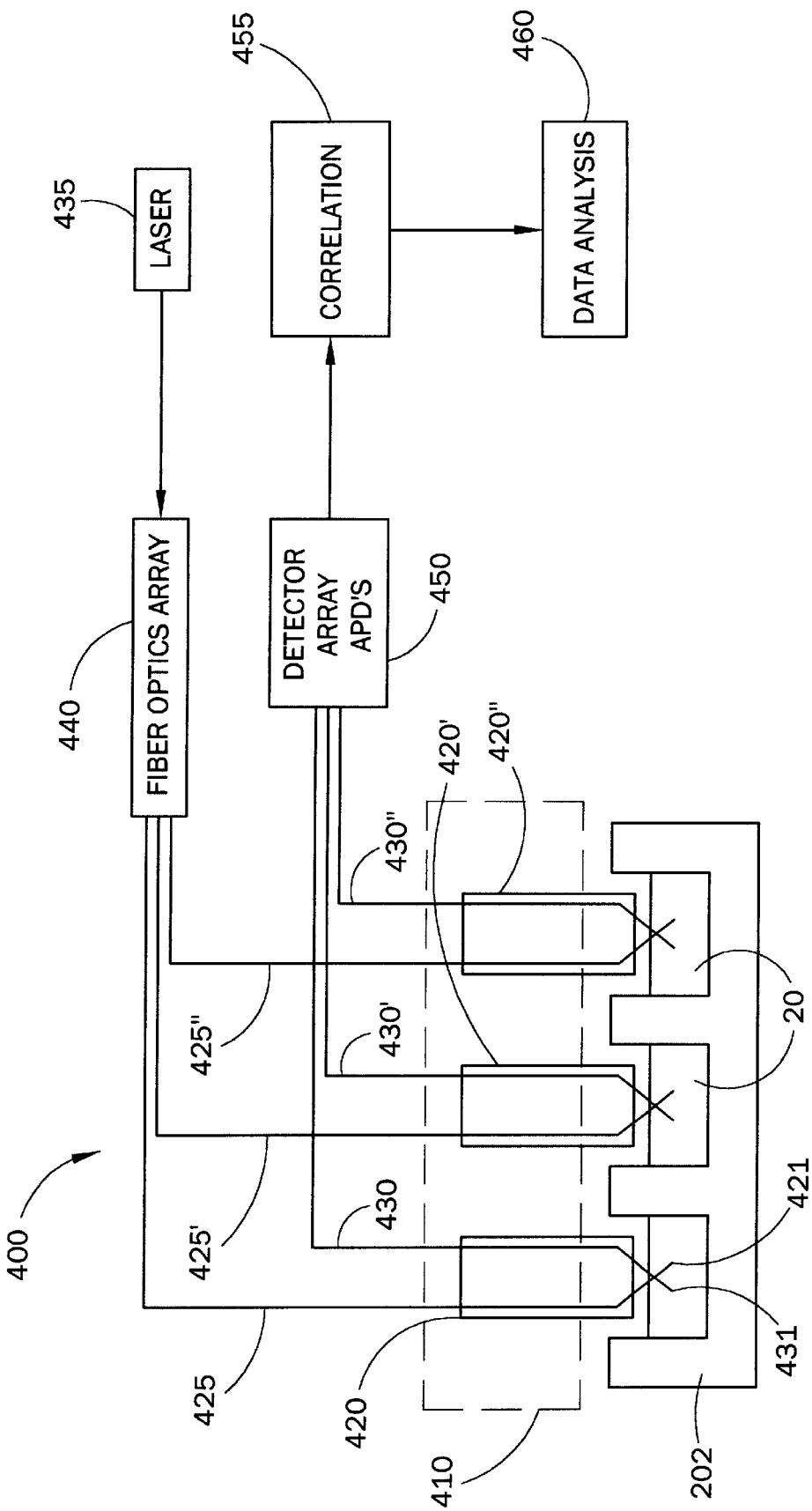
FIG. 2 is a schematic diagram illustrating a parallel, non-flow, dynamic light-scattering (DLS) polymer characterization system (shown with an array of immersion probes).

A parallel DLS system used for characterizing the library of polymer samples was configured substantially as shown in FIG. 2 and described in connection therewith. Briefly, the system comprised an array 410 of two DLS probes 420 supported in parallel by a common support structure (i.e., probe head). Each probe 420 included a transmitting optical fiber 425, 425' and a receiving optical fiber 430, 430'.

Two single-mode fiber couplers, also referred to as optics (not shown), were used for transmitting an incident light and collecting a scattered light. These couplers consisted of a gradient refractive index (GRIN) lens aligned to a single-mode optical fiber. (Such couplers are typically used for coupling the output of a laser diode into an optical fiber.). For the DLS application, a focal length of 10 mm for both source and detector optics were chosen. The optics were mounted at an angle of 45 degrees with respect to each other giving a measurement angle of 135 degrees.

A HeNe laser 435 provided laser light at 632.8 nm wavelength (5 mW, Melles Griot). The laser light was coupled into the transmitting optical fiber in the fiber-optics array 440 and delivered into the sample 20 by the first optic. The scattered light was collected by the second optic. Unlike the immersed-probe configuration shown in FIG. 2, the measurements were done in a non-immersion, non-contact mode by mounting the probes approximately 5 mm above the liquid surface, such that the laser beam was delivered and the scattered light was collected through the liquid surface.

The scattered light collected by the second optic was coupled into the receiving optical fiber. The receiving optical fiber was connected to an avalanche photodiode (SPCM, EG&G, Canada). Measurements were performed at a temperature of 21° C. The measurements and photon autocorrelation were taken in a serial manner with a data acquisition time of 5 seconds per sample using a commercial autocorrelator board (ALV 5000/E, ALV GmbH Langen, Germany). The autocorrelation function was analyzed by a second order cumulant analysis (ALV Software, Version 2.0) and the hydrodynamic radius $R_h$ and the polydispersity index (PDI) were determined.

These data are presented in Tables 1-1 and 1-2, respectively. A comparative example demonstrated that the average hydrodynamic radii determined by this parallel DLS, non-immersion detection approach correlated well with those values determined by variable flow-injection analysis.

Including time for positioning the sample under the probe, the total measurement took between 5 and 15 seconds per well.

TABLE 1-1

Determined Average $R_h$ (nm) for Emulsion Polymer Library

|   | 1 | 2 | 3 | 4 | 5 | 6 | 7 | 8 | 9 | 10 | 11 | 12 |
|---|---|---|---|---|---|---|---|---|---|----|----|----|
| A | 38.8 | 40.4 | 45.9 | 46.4 | 49.5 | 48.9 | 50.1 | 56.2 | 50.1 | 51.9 | 53.2 | 54.8 |
| B | 43.8 | 48.1 | 52.7 | 50.6 | 50.9 | 52.5 | 52.1 | 51.3 | 54.8 | 55.8 | 48.5 | 45.2 |
| C | 48.5 | 50.4 | 51.8 | 50.3 | 53.2 | 51.2 | 54.1 | 59.2 | 54.3 | 49.3 | 48.3 | 47.2 |
| D | 50.5 | 52.2 | 52.9 | 51.7 | 52.9 | 58.1 | 59.2 | 53.9 | 49.1 | 50.8 | 48.6 | 46.2 |
| E | 56.0 | 53.6 | 54.7 | 55.0 | 58.7 | 56.3 | 52.6 | 48.6 | 47.0 | 49.1 | 47.5 | 48.4 |
| F | 51.0 | 54.2 | 56.2 | 61.0 | 54.2 | 50.9 | 50.9 | 52.2 | 49.0 | 50.3 | 46.8 | 48.2 |
| G | 53.8 | 55.5 | 56.3 | 53.6 | 53.1 | 52.8 | 49.4 | 45.6 | 48.9 | 43.8 | 45.7 | 48.2 |
| H | 58.2 | 56.1 | 54.8 | 55.1 | 50.7 | 49.1 | 49.4 | 47.1 | 49.6 | 44.7 | 44.4 | 46.3 |

TABLE 1-2

Determined PDI (cumulant analysis) for Emulsion Polymer Library

|   | 1 | 2 | 3 | 4 | 5 | 6 | 7 | 8 | 9 | 10 | 11 | 12 |
|---|---|---|---|---|---|---|---|---|---|----|----|----|
| A | 0.08 | 0.08 | 0.03 | 0.03 | 0.01 | 0.09 | 0.08 | 0.06 | 0.06 | 0.02 | 0.11 | 0.05 |
| B | 0.09 | 0.14 | 0.25 | 0.11 | 0.15 | 0.07 | 0.15 | 0.13 | 0.04 | 0.04 | 0.02 | 0.12 |
| C | 0.08 | 0.01 | 0.01 | 0.01 | 0.06 | 0.07 | 0.05 | 0.11 | 0.02 | 0.02 | <0.01 | 0.06 |
| D | 0.06 | 0.08 | 0.03 | 0.09 | 0.06 | 0.02 | 0.12 | 0.09 | 0.05 | 0.01 | <0.01 | 0.08 |
| E | 0.09 | 0.08 | 0.03 | 0.03 | 0.13 | 0.04 | 0.01 | 0.01 | 0.02 | 0.06 | 0.01 | 0.02 |
| F | <0.01 | 0.03 | 0.03 | 0.08 | 0.07 | 0.03 | 0.04 | 0.03 | 0.11 | 0.06 | 0.04 | 0.07 |
| G | 0.08 | 0.08 | 0.06 | 0.06 | 0.06 | 0.09 | 0.05 | <0.01 | 0.09 | 0.10 | 0.12 | 0.09 |
| H | 0.05 | 0.06 | 0.01 | 0.06 | 0.05 | 0.05 | 0.10 | 0.01 | 0.15 | <0.01 | 0.14 | 0.09 |

Example 2

A probe head comprising two fiber-optic probes were employed to analyze a library of samples in a serial-parallel manner.

Briefly, a red Helium-Neon laser light (632.8 nm) was coupled from a 10 mW laser into a monomode optical fiber and split into two output fibers with a fiber optics splitter. Each fiber was connectorized to another fiber that is terminated with a GRIN lens with a 10 mm focal length (Princeton Optics, USA). The output power of the laser light for the two channels was adjusted by attenuators.

The geometry of the apparatus is described for one probe of the probe head as follows. The GRIN lens connectorized end of one of the fibers was mounted into a housing that allows vertical transmission of the light into a microtiter plate. The fiber end was positioned approximately 5 mm from the liquid surface (the rim of the well) of the samples in the microtiter plate. The incident laser beam—for transmitting the laser light—was adjusted slightly off-center of the well under observation to prevent backscattering into the fiber and to provide enough space for the light path into the receiving fiber with a scattering volume at a suitable height of the sample. The GRIN lens end of the detection fiber—for receiving the scattered light—was positioned into a holder and an adjustable mount such that the light paths of the two fibers intersected at a distance of approximately 7 mm from the end of both GRIN lenses and form an angle of approximately 135 degrees. By translating the end of the fiber, the size of the scattering volume and the intensity of the scattered light was adjusted. In this geometry the height of the scattering volume was about 2 mm below the meniscus of the liquid. Once the fibers were aligned, the adjustment was stable over the course of months.

The transmitting and receiving fibers and their housing were integrally mounted to form a fiber optic light-scattering probe, which in turn was integrated with another, substantially identical probe, to form a probe head comprising the array of light-scattering probes. As such, the array of probes could be removed or translated without readjusting the fibers.

The intensity of the scattered light was collected, for the two probes, with two avalanche photo diodes capable of single photon counting (EG&G Canada, 250 dark counts/sec). The instantaneous photon count rates were transferred to an ALV5000/E correlator board (ALV GmbH, Germany) and the photon-photon autocorrelation function was calculated by the multiple-tau technique. A cumulant fit of the autocorrelation function yields the average particle hydrodynamic radius $R_h$ and the polydispersity index PDI (second cumulant). The software of the correlator board was interfaced with software (Labview 5.1, National Instruments, Austin, Tex.) such that measurement parameters, data acquisition and analysis, and transfer and saving of results, and motion control was achieved automatically for an entire library. The results were recorded both for individual measurements and in a summary format ($R_h$, PDI, average count rate) for the entire library, see also the sample results file below.

The software also allowed addressing of individual wells of the microtiter plate. The translational motion stages for moving the microtiter plate in X and Y directions (Micos) had a range of 15 cm each and were controlled by a NuDrive motion controller (National Instruments).

Numerous experiments were performed on various types of samples, including polystyrene latex standards, polymers synthesized by emulsion polymerization, nanodispersions and polymers in solution.

A typical combinatorial library measured consisted of a dispersed small molecule substrate (active ingredient) stabilized with a copolymer (consisting of Styrene, vinyl acetate, methyl acrylate and N-(3-(dimethylamino)-propyl) methacrylamide) in a ph7 buffered aqueous dispersion. 50 µl of the dispersion having a total solids content of 1.5 wt. % were transferred into an optical microtiter plate (Costar, black PS) and diluted to 380 µl with automated liquid handling equipment. The microtiter plate was placed into the sample mount in the load position of the FODLS instrument and moved to the start position. Acquisition parameters were: laser wavelength 632.8 nm, index of refraction 1.333, scattering angle 122.1 degrees (refractive index corrected for water), temperature 295K, viscosity 0.9632 cp, measurement duration 5 sec per well. The overall measurement time including data transfer and sample translation with these measurement parameters was 14 min per library of 96 elements (less than 9 seconds per sample). In other experiments, the overall measurement time including data transfer and sample translation with these measurement parameters was 8 min per library of 96 elements (about 5 seconds per sample).

The results are shown below in Tables 2-1, 2-2 and 2-3. Elements marked gray have a count rate higher than 10 kHz and give physically meaningful results for $R_h$ and PDI. The other elements have average count rates below 10 kHz and often give spurious results or no results at all. This is due to materials failure in the preparation of the samples, e.g. by precipitation.

TABLE 2-1

Hydrodynamic Radius $R_h$, (nm)

| Row | Col 1 | 2 | 3 | 4 | 5 | 6 | 7 | 8 | 9 | 10 | 11 | 12 |
|---|---|---|---|---|---|---|---|---|---|---|---|---|
| A | 41.5 | 44.1 | 66.1 | 63.9 | 73.9 | 77.5 | 72.5 | 130.9 | 137.1 | 75.5 | 106.1 | 129.1 |
| B | 27.2 | 25.2 | 31.8 | 40.9 | 33.7 | 37.1 | 54.1 | 58.4 | 59.1 | 105.7 | 84.2 | 110.8 |
| C | 52.5 | 46.4 | 52.2 | 46.9 | 37.7 | 50.6 | 36 | 37 | 38.2 | 72.9 | 81.3 | 84.1 |
| D | 38.9 | — | 26.3 | 69 | 53.9 | 53.3 | 41.9 | 52.6 | 34.6 | 37.5 | 72.5 | 70.1 |
| E | — | 0.4 | 0.5 | 60.9 | 27.1 | 88 | 67.9 | 64.2 | 58.3 | 42.3 | 41.6 | 83.2 |
| F | 95.9 | 0.1 | 109.9 | 0.3 | 0.2 | 33.8 | 25.7 | 104.4 | 65.8 | 54.8 | 45.6 | 28.6 |
| G | 71.7 | 0.4 | 197.4 | 0.4 | — | 838.7 | 83.6 | 116.8 | 71.7 | 76.7 | 67.4 | 158.6 |
| H | 61 | -5.4 | 5.5 | 94.2 | 13.2 | 0.8 | 0.5 | 0.6 | 63.8 | — | 103.6 | 116.3 |

TABLE 2-2

Polydispersity Index
PDI (second cumulant)

| Row | Col 1 | 2 | 3 | 4 | 5 | 6 | 7 | 8 | 9 | 10 | 11 | 12 |
|---|---|---|---|---|---|---|---|---|---|---|---|---|
| A | 0.053 | 0.168 | 0.167 | 0.229 | 0.134 | 0.121 | 0.178 | 0.302 | 0.448 | 0.245 | 0.098 | 0.262 |
| B | 0.132 | −0.009 | 0.113 | 0.227 | 0.018 | 0.139 | 0.013 | 0.295 | 0.469 | 0.122 | 0.042 | −0.802 |
| C | 0.13 | 0.165 | 0.196 | 0.256 | 0.407 | 0.354 | 0.067 | 0.145 | 0.109 | 0.066 | 0.057 | 0.134 |
| D | 0.468 | — | 0.509 | 0.081 | 0.296 | 0.228 | 0.166 | 0.236 | 0.038 | 0.125 | 0.193 | 0.218 |
| E | — | 0.978 | 1.108 | 0.644 | 0.556 | 0.222 | 0.167 | 0.131 | 0.131 | 0.051 | 0.045 | 0.391 |
| F | 0.095 | 0.639 | 0.542 | 0.848 | 1.235 | 0.536 | 0.333 | 0.246 | 0.225 | 0.127 | 0.075 | 0.095 |
| G | −0.445 | 0.865 | 0.609 | 1.353 | — | 4222020 | 0.336 | 0.417 | 0.454 | 0.237 | 0.163 | 0.428 |
| H | 0.89 | −78.736 | −131.84 | 0.718 | −54.479 | −3.599 | −0.999 | −2.472 | 0.357 | — | 0.173 | −0.591 |

TABLE 2-3

Average Count Rate
Average Count Rate, (kHz)

| Row | Col 1 | 2 | 3 | 4 | 5 | 6 | 7 | 8 | 9 | 10 | 11 | 12 |
|---|---|---|---|---|---|---|---|---|---|---|---|---|
| A | 556.4 | 597.2 | 669.4 | 291.5 | 598.8 | 303.1 | 262.3 | 277.3 | 293.2 | 251.8 | 681.9 | 428.6 |
| B | 152.9 | 401.2 | 670.9 | 136.2 | 77.3 | 651.7 | 280 | 452 | 19.5 | 478.9 | 777.2 | 520.1 |
| C | 227 | 872.9 | 1009.2 | 786.8 | 214 | 1077.5 | 138.7 | 508 | 188.3 | 198.5 | 1068 | 663.3 |
| D | 5.8 | 4 | 5.5 | 170.8 | 66.1 | 338.5 | 768.4 | 562.4 | 216.2 | 210.5 | 498.3 | 276.1 |
| E | 4.5 | 5.9 | 5.1 | 7.2 | 6 | 73.1 | 1758.9 | 820.2 | 438.6 | 431.3 | 489.9 | 400.4 |
| F | 3.5 | 2.8 | 5 | 4.8 | 2.4 | 8.2 | 42.2 | 400 | 333.7 | 341.9 | 968.2 | 171.3 |
| G | 4.9 | 4.7 | 11.9 | 5.5 | 2.8 | 2.7 | 80.4 | 28.9 | 40.2 | 77 | 111.9 | 504.7 |
| H | 5.9 | 1.9 | 3.4 | 8.9 | 2.9 | 2.4 | 2.4 | 2 | 2.2 | 3.1 | 3.4 | 4 |

Example 3

Analysis of Gas-Liquid Interface

This example details an analysis of a gas-liquid interface for a sample in an open top container.

The interface of an open top container is bounded by three-phase contact lines in which the boundary condition takes the form of the Young equation:

$$\sigma_{lg} \cos\alpha = \sigma_{ls} - \sigma_{gs} \quad (4)$$

where $\alpha$ is the three-phase contact angle and $\sigma_{ij}$ are the surface tensions of the various liquid, solid and gaseous interfaces. For a given three-phase system the contact angle $\alpha$ is a material characteristic. For the case of a vial being almost filled, the contact angle is determined by the amount of liquid in the vial. A particular case is a cylindrical vial where the meniscus meets the axis of rotational symmetry. When the effect of gravity is negligible, such a meniscus is part of a sphere. Then the pressure change $\Delta P$ across the interface can be described by the Laplace equation $2\sigma/R = \Delta P$ with R being the radius of the sphere. In case of an axisymmetric meniscus the Laplace equation is given by $$\frac{1}{r}\frac{d}{dr}\left[\frac{rz'}{(1+z'^2)^{\frac{1}{2}}}\right] = \frac{\Delta P}{\sigma} \quad z = z(r) \quad (5)$$

When the gravity effect is not negligible, the capillary pressure becomes dependent on the z-coordinate and for a small meniscus slope can be described as $$z(r) = 2[I_0(ur) - 1]/(bu^2), \quad u = (\Delta\rho g/\sigma)^{1/2} \quad (6)$$

where $I_0(x)$ is the modified Bessel function of the first kind and zeroth order.

Figure 10A:
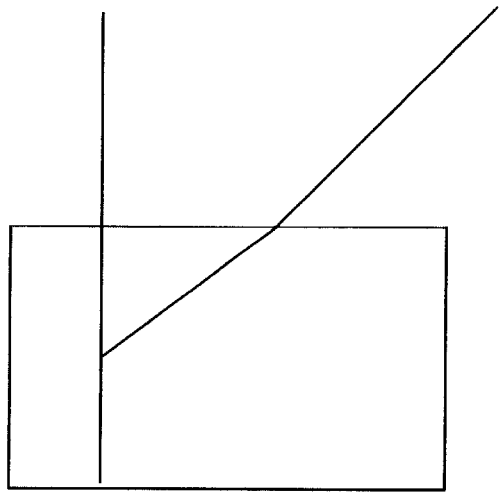
FIGS. 10A through 10D are schematic illustrations representing an incident light illuminating a sample and a scattered light (to be detected) through a gas-liquid sample interface defined by various-shaped meniscus.
Figure 10B:
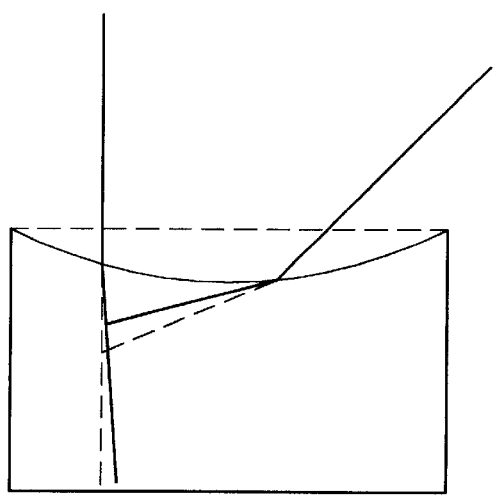
Figure 10C:
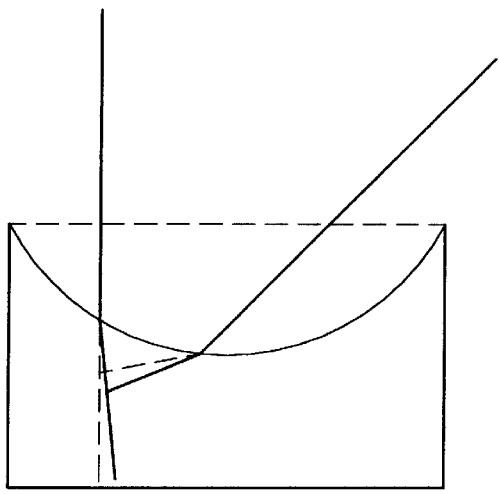
Figure 10D:
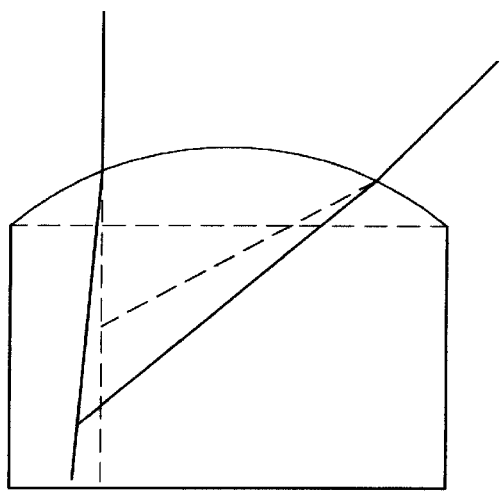

Different shapes of meniscus are shown in FIGS. 10A through 10D. FIG. 10A shows a substantially flat meniscus and the resulting scattering angle due to refraction at the air/liquid interface. FIGS. 10B and 10C show containers that are underfilled to various degrees and the resulting change in scattering geometry (full line) relative to the scattering geometry for a substantially flat meniscus at the liquid/air interface (dashed line). The meniscus curvature is different for the incident and scattered light path due to the asymmetry of the interface contact. FIG. 10D shows a container that is overfilled.

Table 3-1 shows the effects of a change of scattering angle (e.g., due to different meniscus curvature) on the determined nominal hydrodynamic radius of a particle. The values for $R_h$ were calculated according to equations 2 and 3. These data shown that a change in scattering angle of 5° can effect a deviation in determined hydrodynamic radius of 8% or more, and that a change of 10° can effect a deviation in determined hydrodynamic radius of more than about 15%.

TABLE 3-1

| scattering angle | Rh 25 nm | Rh 50 nm | Rh 75 nm | Rh 100 nm | % deviation |
|---|---|---|---|---|---|
| 132.1 | 29.3 | 58.5 | 87.8 | 117.0 | 17.0 |
| 129.6 | 28.2 | 56.3 | 84.5 | 112.7 | 12.7 |
| 127.1 | 27.1 | 54.2 | 81.3 | 108.4 | 8.4 |
| 124.6 | 26.0 | 52.1 | 78.1 | 104.1 | 4.1 |
| 122.1 | 25.0 | 50.0 | 75.0 | 100.0 | 0.0 |
| 119.6 | 24.0 | 48.0 | 72.0 | 95.9 | −4.1 |
| 117.1 | 23.0 | 46.0 | 69.0 | 92.0 | −8.0 |
| 114.6 | 22.0 | 44.0 | 66.1 | 88.1 | −11.9 |
| 112.1 | 21.1 | 42.1 | 63.2 | 84.3 | −15.7 |

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

All the disclosed embodiments of the invention described herein can be realized and practiced without undue experimentation. Although the best mode of carrying out the invention contemplated by the inventors is disclosed above, practice of the invention is not limited thereto. Further, all the disclosed elements and features of each disclosed embodiment can be combined with, or substituted for, the disclosed elements and features of every other disclosed embodiment except where such elements or features are mutually exclusive.

What is claimed is:

1. A method for characterizing a liquid sample or a component thereof, the method comprising
   providing a liquid sample contained in a vessel, the sample having an exposed surface that defines a gas-liquid sample interface, wherein the vessel defines a cavity having an upper edge, and the vessel is filled with the liquid sample substantially to the upper edge of the cavity so that the liquid-gas interface is substantially planar, and
   analyzing the sample by light-scattering methods that include transmitting light into the sample, and detecting the light scattered from the sample or a component thereof, the light being transmitted or detected through the gas-liquid sample interface.

2. The method of claim 1 wherein the light is transmitted through the gas-liquid sample interface, and the scattered light is detected through the gas-liquid sample interface.

3. The method of claim 1 wherein the light is transmitted through the gas-liquid sample interface, and the scattered light is detected through a bottom of the vessel.

4. The method of claim 1 wherein the sample is contained in an open-top vessel.

5. The method of claim 1 wherein the liquid sample is a first liquid sample, the method further comprising analyzing a second liquid sample having an exposed surface that defines a gas-liquid interface by light scattering methods that include transmitting light into the second sample, and detecting light scattered from the second sample or a component thereof, the light being transmitted or detected through the gas-liquid sample interface of the second sample.

6. The method of claim 5 wherein the first and second samples are analyzed sequentially.

7. The method of claim 5 wherein the average sample throughput for characterizing the first and second samples is not more than about 1 minute per sample.

8. The method of claim 1 wherein the sample or a component thereof is analyzed by static light scattering.

9. The method of claim 1 wherein the sample or a component thereof is analyzed by dynamic light scattering.

10. The method of claim 1 wherein the light scattering analysis further comprises determining at least one property of the sample or of a component thereof, the determined property being selected from the group consisting of particle size, particle size distribution, molar mass and molar mass distribution.

11. The method of claim 1 wherein the liquid sample is a solution, emulsion, dispersion or suspension.

12. A method for characterizing a plurality of liquid samples or components thereof, the method comprising
   providing a plurality of liquid samples, each of the plurality of samples having an exposed surface that defines a gas-liquid sample interface, and
   analyzing the plurality of samples in parallel by light scattering methods that include simultaneously transmitting light into each of the plurality of samples, and detecting light scattered from each of the plurality of samples or a component thereof, the light being transmitted or detected through the gas-sample interface of each of the plurality of samples.

13. A method for characterizing a plurality of liquid samples or components thereof, the method comprising
   providing a library comprising a plurality of different samples,
   analyzing a first sample of the plurality of liquid samples by light-scattering methods that include transmitting light from a light-scattering probe into the first sample, and detecting light scattered from the first sample or a component thereof,
   translating the plurality of samples or the light-scattering probe relative to each other, and
   analyzing a second sample of the plurality of liquid samples by light-scattering methods that include transmitting light from the probe into the second sample, and detecting light scattered from the second sample or a component thereof.

14. A method for characterizing a plurality of liquid samples or components thereof, the method comprising
   providing four or more liquid samples,
   providing an array of two or more light scattering probes,
   analyzing a first plurality of the four or more samples in parallel by light scattering methods that include simultaneously transmitting light from the two or more probes into the first plurality of samples, and detecting light scattered from the first plurality of samples or a component thereof, translating the four or more samples or the array of two or more probes relative to each other, and
   analyzing a second plurality of the four or more samples in parallel by light scattering methods that include simultaneously transmitting light from two or more probes into the second plurality of samples, and detecting light scattered from the second plurality of samples or a component thereof.

15. A method for identifying useful materials, the method comprising
   providing a library of liquid samples, the library comprising four or more different liquid samples,
   analyzing at least four samples of the library in parallel by light scattering methods that include simultaneously transmitting light into the at least four samples of the library, detecting light scattered from the at least four samples of the library or components thereof, and determining a property of the at least four samples of the library or components thereof, and
   comparing the determined property of each of the at least four samples of the library.

16. The method of claim 13 wherein the first and second liquid samples each have an exposed surface that defines a gas-liquid sample interface, light is transmitted or detected through the gas-liquid sample interface of the first sample, and light is transmitted or detected through the gas-liquid sample interface of the second sample.

17. The method of claim 14 herein each of the four or more samples has an exposed surface that defines a gas-liquid sample interface, and light is transmitted or detected through the gas-liquid sample interface of each of the four or more samples.

18. The method of claim 15 wherein each of the four or more samples has an exposed surface that defines a gas-liquid sample interface, and light is transmitted or detected through the gas-liquid sample interface of each of the four or more samples.

19. The method of claims 12, 16, 17 or 18 wherein the light is transmitted through the gas-liquid sample interface, and the scattered light is detected through the gas-liquid sample interface.

20. The method of claims 12, 16, 17 or 18 wherein the analyzed samples are contained in a vessel, the light is transmitted through a gas-liquid sample interface, and the scattered light is detected through a bottom of the vessel.

21. The method of claims 12, 16, 17 or 18 wherein the gas-liquid sample interface of the analyzed samples is substantially planar in the region through which the light is transmitted.

22. The method of claims 12, 13, 14 or 15 wherein the samples or a component thereof are analyzed by static light scattering.

23. The method of claims 12, 13, 14 or 15 wherein the samples or a component thereof are analyzed by dynamic light scattering.

24. The method of claims 12, 13 or 14 wherein the light scattering analysis further comprises determining at least one property of each of the plurality of samples or of a component thereof, the determined property being selected from the group consisting of particle size, particle size distribution, molar mass and molar mass distribution.

25. The method of claims 12, 13 or 14 wherein the four or more liquid samples are different from each other.

26. The method of claims 12, 13, 14 or 15 wherein the liquid samples are a solution, emulsion, dispersion or suspension.

27. The method of claim 14 wherein the samples are translated relative to the array of two or more probes.

28. The method of claim 14 wherein the array of two or more probes is translated relative to the samples.

29. The method of claims 13 or 14 wherein the analysis by light-scattering further includes immersing each of the two or more light scattering probes into a sample.

30. The method of claim 15 wherein the library comprises four or more different liquid samples on or in a common substrate.

31. The method of claims 12, 13, 14 or 15 wherein the average sample throughput for characterizing the samples is not more than about 10 minutes per sample.

32. The method of claims 12 13, 14 or 15 wherein the average sample throughput for characterizing the samples is not more than about 1 minute per sample.

33. The method of claim 13 wherein the plurality of liquid samples are provided on a common sample holder.

34. The method of claims 14 or 15 wherein the four or more liquid samples are provided on a common sample holder.

35. The method of claims 14 or 15 wherein the four or more liquid samples are provided on two or more sample holders.

36. The method of claim 15 wherein the at least four samples of the library are analyzed using an array of four or more light scattering probes.

37. The method of claim 15 wherein the library of liquid samples comprises the four or more samples on a common sample holder, and the four or more samples are analyzed using an array of light scattering probes, the number and spatial arrangement of probes included in the array corresponding to the number and spatial arrangement of the samples on the sample holder.

38. The method of claim 15 wherein the library of liquid samples is a first library of liquid samples, the first library of samples is provided on a first sample holder, and light is simultaneously transmitted from an array of four or more light scattering probes into the at least four samples of the first library, the method further comprising providing a second library of liquid samples on a second sample holder, the second library comprising four or more different liquid samples, translating the second sample holder or the array of probes relative to each other, and analyzing at least four samples of the second library in parallel by light scattering methods that include simultaneously transmitting light from the array of probes into at least four samples of the second library, detecting light scattered from the at least four samples of the second library or components thereof, and determining a property of the at least four samples of the second library or components thereof, and comparing the determined property of the at least four samples of the second library.

39. The method of claim 38 wherein the number and spatial arrangement of the samples on the first-and-second sample holders is the same, and the number and spatial arrangement of probes included in the array corresponds to the number and spatial arrangement of the samples on the first and second sample holders.

40. An apparatus for characterizing a plurality of liquid samples, the apparatus comprising a sample holder for presenting an array of four or more liquid samples, and a probe head comprising an array of two or more fiber optic probes arranged to correspond to the array of samples or a subset thereof, each of the two or more fiber optic probes being adapted to simultaneously illuminate the liquid samples for light scattering analysis.

41. The apparatus of claim 40 wherein each of the two or more fiber optic probes are further adapted to simultaneously detect light scattered from the plurality of liquid samples or a component thereof.

42. The apparatus of claim 40 wherein the sample holder is adapted to present the array of four or more liquid samples with an exposed gas-liquid interface, and each of the two or more fiber optic probes are adapted to simultaneously illuminate the liquid samples through the gas-liquid interface.

43. The apparatus of claim 40 further comprising a translation station for translating the sample holder or the probe head relative to each other.

44. The apparatus of claim 43 wherein the sample holder is adapted to present the four or more samples in a substantially coplanar relationship to each other, the probe head comprises the two or more fiber optic probes in a substantially coplanar relationship to each other, and the translation station is adapted to translate the sample holder or the probe head in a plane that is substantially parallel to the plane defined by the array of fiber optic probes or the samples, respectively.

45. The apparatus of claim 43 wherein the sample holder is adapted to present the four or more samples in a substantially coplanar relationship to each other, and the translation station is adapted to translate the sample holder or the probe head in a direction that is substantially normal to the plane defined by the samples.

46. The apparatus of claim 40 wherein the sample holder is adapted to present the four or more samples in a substantially coplanar relationship to each other, and the probe head is positionable over the sample holder such that the array of fiber optic probes can simultaneously illuminate two or more of the liquid samples from above the plane comprising the samples.

47. The apparatus of claim 46 wherein each of the two or more fiber optic probes are further adapted to simultaneously detect light scattered from the plurality of liquid samples or a component thereof.

48. The apparatus of claim 46 wherein the probe head is a first probe head that comprises a first array of two or more fiber optic probes, the apparatus further comprising a second probe head that comprises a second array of two or more fiber optic probes arranged to correspond to the array of samples or a subset thereof, the second probe head being positionable under the sample holder such that the second array of two or more fiber optic probes can simultaneously detect light scattered from the plurality of liquid samples or a component thereof.

49. The apparatus of claim 46 further comprising a translation station for translating the sample holder or the probe head relative to each other.

50. The apparatus of claim 40 further comprising four or more open-top vessels situated in the sample holder and suitable for containing the four or more liquid samples.

51. The apparatus of claim 40 wherein the sample holder comprises a common substrate having a plurality of wells or vessels.

52. The apparatus of claim 40 wherein the sample holder is a microtiter plate.

53. The apparatus of claim 40 wherein each of the two or more fiber optics probes are immersion probes.

54. The apparatus of claim 53 further comprising a washing station for simultaneously washing each of the two or more fiber optic probes to reduce contamination from samples into which the probes were immersed.

55. The apparatus of claim 40 wherein each of the two or more fiber optic probes comprises an illumination fiber and a detection fiber.

56. The apparatus of claim 40 wherein each of the two or more fiber optic probes comprises an illumination fiber and a detection fiber that defines a detection angle with respect to the illumination fiber, and one or more tuning members for adjusting the detection angle.

57. A method for characterizing a liquid sample or a component thereof, the method comprising
   providing a liquid sample contained in a vessel, the sample having a surface that defines a gas-liquid sample interface, wherein the vessel is defined by a cavity having an upper edge and an intermediate ledge, and the vessel is filled with the liquid sample substantially to the intermediate ledge of the cavity so that the liquid-gas interface is substantially planar, and
   analyzing the sample by light-scattering methods that include transmitting light into the sample, and detecting the light scattered from the sample or a component thereof, the light being transmitted or detected through the gas-liquid sample interface.

58. The method of claim 57, wherein the vessel is a closed-top vessel having a transparent cover.

59. The method of claim 57, wherein the vessel is an open-top vessel.

60. A method for characterizing a liquid sample or a component thereof, the method comprising
   providing a liquid sample contained in a vessel, the sample having a surface that defines a gas-liquid sample interface, wherein the vessel defines a cavity having an interior surface and a coating formed on the interior surface, and the vessel is filled with the liquid sample to contact the coating so that the liquid-gas interface is substantially planar in the region through which light is detected or transmitted, and
   analyzing the sample by light-scattering methods that include transmitting light into the sample, and detecting the light scattered from the sample or a component thereof, the light being transmitted or detected through the gas-liquid sample interface.

61. The method of claim 60, wherein the vessel is a closed-top vessel having a transparent cover.

62. The method of claim 60, wherein the vessel is an open-top vessel.

* * * * *

UNITED STATES PATENT AND TRADEMARK OFFICE
CERTIFICATE OF CORRECTION

PATENT NO.    : 6,519,032 B1
DATED         : February 11, 2003
INVENTOR(S)   : Kuebler et al.

It is certified that error appears in the above-identified patent and that said Letters Patent is hereby corrected as shown below:

Column 53,
Line 28, "claim 40" should be replaced with -- claim 46 --

Signed and Sealed this

Twenty-fourth Day of June, 2003

JAMES E. ROGAN
*Director of the United States Patent and Trademark Office*